US007306805B2

(12) United States Patent
Bakaletz et al.

(10) Patent No.: US 7,306,805 B2
(45) Date of Patent: Dec. 11, 2007

(54) **NONTYPEABLE *HAEMOPHILUS INFLUENZAE* VIRULENCE FACTORS**

(75) Inventors: Lauren O. Bakaletz, Hilliard, OH (US); Robert S. Munson, Jr., Hilliard, OH (US)

(73) Assignee: Children's Hospital, Inc., Columbus, OH (US)

( * ) Notice: Subject to any disclaimer, the term of this patent is extended or adjusted under 35 U.S.C. 154(b) by 433 days.

(21) Appl. No.: 10/807,746

(22) Filed: Mar. 24, 2004

(65) Prior Publication Data

US 2004/0219585 A1    Nov. 4, 2004

Related U.S. Application Data

(60) Provisional application No. 60/458,234, filed on Mar. 27, 2003.

(51) Int. Cl.
*A61K 39/02* (2006.01)

(52) U.S. Cl. ............................... 424/190.1; 424/256.1; 424/185.1; 530/350; 530/300

(58) Field of Classification Search ............. 424/256.1, 424/185.1, 190.1; 530/300, 350
See application file for complete search history.

(56) References Cited

OTHER PUBLICATIONS

Wood (Guide to Molecular Cloning Techniques. vol. 152. 1987. Section IX. Chapter 49, pp. 443-447).*
Genbank Accession No. P45285 Fleischmann, et al., "Peptide Transport Periplasmic Protein sapA Precursor" (Sep. 13, 2005).
Fleischmann, et al., "Whole-Genome Random Sequence and Assembly of *Haemophilus influenzae* Rd", Science 269: 496-512 (Jul. 28, 1995).
Genbank Accession No. U32837 Fleischmann, et al., "*Haemophilus influenzae* Rd KW20 section 152 of 163 of the complete genome" (Jun. 2, 2004).
Barenkamp, et al., Outer Membrane Protein and Biotype Analysis of Pathogenic Nontypable *Haemophilus influenzae, Infection and Immunity*, 36(2): 535-540 (May 1982).
Musser, et al., Genetic Relationships of Serologically Nontypable and Serotype b Strains of *Haemophilus influenzae, Infection and Immunity*, 52(1): 183-191 (Apr. 1986).
Spinola, et al., Epidemiology of Colonization by Nontypable *Haemophilus influenzae* in Children: A Longitudinal Study, *Journal of Infectious Diseases*, 154(1): 100-109 (Jul. 1986).
Bakaletz, et al., Frequency of Fimbriation of Nontypable *Haemophilus influenzae* and Its Ability To Adhere to Chinchilla and Human Respiratory Epithelium, *Infection and Immunity*, 56(2): 331-335 (Feb. 1988).
Parra-Lopez, et al., Molecular Genetic Analysis of a Locus Required For Resistance to Antimicrobial Peptides in *Salmonella typhimurium*, *EMBO* 12(11): 4053-4062 (1993).

Bakaletz, et al., Modeling Adenovirus Type 1-Induced Otitis Media in the Chinchilla: Effect on Ciliary Activity and Fluid Transport Function of Eustachian Tube Mucosal Epithelium, *Journal of Infectious Diseases*, 168: 865-872 (1993).
Suzuki, et al., Synergistic Effect of Adenovirus Type 1 and Nontypeable *Haemophilus influenzae* in a Chinchilla Model of Experimental Otitis Media, *Infection and Immunity*, 62(5): 1710-1718 (May 1994).
Giebink, Immunology: Promise of New Vaccines, P*ed. Infect Dis. J.*, 13(11): 1064-1068 (1994).
Karma, et al., Immunological Aspects of Otitis Media: Present Views on Possibilities of Immunoprophylazis of Acute Otitis Media in Infants and Children, *International Journal of Pediatric Otorhinolaryngology*, 32 (Suppl.): S127-S134 (1995).
DeMaria, et al., Immunization with Outer Membrane Protein P6 from Nontypeable *Haemophilus influenzae* Induces Bactericidal Antibody and Affords Protection in the Chinchilla Model of Otitis Media, *Infection and Immunity*, 64(12): 5187-5192 (Dec. 1996).
Jerome, Role of Nontypeable *Haemophilus influenzae* in Pediatric Respiratory Tract Infections, *Ped. Infect Dis. J.*, 16(2): S5-S8 (Feb. 1997).
Bakaletz, et al., Relative Immunogenicity and Efficacy of Two Synthetic Chimeric Peptides of Fimbrin as Vaccinogens Against Nasopharyngeal Colonization by Nontypeable *Haemophilus infulenzae* in the Chinchilla, *Vaccine*, 15(9): 955-961 (Jun. 1997).
Holmes, et al., Adherence of Non-Typeable *Haemophilus influenzae* Promotes Reorganization of the Actin Cytoskeleton in Human or Chinchilla Epithelial Cells in vitro, *Microblal Pathogenesis*, 23: 157-166 (1997).
López-Solanilla, et al., Inactivation of the *sapA* to *sapF* Locus of *Erwinia chrysanthemi* Reveals Common Features in Plant and Animal Bacterial Pathogenesis, *Plant Cell*, 10: 917-924 (Jun. 1998).
Bakaletz, et al., Protection against Development of Otitis Media Induced by Nontypeable *Haemophilus influenzae* by Both Active and Passive Immunization in a Chinchilla Model of Virus-Bacterium Superinfection, *Infect. Immunity* 67(6): 2746-2762 (Jun. 1999).
Novotny, et al., Epitope Mapping of the Outer Membrane Protein P5-Homologous Fimbrin Adhesin of Nontypeable *Haemophilus influenzae, Infection and Immunity*, 68(4): 2119-2128 (Apr. 2000).
Kennedy, et al., Passive Transfer of Antiserum Specific for Immunogens Derived from a Nontypeable *Haemophilus influenzae* Adhesin and Lipoprotein D Prevents Otitis Media after Heterologous Challenge, *Infection and Immunity*, 68(5): 2756-2765 (May 2000).

(Continued)

*Primary Examiner*—Jennifer E. Graser
(74) *Attorney, Agent, or Firm*—Marshall, Gerstein & Borun LLP

(57) ABSTRACT

The invention relates to a mutation within the sap operon of an avirulent clone of a nontypeable strain of *Haemophilus influenzae* (NTHi). The invention also relates to the NTHi sap operon genes and the polypeptides encoded by these polynucleotide sequences. The invention also relates to a novel 110 kDa NTHi outer membrane protein and the polynucleotide that encodes this outer membrane protein. Methods of screening for NTHi infection, and treating and preventing NTHi related disorders are also contemplated.

3 Claims, 7 Drawing Sheets

OTHER PUBLICATIONS

Black, et al., Efficacy, Safety and Immunogenicity of Heptavalent Pneumococcal Conjugate Vaccine in Children, *Ped. Infect. Dis. J.*, 19(3): 187-195 (2000).

Eskola, et al., Potential of Bacterial Vaccines in the Prevention of Acute Otitis Media, *Ped. Infect. Dis. J.*, 19(5): S72-S78 (2000).

Eskola, et al., Efficacy of A Pneumococcal Conjugate Vaccine Against Acute Otitis Media, *N. Engl. J. Med.*, 344(6): 403-409 (Feb. 2001).

Poolman, et al., Developing a Nontypeable *Haemophilus influenzae* (NTHi) Vaccine, *Vaccine*, 19: S108-S115 (2001).

Snow, Progress in the Prevention of Otitis Media Through Immunization, *Otology & Neurotology*, 23(1): 1-2 (2002).

Genebank Accession No. Q9K1VA, Hemoglobin Binding Protein A Precursor, Oct. 16, 2001.

Parra-Lopez et al., A *Salmonella* Protein that is Required for Resistance to Antimicrobial Peptides and Transport of Potassium, *EMBO J.* 13(17): 3964-3972 (1994).

Bakaletz et al., Evidence for Transduction of Specific Antibodies into the Middle Ear of Parenterally Immunized Chinchillas after an Upper Respiratory Infection with Adenovirus *Clin. Diag. Lab. Immunol.* 4(2): 223-225 (Mar. 1997).

McCoy et al., Identification of *Proteas mirabilis* with Increased Sensitivity AntiMicrobial Peptides, *Antimicrob. Agents Chemother.* 45(7): 2030-2037 (Jul. 2001).

* cited by examiner

A. Input pool hybridization

B. Recovery pool hybridization

```
                           SEQUENCE LISTING

<160> NUMBER OF SEQ ID NOS: 41

<210> SEQ ID NO 1
<211> LENGTH: 1695
<212> TYPE: DNA
<213> ORGANISM: H. influenzae

<400> SEQUENCE: 1
atgttacgtc taaatctgag atttttatct tttctgctct gtataagcca aagtgtagaa      60
ttacaggctg cgccaagtgt tccaacattt ttaactgaaa atggcttaac ttattgcacc     120
cacgcttcag gtttttcatt taatccgcaa acagcagatg caggaaccag tatgaatgtg     180
gtcacggaac aaatttataa caattatttt gatataaaaa atcacagtgc aacattaaca     240
ccaatgctgg cacaatctta ttccatttca gctgatggta aagaaatttt attaaattta     300
cgtcacggcg taaaatttca ccaaaccct tggtttaccc caacacgtga ttttaacgct      360
gaagacgtag tattttcgat taatcgtgta ttagggcata atacttattt accaacctta     420
gcagaggcga atgttaccta tagtaatcca caatatagag tgtttcacga acaagcaaga     480
aaagtgcgtt ttccttattt tgatagcatt aaacttaacg aaaaaatcaa atctgtgacc     540
gcactttcgc cttatcaagt aaaaattgaa ttatttgcac cagattcctc cattttgtcg     600
catcttgcca gccagtatgc cattattttt tcacaagaat atgcctatca attaagcgca     660
gatgacaacc ttgctcaatt agatacccac ccagtaggca cagggcctta tcaagtaaaa     720
gattatgtat ataaccaata tgttcgctta gtgcgtaacg aaaactattg gaaaaagaa      780 gccaagatag aacatattat tgtggatctt tctactgatc gcagcggacg tttagtcaaa     840
tttttcaata atgaatgtca aatcgcctct tatcctgaag taagccaaat tggcttatta     900
aaaaatgatg acaaacatta ttatatgcaa tctactgatg gtatgaattt agcctattta     960
```

-continued

```
gcgtttaatt tgataagcc attaatgcga gatcacgaaa tccgtgctgc tatttcacaa    1020
agtttaaacc gagctcgaat cattcatagc atttaccata acacagcaac tgttgctaat    1080
aacattattc ctgaagtgtc ttgggcttca actgtcaata cgccagaatt tgagtttgat    1140
taccatccca aaatcgccaa aaataaatta gcagataaaa acctttgtt aaatttatgg     1200 gtaattaatg aagaacaagt ctataatcca gcacctttta aaatggctga atgatcaaa    1260 tgggatttag ctcaagcggg tgtgaaagtt aaagtgcgtg ccgtaactcg tccatttta    1320 actgcacaat tacgcaatca atcggaaaat tatgatttga ttctatctgg ttggttagct    1380
ggtaatcttg atcctgatgg ttttatgcgt ccaattttaa gctgtggaac aaaaaatgaa   1440
ctcactaatt tatctaattg gtgtaatgaa gaatttgatc aatttatgga tcgtgccatt    1500
accacctcac atttaagttc acgcgcaaaa gcctataatg aagcccaaga actcgtttta    1560
cgtgaattac ccattattcc tattgccaat gtaaaacgaa ttttagtcgc aaatagtcgt    1620
gtgaaaggag taaaaatgac gcctttggt agcttagatt tttccacctt atattttatt    1680
caggagaaac actaa                                                     1695

<210> SEQ ID NO 2
<211> LENGTH: 966
<212> TYPE: DNA
<213> ORGANISM: H. influenzae

<400> SEQUENCE: 2
atgttctggt cggttcttcg ccatattctg tgggtggcat tattattact cgtattatcg     60
ctattaggct ttgttatttt attgcgcgat cctcttaatg cgaatcttgt tacacaaaac    120
atttatatcg gctatttcca ttatttaggc accttgttac aaggtgattt tggcattacc    180
tataacggtg aaaatcatt aatgaacctt attcttacgg ttcttcctcc cacattggaa     240 cttttgtttca ttacattgtt tttggcattt atttttggtt tgccacttgg cattataagt    300
gcggtcaatt ctgaacaagt ttttgcaaaa agtttacaaa tcctatctta tgtagggcta    360
tctattccaa tattttggtt agccccccatt ttactgtatg ttgccgcgct ctcacattgg    420
gaaattgccg ctattggaca atataaatttg ctttacgaaa ttaaacccat tacgggattt    480
cctgttattg atatgtggtt tatggaagta ccttatcgta caaaaatcgt acaaaacata    540
ttgcaacatt tagccttacc aacattggta ttgtgtattt tgccaacaat ggaaattatc    600
cgtattattc atcaacgagc agaatatatt ttgaatcaaa attttttctaa agtagcgaca    660 acacggggtt ggtcaaaatg gaaaattctc catcaatatg tattccgtaa tacttttccc    720
ctgcttgttc cacaagtacc acgtgtattc acattagtat taacgcaatg tatgttggta    780
gaaacggctt taggttggcc tggcattggt cgttggttaa ttaatgccgt aaatgaacaa    840
gattacaaca gcattgccgc aggtgtaatt gttattggtg tatgtattat tttgattgat    900
acattcacta aatattcac ttttatactc gatccattta aaagaaagg ttggtatgca     960 agataa                                                              966

<210> SEQ ID NO 3
<211> LENGTH: 888
<212> TYPE: DNA
<213> ORGANISM: H. influenzae

<400> SEQUENCE: 3
atgcaagata aagaacctga tgaattccgc gaaagcacct caatctttca aatttggtta     60
cgctttcgtc aaaataccat cgcactttt agcttttatt tattaatcgc attaattttt    120
```

-continued

```
accgcacttt tgctagtta tcttgcacct tatgctgata atcgacaatt tattgggcaa      180
gaattaatgc ctccttcttg ggtagataga ggaaaaattg ctttttcctt tggtactgat      240
gatttaggtc gcgacatatt aagtcgttta attatgggta ctcgttatac cttaggttct      300
gctttactgg ttgtcttttc agtggcaata ataggcggcg cactaggaat tattgcagga      360
ctactgaaag gtattaaagc tcgttttgtc gggcatattt ttgatgcttt tttatcgtta      420
cctattctat taattgccgt tgttatttca acattaatgg aaccaagttt atggaatgca      480
atgtttgcta cgctattagc aattttgcct tatttcattc acactatcta tcgcgctatt      540 caaaagaat tagaaaagga ttatgttgta atgctaaaac ttgaaggcat ttccaatcaa      600
accttattaa aaagcactat tttaccgaat attactgtta tttatattca agaagtggct      660
catgcttttg ttatagccgt gttggatatt agcgcattaa gttttatttc tcttggtgca      720
caacgaccta caccagaatg gggggcaatg ataaaagact cttttggaact actttatctt      780 gcaccttgga cagtactttt acccggtttc gctattattt ttactatttt attaagtatt      840
attttcagta atggcttaac taaagccatc aatcaacatc aagaatag              888
```

<210> SEQ ID NO 4
<211> LENGTH: 1050
<212> TYPE: DNA
<213> ORGANISM: H. influenzae

<400> SEQUENCE: 4

```
atggcacttt tagacatttg taacctcaat attgaaattc aaacctccaa tggacgtata       60
aaaattgtag atggcgtcaa tcttttccctt aacgaagggg aaatcagtgg attagttggc      120
gaatcaggct caggaaaaag cttaatcgct aaagtcattt gtaatgcaat caagaaaat      180 tggattatta ctgccgatcg ctttcgtttt cacgatatcg aattactaaa actcagtcct      240
aataaacgac gtaagattgt cggcaaagaa atatccatga ttttccaaaa tcccttatct      300
tgccttgatc caagtcgaaa atagggaaa caactcatcc aaaatattcc taattggaca      360
tttaaaaata atggtggaa atggtttggg tggaaaaaaa gacgtgctat tgaattgtta      420
catcgcgtag gaattaaaga tcatcgtgat attatggcaa gctatcctaa cgaactgaca      480
gaaggcgaag gacaaaaagt tatgatcgca atggctgtcg ctaatcagcc acgtttatta      540
atcgcagatg aaccaacaaa tacattagaa tcaaccactg ccctacaagt ttttcgttta      600 cttttccagta tgaaccaaaa tcagggaaca acaattttac ttacgagtaa cgatattaaa      660
agtattagtg aatggtgcga tcaaatttca gtgctttatt gtgggcaaaa taccgaatct      720
gccccgactg aaatattaat cgaaagtccc catcatcctt atacccaagc cttaattaat      780
gcagtacccg atttttactca acctttgggg tttaaaacta aattgggtac gttagaaggc      840
accgcgccta tttttagagca aatgccaatt ggctgtcgtc ttggccaag atgccctttt      900 gcacaaaaaa aatgtatgga aaaccaaga cgattgaaaa taaacaaca cgaatttct       960 tgtcattatc ctattaattt acgagaaaaa aatttcaaag aaaaaacaac cgccaccct     1020 ttttatactta attgcaaagg aaatgaataa                                    1050
```

<210> SEQ ID NO 5
<211> LENGTH: 810
<212> TYPE: DNA
<213> ORGANISM: H. influenzae

<400> SEQUENCE: 5

```
atgcccttat tacaagtgga agatttaact aaaacttttta aaggtcacgc cagtttattt    60
ggtcgaaatc aattcaatgc agtggataaa gtgagtttta cccttgaacg taaacaaaca   120
cttgcaatca ttggcaataa tggctctggt aaatcaactc tagtgaaaat gatagcgggc   180
attattccgc caacttctgg tcgaatttta tttaatgatc gagaattaca atatcaggat   240
gcccaatcta gagctaaaca tattcgtatg gttttccaag atgccaactc tgcatttaat   300
ccacgtttaa atattggaca aatattagac gaaccattaa gcctagcgac agattggaca   360
gaaacacaac gtaatgaaaa atctttgag accctctctc ttgttggact ttatcctgat   420
tacacaaatc tcaatattaa gcatctctct atcagccaaa agcagcgggt tgccctagca   480
cgcgcattaa ttttagcacc agaaattatt aaatagatg atgcaattgg caatttagat   540
gcttctgtac gtattcaatt gcttaattta acccttgatt tacaacaacg tttaggtata   600
tcttatattt atgtgggaca ggatctcggt gtaattaaac atattgcaga tacgattatc   660
gtaatggatg acgaaaaaat gattgaatat ggcagccctc aaaatctttt tactgatcca   720
caaactgatg ttactcgtcg cttagtcgaa agctattttg gcaaaatttt agatgaaacc   780
gcttgggtaa aagacaaaaa cactcactaa                                    810
```

<210> SEQ ID NO 6
<211> LENGTH: 1017
<212> TYPE: DNA
<213> ORGANISM: H. influenzae

<400> SEQUENCE: 6

```
atgaacactc gtccctttta tttcggactt atatttattg cgattatcgc tatacttgct    60
cactatttag gaaacactga ttttttcccat cattatcata tcagtgctct aattattgcc   120
atcttgctgg gaatggcaat cggcaatacc atttatccgc aattttcaac acaagtggaa   180
aaaggcgtgt tatttgcgaa aggcacgctt cttcgcactg gcattgtgct gtatggtttt   240
cgccttactt ttggcgatat tgccgatgtt ggcttaaatg ctgttgtcac tgatgcgatt   300
atgctaattt caacctttttt tcttaccgca cttttgggca ttcgttatct aaaaatggat   360
aaacaattgg tttatctcac tggggctgga tgtagtattt gtggtgcggc agcggttatg   420
gcggcagagc ctgttaccaa agcagaatct cataaagttt cagtagcgat tgccgtagtg   480
gtcattttcg ggacgcttgc tattttttact tacccccttgt tctacacgtg gtcacaagat   540
ttaattaacg cccatcaatt cggtatttat gttggttcta gtgtacgaa agtggctcaa   600 gtgtatgcga ttggggaaaa tattgatcct atcgtggcga atactgccgt catttccaaa   660
atgatccgag tgatgatgct cgcaccattt ttattaatgc tttcttggtt attaacacgt   720
agtaatggaa tatcagaaaa tacatcacac aaaattacaa ttccttggtt tgctgtactt   780
tttattggcg ttgcgatttt taattctttt gatttattac caaaagaact cgtgaaatta   840
ttagttgaaa tcgattcttt cttattaatt tcagcgatgc ctgcccttgg cttaacgaca   900
caagcaagcg caatcaaaaa ggcaggatta aaaccacttg ttttaggaac actaatttat   960
ttatggctaa tggttggtgg attttttagtg aattatggaa tatcaaaatt aatataa    1017
```

<210> SEQ ID NO 7
<211> LENGTH: 564
<212> TYPE: PRT
<213> ORGANISM: Homo sapiens

<400> SEQUENCE: 7

Met Leu Arg Leu Asn Leu Arg Phe Leu Ser Phe Leu Leu Cys Ile Ser

-continued

```
1               5                   10                  15
Gln Ser Val Glu Leu Gln Ala Ala Pro Ser Val Thr Phe Leu Thr
                20                  25                  30

Glu Asn Gly Leu Thr Tyr Cys Thr His Ala Ser Gly Phe Ser Phe Asn
                35                  40                  45

Pro Gln Thr Ala Asp Ala Gly Thr Ser Met Asn Val Thr Glu Gln
            50                  55                  60

Ile Tyr Asn Lys Leu Phe Asp Ile Lys Asn His Ser Ala Thr Leu Thr
65                  70                  75                  80

Pro Met Leu Ala Gln Ser Tyr Ser Ile Ser Ala Asp Gly Lys Glu Ile
                85                  90                  95

Leu Leu Asn Leu Arg His Gly Val Lys Phe His Gln Thr Pro Trp Phe
            100                 105                 110

Thr Pro Thr Arg Asp Phe Asn Ala Glu Asp Val Val Phe Ser Ile Asn
            115                 120                 125

Arg Val Leu Gly His Asn Thr Tyr Leu Pro Thr Leu Ala Glu Ala Asn
            130                 135                 140

Val Thr Tyr Ser Asn Pro Gln Tyr Arg Val Phe His Glu Gln Ala Arg
145                 150                 155                 160

Lys Val Arg Phe Pro Tyr Phe Asp Ser Ile Lys Leu Asn Glu Lys Ile
                165                 170                 175

Lys Ser Val Thr Ala Leu Ser Pro Tyr Gln Val Lys Ile Glu Leu Phe
                180                 185                 190

Ala Pro Asp Ser Ser Ile Leu Ser His Leu Ala Ser Gln Tyr Ala Ile
            195                 200                 205

Ile Phe Ser Gln Glu Tyr Ala Tyr Gln Leu Ser Ala Asp Asp Asn Leu
            210                 215                 220

Ala Gln Leu Asp Thr His Pro Val Gly Thr Gly Pro Tyr Gln Val Lys
225                 230                 235                 240

Asp Tyr Val Tyr Asn Gln Tyr Val Arg Leu Val Arg Asn Glu Asn Tyr
                245                 250                 255

Trp Lys Lys Glu Ala Lys Ile Glu His Ile Ile Val Asp Leu Ser Thr
            260                 265                 270

Asp Arg Ser Gly Arg Leu Val Lys Phe Phe Asn Asn Glu Cys Gln Ile
            275                 280                 285

Ala Ser Tyr Pro Glu Val Ser Gln Ile Gly Leu Leu Lys Asn Asp Asp
            290                 295                 300

Lys His Tyr Tyr Met Gln Ser Thr Asp Gly Met Asn Leu Ala Tyr Leu
305                 310                 315                 320

Ala Phe Asn Phe Asp Lys Pro Leu Met Arg Asp His Glu Ile Arg Ala
                325                 330                 335

Ala Ile Ser Gln Ser Leu Asn Arg Ala Arg Ile Ile His Ser Ile Tyr
                340                 345                 350

His Asn Thr Ala Thr Val Ala Asn Ile Ile Pro Glu Val Ser Trp
            355                 360                 365

Ala Ser Thr Val Asn Thr Pro Glu Phe Glu Phe Asp Tyr His Pro Lys
370                 375                 380

Ile Ala Lys Asn Lys Leu Ala Asp Lys Asn Leu Leu Leu Asn Leu Trp
385                 390                 395                 400

Val Ile Asn Glu Glu Gln Val Tyr Asn Pro Ala Pro Phe Lys Met Ala
                405                 410                 415

Glu Met Ile Lys Trp Asp Leu Ala Gln Ala Gly Val Lys Val Lys Val
                420                 425                 430
```

```
Arg Ala Val Thr Arg Pro Phe Leu Thr Ala Gln Leu Arg Asn Gln Ser
        435                 440                 445

Glu Asn Tyr Asp Leu Ile Leu Ser Gly Trp Leu Ala Gly Asn Leu Asp
    450                 455                 460

Pro Asp Gly Phe Met Arg Pro Ile Leu Ser Cys Gly Thr Lys Asn Glu
465                 470                 475                 480

Leu Thr Asn Leu Ser Asn Trp Cys Asn Glu Glu Phe Asp Gln Phe Met
                485                 490                 495

Asp Arg Ala Ile Thr Thr Ser His Leu Ser Ser Arg Ala Lys Ala Tyr
            500                 505                 510

Asn Glu Ala Gln Glu Leu Val Leu Arg Glu Leu Pro Ile Ile Pro Ile
        515                 520                 525

Ala Asn Val Lys Arg Ile Leu Val Ala Asn Ser Arg Val Lys Gly Val
    530                 535                 540

Lys Met Thr Pro Phe Gly Ser Leu Asp Phe Ser Thr Leu Tyr Phe Ile
545                 550                 555                 560

Gln Glu Lys His

<210> SEQ ID NO 8
<211> LENGTH: 320
<212> TYPE: PRT
<213> ORGANISM: H. influenzae

<400> SEQUENCE: 8

Met Phe Trp Ser Val Leu Arg His Ile Leu Trp Val Ala Leu Leu Leu
1               5                   10                  15

Leu Val Leu Ser Leu Leu Gly Phe Val Ile Leu Leu Arg Asp Pro Leu
            20                  25                  30

Asn Ala Asn Leu Val Thr Gln Asn Ile Tyr Ile Gly Tyr Phe His Tyr
        35                  40                  45

Leu Gly Thr Leu Leu Gln Gly Asp Phe Gly Ile Thr Tyr Asn Gly Gly
    50                  55                  60

Lys Ser Leu Met Asn Leu Ile Leu Thr Val Leu Pro Pro Thr Leu Glu
65                  70                  75                  80

Leu Cys Phe Ile Thr Leu Phe Leu Ala Phe Ile Phe Gly Leu Pro Leu
                85                  90                  95

Gly Ile Ile Ser Ala Val Asn Ser Glu Gln Val Phe Ala Lys Ser Leu
            100                 105                 110

Gln Ile Leu Ser Tyr Val Gly Leu Ser Ile Pro Ile Phe Trp Leu Ala
        115                 120                 125

Pro Ile Leu Leu Tyr Val Ala Ala Leu Ser His Trp Glu Ile Ala Ala
    130                 135                 140

Ile Gly Gln Tyr Asn Leu Leu Tyr Glu Ile Lys Pro Ile Thr Gly Phe
145                 150                 155                 160

Pro Val Ile Asp Met Trp Phe Met Glu Val Pro Tyr Arg Thr Lys Ile
                165                 170                 175

Val Gln Asn Ile Leu Gln His Leu Ala Leu Pro Thr Leu Val Leu Cys
            180                 185                 190

Ile Leu Pro Thr Met Glu Ile Ile Arg Ile Ile His Gln Arg Ala Glu
        195                 200                 205

Tyr Ile Leu Asn Gln Asn Phe Ser Lys Val Ala Thr Thr Arg Gly Trp
    210                 215                 220

Ser Lys Trp Lys Ile Leu His Gln Tyr Val Phe Arg Asn Thr Phe Pro
225                 230                 235                 240
```

```
Leu Leu Val Pro Gln Val Pro Arg Val Phe Thr Leu Val Leu Thr Gln
                245                 250                 255

Cys Met Leu Val Glu Thr Ala Leu Gly Trp Pro Gly Ile Gly Arg Trp
            260                 265                 270

Leu Ile Asn Ala Val Asn Glu Gln Asp Tyr Asn Ser Ile Ala Ala Gly
            275                 280                 285

Val Ile Val Ile Gly Val Cys Ile Ile Leu Ile Asp Thr Phe Thr Lys
        290                 295                 300

Ile Phe Thr Phe Ile Leu Asp Pro Phe Lys Lys Lys Gly Trp Tyr Ala
305                 310                 315                 320

<210> SEQ ID NO 9
<211> LENGTH: 295
<212> TYPE: PRT
<213> ORGANISM: H. influenzae

<400> SEQUENCE: 9

Met Gln Asp Lys Glu Pro Asp Glu Phe Arg Glu Ser Thr Ser Ile Phe
1               5                   10                  15

Gln Ile Trp Leu Arg Phe Arg Gln Asn Thr Ile Ala Leu Phe Ser Phe
            20                  25                  30

Tyr Leu Leu Ile Ala Leu Ile Phe Thr Ala Leu Phe Ala Ser Tyr Leu
        35                  40                  45

Ala Pro Tyr Ala Asp Asn Arg Gln Phe Ile Gly Gln Glu Leu Met Pro
    50                  55                  60

Pro Ser Trp Val Asp Arg Gly Lys Ile Ala Phe Phe Gly Thr Asp
65                  70                  75                  80

Asp Leu Gly Arg Asp Ile Leu Ser Arg Leu Ile Met Gly Thr Arg Tyr
                85                  90                  95

Thr Leu Gly Ser Ala Leu Leu Val Val Phe Ser Val Ala Ile Ile Gly
            100                 105                 110

Gly Ala Leu Gly Ile Ile Ala Gly Leu Leu Lys Gly Ile Lys Ala Arg
        115                 120                 125

Phe Val Gly His Ile Phe Asp Ala Phe Leu Ser Leu Pro Ile Leu Leu
    130                 135                 140

Ile Ala Val Val Ile Ser Thr Leu Met Glu Pro Ser Leu Trp Asn Ala
145                 150                 155                 160

Met Phe Ala Thr Leu Leu Ala Ile Leu Pro Tyr Phe Ile His Thr Ile
                165                 170                 175

Tyr Arg Ala Ile Gln Lys Glu Leu Glu Lys Asp Tyr Val Val Met Leu
            180                 185                 190

Lys Leu Glu Gly Ile Ser Asn Gln Thr Leu Leu Lys Ser Thr Ile Leu
        195                 200                 205

Pro Asn Ile Thr Val Ile Tyr Ile Gln Glu Val Ala His Ala Phe Val
    210                 215                 220

Ile Ala Val Leu Asp Ile Ser Ala Leu Ser Phe Ile Ser Leu Gly Ala
225                 230                 235                 240

Gln Arg Pro Thr Pro Glu Trp Gly Ala Met Ile Lys Asp Ser Leu Glu
                245                 250                 255

Leu Leu Tyr Leu Ala Pro Trp Thr Val Leu Pro Gly Phe Ala Ile
            260                 265                 270

Ile Phe Thr Ile Leu Leu Ser Ile Ile Phe Ser Asn Gly Leu Thr Lys
        275                 280                 285

Ala Ile Asn Gln His Gln Glu
```

-continued

```
                290                 295

<210> SEQ ID NO 10
<211> LENGTH: 349
<212> TYPE: PRT
<213> ORGANISM: H. influenzae

<400> SEQUENCE: 10

Met Ala Leu Leu Asp Ile Cys Asn Leu Asn Ile Glu Ile Gln Thr Ser
1               5                   10                  15

Asn Gly Arg Ile Lys Ile Val Asp Gly Val Asn Leu Ser Leu Asn Glu
            20                  25                  30

Gly Glu Ile Ser Gly Leu Val Gly Glu Ser Gly Ser Gly Lys Ser Leu
        35                  40                  45

Ile Ala Lys Val Ile Cys Asn Ala Ile Lys Glu Asn Trp Ile Ile Thr
    50                  55                  60

Ala Asp Arg Phe Arg Phe His Asp Ile Glu Leu Leu Lys Leu Ser Pro
65                  70                  75                  80

Asn Lys Arg Arg Lys Ile Val Gly Lys Glu Ile Ser Met Ile Phe Gln
                85                  90                  95

Asn Pro Leu Ser Cys Leu Asp Pro Ser Arg Lys Ile Gly Lys Gln Leu
            100                 105                 110

Ile Gln Asn Ile Pro Asn Trp Thr Phe Lys Asn Lys Trp Trp Lys Trp
        115                 120                 125

Phe Gly Trp Lys Lys Arg Arg Ala Ile Glu Leu Leu His Arg Val Gly
130                 135                 140

Ile Lys Asp His Arg Asp Ile Met Ala Ser Tyr Pro Asn Glu Leu Thr
145                 150                 155                 160

Glu Gly Glu Gly Gln Lys Val Met Ile Ala Met Ala Val Ala Asn Gln
                165                 170                 175

Pro Arg Leu Leu Ile Ala Asp Glu Pro Thr Asn Thr Leu Glu Ser Thr
            180                 185                 190

Thr Ala Leu Gln Val Phe Arg Leu Leu Ser Ser Met Asn Gln Asn Gln
        195                 200                 205

Gly Thr Thr Ile Leu Leu Thr Ser Asn Asp Ile Lys Ser Ile Ser Glu
    210                 215                 220

Trp Cys Asp Gln Ile Ser Val Leu Tyr Cys Gly Gln Asn Thr Glu Ser
225                 230                 235                 240

Ala Pro Thr Glu Ile Leu Ile Glu Ser Pro His His Pro Tyr Thr Gln
                245                 250                 255

Ala Leu Ile Asn Ala Val Pro Asp Phe Thr Gln Pro Leu Gly Phe Lys
            260                 265                 270

Thr Lys Leu Gly Thr Leu Glu Gly Thr Ala Pro Ile Leu Glu Gln Met
        275                 280                 285

Pro Ile Gly Cys Arg Leu Gly Pro Arg Cys Pro Phe Ala Gln Lys Lys
    290                 295                 300

Cys Met Glu Lys Pro Arg Arg Leu Lys Ile Lys Gln His Glu Phe Ser
305                 310                 315                 320

Cys His Tyr Pro Ile Asn Leu Arg Glu Lys Asn Phe Lys Glu Lys Thr
                325                 330                 335

Thr Ala Thr Pro Phe Ile Leu Asn Cys Lys Gly Asn Glu
            340                 345

<210> SEQ ID NO 11
<211> LENGTH: 269
```

```
<212> TYPE: PRT
<213> ORGANISM: Homo sapiens

<400> SEQUENCE: 11

Met Pro Leu Leu Gln Val Glu Asp Leu Thr Lys Thr Phe Lys Gly His
1               5                   10                  15

Ala Ser Leu Phe Gly Arg Asn Gln Phe Asn Ala Val Asp Lys Val Ser
            20                  25                  30

Phe Thr Leu Glu Arg Lys Gln Thr Leu Ala Ile Ile Gly Asn Asn Gly
        35                  40                  45

Ser Gly Lys Ser Thr Leu Val Lys Met Ile Ala Gly Ile Ile Pro Pro
    50                  55                  60

Thr Ser Gly Arg Ile Leu Phe Asn Asp Arg Glu Leu Gln Tyr Gln Asp
65                  70                  75                  80

Ala Gln Ser Arg Ala Lys His Ile Arg Met Val Phe Gln Asp Ala Asn
                85                  90                  95

Ser Ala Phe Asn Pro Arg Leu Asn Ile Gly Gln Ile Leu Asp Glu Pro
            100                 105                 110

Leu Ser Leu Ala Thr Asp Trp Thr Glu Thr Gln Arg Asn Glu Lys Ile
        115                 120                 125

Phe Glu Thr Leu Ser Leu Val Gly Leu Tyr Pro Asp Tyr Thr Asn Leu
    130                 135                 140

Asn Ile Lys His Leu Ser Ile Ser Gln Lys Gln Arg Val Ala Leu Ala
145                 150                 155                 160

Arg Ala Leu Ile Leu Ala Pro Glu Ile Ile Ile Asp Asp Ala Ile
                165                 170                 175

Gly Asn Leu Asp Ala Ser Val Arg Ile Gln Leu Leu Asn Leu Thr Leu
            180                 185                 190

Asp Leu Gln Gln Arg Leu Gly Ile Ser Tyr Ile Tyr Val Gly Gln Asp
        195                 200                 205

Leu Gly Val Ile Lys His Ile Ala Asp Thr Ile Ile Val Met Asp Asp
    210                 215                 220

Gly Lys Met Ile Glu Tyr Gly Ser Pro Gln Asn Leu Phe Thr Asp Pro
225                 230                 235                 240

Gln Thr Asp Val Thr Arg Arg Leu Val Glu Ser Tyr Phe Gly Lys Ile
                245                 250                 255

Leu Asp Glu Thr Ala Trp Val Lys Asp Lys Asn Thr His
            260                 265

<210> SEQ ID NO 12
<211> LENGTH: 338
<212> TYPE: PRT
<213> ORGANISM: H. influenzae

<400> SEQUENCE: 12

Met Asn Thr Arg Pro Phe Tyr Phe Gly Leu Ile Phe Ile Ala Ile Ile
1               5                   10                  15

Ala Ile Leu Ala His Tyr Leu Gly Asn Thr Asp Phe Ser His His Tyr
            20                  25                  30

His Ile Ser Ala Leu Ile Ile Ala Ile Leu Leu Gly Met Ala Ile Gly
        35                  40                  45

Asn Thr Ile Tyr Pro Gln Phe Ser Thr Gln Val Glu Lys Gly Val Leu
    50                  55                  60

Phe Ala Lys Gly Thr Leu Leu Arg Thr Gly Ile Val Leu Tyr Gly Phe
65                  70                  75                  80
```

-continued

```
Arg Leu Thr Phe Gly Asp Ile Ala Asp Val Gly Leu Asn Ala Val Val
                85                  90                  95

Thr Asp Ala Ile Met Leu Ile Ser Thr Phe Phe Leu Thr Ala Leu Leu
            100                 105                 110

Gly Ile Arg Tyr Leu Lys Met Asp Lys Gln Leu Val Tyr Leu Thr Gly
        115                 120                 125

Ala Gly Cys Ser Ile Cys Gly Ala Ala Val Met Ala Ala Glu Pro
    130                 135                 140

Val Thr Lys Ala Glu Ser His Lys Val Ser Val Ala Ile Ala Val Val
145                 150                 155                 160

Val Ile Phe Gly Thr Leu Ala Ile Phe Thr Tyr Pro Leu Phe Tyr Thr
                165                 170                 175

Trp Ser Gln Asp Leu Ile Asn Ala His Gln Phe Gly Ile Tyr Val Gly
            180                 185                 190

Ser Ser Val His Glu Val Ala Gln Val Tyr Ala Ile Gly Glu Asn Ile
        195                 200                 205

Asp Pro Ile Val Ala Asn Thr Ala Val Ile Ser Lys Met Ile Arg Val
    210                 215                 220

Met Met Leu Ala Pro Phe Leu Leu Met Leu Ser Trp Leu Leu Thr Arg
225                 230                 235                 240

Ser Asn Gly Val Ser Glu Asn Thr Ser His Lys Ile Thr Ile Pro Trp
                245                 250                 255

Phe Ala Val Leu Phe Ile Gly Val Ala Ile Phe Asn Ser Phe Asp Leu
            260                 265                 270

Leu Pro Lys Glu Leu Val Lys Leu Leu Val Glu Ile Asp Ser Phe Leu
        275                 280                 285

Leu Ile Ser Ala Met Ala Ala Leu Gly Leu Thr Thr Gln Ala Ser Ala
    290                 295                 300

Ile Lys Lys Ala Gly Leu Lys Pro Leu Val Leu Gly Thr Leu Ile Tyr
305                 310                 315                 320

Leu Trp Leu Met Val Gly Gly Phe Leu Val Asn Tyr Gly Ile Ser Lys
                325                 330                 335

Leu Ile
```

<210> SEQ ID NO 13
<211> LENGTH: 6427
<212> TYPE: DNA
<213> ORGANISM: H. influenzae

<400> SEQUENCE: 13

```
atgttacgtc taaatctgag attttttatct tttctgctct gtataagcca aagtgtagaa    60
ttacaggctg cgccaagtgt tccaacattt ttaactgaaa atggcttaac ttattgcacc   120
cacgcttcag gttttttcatt taatccgcaa acagcagatg caggaaccag tatgaatgtg   180
gtcacggaac aaatttataa caaattattt gatataaaaa atcacagtgc aacattaaca   240
ccaatgctgg cacaatctta ttccatttca gctgatggta agaaaatttt attaaattta   300
cgtcacggcg taaatttca ccaaaccct tggtttaccc caacacgtga ttttaacgct   360
gaagacgtag tattttcgat taatcgtgta ttagggcata atacttattt accaacctta   420
gcagaggcga atgttaccta tagtaatcca caatatagag tgtttcacga caagcaaga   480
aaagtgcgtt ttccttattt tgatagcatt aaacttaacg aaaaaatcaa atctgtgacc   540
gcactttcgc cttatcaagt aaaaattgaa ttatttgcac cagattcctc cattttgtcg   600
catcttgcca gccagtatgc cattattttt tcacaagaat atgcctatca attaagcgca   660
```

```
gatgacaacc ttgctcaatt agatacccac ccagtaggca cagggcctta tcaagtaaaa    720
gattatgtat ataaccaata tgttcgctta gtgcgtaacg aaaactattg gaaaaagaa    780
gccaagatag aacatattat tgtggatctt tctactgatc gcagcggacg tttagtcaaa    840
tttttcaata atgaatgtca aatcgcctct tatcctgaag taagccaaat tggcttatta    900
aaaaatgatg acaaacatta ttatatgcaa tctactgatg tatgaattt agcctattta    960
gcgtttaatt ttgataagcc attaatgcga gatcacgaaa tccgtgctgc tatttcacaa   1020
agtttaaacc gagctcgaat cattcatagc atttaccata acacagcaac tgttgctaat   1080
aacattattc ctgaagtgtc ttgggcttca actgtcaata cgccagaatt tgagtttgat   1140
taccatccca aaatcgccaa aaataaatta gcagataaaa accttttgtt aaatttatgg   1200
gtaattaatg aagaacaagt ctataatcca gcaccttta aaatggctga atgatcaaa    1260
tgggatttag ctcaagcggg tgtgaaagtt aaagtgcgtg ccgtaactcg tccattttta   1320
actgcacaat tacgcaatca atcggaaaat tatgatttga ttctatctgg ttggttagct   1380
ggtaatcttg atcctgatgg ttttatgcgt ccaattttaa gctgtggaac aaaaaatgaa   1440
ctcactaatt tatctaattg gtgtaatgaa gaatttgatc aatttatgga tcgtgccatt   1500
accacctcac atttaagttc acgcgcaaaa gcctataatg aagcccaaga actcgtttta   1560
cgtgaattac ccattattcc tattgccaat gtaaaacgaa ttttagtcgc aaatagtcgt   1620
gtgaaaggag taaaaatgac gccttttggt agcttagatt tttccacctt atattttatt   1680
caggagaaac actaatgttc tggtcggttc ttcgccatat tctgtgggtg gcattattat   1740
tactcgtatt atcgctatta ggcttttgtta ttttattgcg cgatcctctt aatgcgaatc   1800
ttgttacaca aaacatttat atcggctatt tccattattt aggcaccttg ttacaaggtg   1860
attttggcat tacctataac ggtggaaaat cattaatgaa ccttattctt acggttcttc   1920
ctcccacatt ggaactttgt ttcattacat tgttttggc atttattttt ggtttgccac   1980
ttggcattat aagtgcggtc aattctgaac aagttttttgc aaaaagttta caaatcctat   2040
cttatgtagg gctatctatt ccaatatttt ggttagcccc cattttactg tatgttgccg   2100
cgctctcaca ttgggaaatt gccgctattg acaaatataa tttgctttac gaaattaaac   2160
ccattacggg atttcctgtt attgatatgt ggtttatgga agtaccttat cgtacaaaaa   2220
tcgtacaaaa catattgcaa catttagcct taccaacatt ggtattgtgt atthtgccaa   2280
caatggaaat tatccgtatt attcatcaac gagcagaata tattttgaat caaaatttt    2340
ctaaagtagc gacaacacgg ggttggtcaa atggaaaat tctccatcaa tatgtattcc   2400
gtaatacttt tcccctgctt gttccacaag taccacgtgt attcacatta gtattaacgc   2460
aatgtatgtt ggtagaaacg gctttaggtt ggcctggcat tggtcgttgg ttaattaatg   2520
ccgtaaatga acaagattac aacagcattg ccgcaggtgt aattgttatt ggtgtatgta   2580
ttatttttgat tgatacattc actaaaatat tcacttttat actcgatcca tttaaaaaga   2640
aaggttggta tgcaagataa agaacctgat gaattccgcg aaagcacctc aatctttcaa   2700
atttggttac gctttcgtca aaataccatc gcacttttta gcttttattt attaatcgca   2760
ttaattttta ccgcacttttt tgctagttat cttgcacctt atgctgataa tcgacaattt   2820
attgggcaag aattaatgcc tccttcttgg gtagatagag gaaaaattgc tttttctttt   2880
ggtactgatg atttaggtcg cgacatatta agtcgtttaa ttatgggtac tcgttatacc   2940
ttaggttctg cttttactggt tgtcttttca gtggcaataa taggcggcgc actaggaatt   3000
```

```
attgcaggac tactgaaagg tattaaagct cgttttgtcg ggcatatttt tgatgcttt    3060
ttatcgttac ctattctatt aattgccgtt gttatttcaa cattaatgga accaagttta   3120
tggaatgcaa tgtttgctac gctattagca attttgcctt atttcattca cactatctat   3180
cgcgctattc aaaaagaatt agaaaaggat tatgttgtaa tgctaaaact tgaaggcatt   3240
tccaatcaaa ccttattaaa aagcactatt ttaccgaata ttactgttat ttatattcaa   3300
gaagtggctc atgcttttgt tatagccgtg ttggatatta gcgcattaag ttttatttct   3360
cttggtgcac aacgacctac accagaatgg ggggcaatga taaaagactc tttggaacta   3420
cttttatcttg caccttggac agtacttta cccggtttcg ctattatttt tactattta   3480
ttaagtatta ttttcagtaa tggcttaact aaagccatca atcaacatca agaatagcct   3540
atggcacttt tagacatttg taacctcaat attgaaattc aaacctccaa tggacgtata   3600
aaaattgtag atggcgtcaa tcttttccctt aacgaagggg aaatcagtgg attagttggc   3660
gaatcaggct caggaaaaag cttaatcgct aaagtcattt gtaatgcaat caagaaaat    3720
tggattatta ctgccgatcg ctttcgttt cacgatatcg aattactaaa actcagtcct   3780
aataaacgac gtaagattgt cggcaaagaa atatccatga ttttccaaaa tcccttatct   3840
tgccttgatc caagtcgaaa aatagggaaa caactcatcc aaaatattcc taattggaca   3900
tttaaaaata aatggtggaa atggtttggg tggaaaaaaa gacgtgctat tgaattgta    3960
catcgcgtag gaattaaaga tcatcgtgat attatggcaa gctatcctaa cgaactgaca   4020
gaaggcgaag gacaaaaagt tatgatcgca atggctgtcg ctaatcagcc acgtttatta   4080
atcgcagatg aaccaacaaa tacattagaa tcaaccactg ccctacaagt ttttcgttta   4140
cttttccagta tgaaccaaaa tcagggaaca acaattttac ttacgagtaa cgatattaaa   4200
agtattagtg aatggtgcga tcaaatttca gtgctttatt gtgggcaaaa taccgaatct   4260
gcccgactg aaatattaat cgaaagtccc catcatcctt atacccaagc cttaattaat   4320
gcagtacccg attttactca acctttgggg tttaaaacta aattgggtac gttagaaggc   4380
accgcgccta ttttagagca aatgccaatt ggctgtcgtc ttggcccaag atgcccttt    4440
gcacaaaaaa aatgtatgga aaaccaaga cgattgaaaa taaacaaca cgaattttct    4500
tgtcattatc ctattaattt acgagaaaaa aatttcaaag aaaaaacaac cgccaccct    4560
tttatactta attgcaaagg aaatgaataa tgcccttatt acaagtggaa gatttaacta   4620
aaacttttaa aggtcacgcc agtttatttg gtcgaaatca attcaatgca gtggataaag   4680
tgagttttac ccttgaacgt aaacaaacac ttgcaatcat tggcaataat ggctctggta   4740
aatcaactct agtgaaaatg atagcgggca ttattccgcc aacttctggt cgaatttttat   4800
ttaatgatcg agaattacaa tatcaggatg cccaatctag agctaaacat attcgtatgg   4860
ttttccaaga tgccaactct gcattttaatc cacgttaaaa tattggacaa atattagacg   4920
aaccattaag cctagcgaca gattggacag aaacacaacg taatgaaaaa atctttgaga   4980
ccctctctct tgttggactt tatcctgatt acacaaatct caatattaag catctctcta   5040
tcagccaaaa gcagcgggtt gccctagcac gcgcattaat tttagcacca gaaattatta   5100
taatagatga tgcaattggc aatttagatg cttctgtacg tattcaattg cttaatttaa   5160
cccttgattt acaacaacgt ttaggtatat cttatattta tgtgggacag gatctcggtg   5220
taattaaaca tattgcagat acgattatcg taatggatga cggaaaaatg attgaatatg   5280
gcagccctca aaatcttttt actgatccac aaactgatgt tactcgtcgc ttagtcgaaa   5340
gctatttgg caaaattta gatgaaaccg cttgggtaaa agacaaaaac actcactaag   5400
```

-continued

```
gaaaggaaaa atgaacactc gtcccttttta tttcggactt atatttattg cgattatcgc    5460
tatacttgct cactatttag gaaacactga ttttttcccat cattatcata tcagtgctct    5520
aattattgcc atcttgctgg gaatggcaat cggcaatacc attatccgc aattttcaac     5580 acaagtggaa aaggcgtgt tatttgcgaa aggcacgctt cttcgcactg cattgtgct     5640 gtatggtttt cgccttactt ttggcgatat tgccgatgtt ggcttaaatg ctgttgtcac    5700
tgatgcgatt atgctaattt caacctttt tcttaccgca cttttgggca ttcgttatct     5760
aaaaatggat aaacaattgg tttatctcac tggggctgga tgtagtattt gtggtgcggc    5820
agcggttatg gcggcagagc ctgttaccaa agcagaatct cataaagttt cagtagcgat    5880
tgccgtagtg gtcattttcg ggacgcttgc tatttttact taccccttgt tctacacgtg    5940
gtcacaagat ttaattaacg cccatcaatt cggtatttat gttggttcta gtgtacacga    6000
agtggctcaa gtatatgcga ttggggaaaa tattgatcct atcgtggcga atactgccgt    6060
catttccaaa atgatccgag tgatgatgct cgcaccattt ttattaatgc tttcttggtt    6120
attaacacgt agtaatggag tatcagaaaa tacatcacac aaaattacaa ttccttggtt    6180
tgctgtactt tttattggcg ttgcgatttt taattctttt gatttattac caaaagaact    6240
cgtgaaatta ttagttgaaa tcgattcttt cttattaatt tcagcgatgg ctgcccttgg    6300
cttaacgaca caagcaagcg caatcaaaaa ggcaggatta aaaccacttg ttttaggaac    6360
actaatttat ttatggctaa tggttggtgg attttttagtg aattatggaa tatcaaaatt    6420
aatataa                                                               6427
```

<210> SEQ ID NO 14
<211> LENGTH: 1013
<212> TYPE: PRT
<213> ORGANISM: H. influenzae

<400> SEQUENCE: 14

```
Met Thr Asn Phe Lys Phe Ser Leu Leu Ala Cys Ser Ile Ala Phe Ala
1               5                   10                  15

Leu Asn Ala Ser Thr Ala Tyr Ala Ala Gln Pro Thr Asn Gln Pro Thr
            20                  25                  30

Asn Gln Pro Thr Asn Gln Pro Thr Asn Gln Pro Thr Asn Gln Pro Thr
        35                  40                  45

Asn Gln Pro Thr Asn Gln Pro Thr Asn Gln Asp Ser Asn Leu Ser Glu
    50                  55                  60

Gln Leu Glu Gln Ile Asn Val Ser Gly Ser Thr Glu Asn Ser Asp Ser
65                  70                  75                  80

Lys Thr Pro Pro Lys Ile Ala Glu Thr Val Lys Thr Ala Lys Thr Leu
                85                  90                  95

Glu Arg Glu Gln Ala Asn Asn Ile Lys Asp Ile Val Lys Tyr Glu Thr
            100                 105                 110

Gly Val Thr Val Val Glu Ala Gly Arg Phe Gly Gln Ser Gly Phe Ala
        115                 120                 125

Ile Arg Gly Val Asp Glu Asn Arg Val Ala Ile Asn Ile Asp Gly Leu
    130                 135                 140

Arg Gln Ala Glu Thr Leu Ser Ser Gln Gly Phe Lys Glu Leu Phe Glu
145                 150                 155                 160

Gly Tyr Gly Asn Phe Asn Asn Thr Arg Asn Gly Ala Glu Ile Glu Thr
                165                 170                 175

Leu Lys Glu Val Asn Ile Thr Lys Gly Ala Asn Ser Ile Lys Ser Gly
```

```
                180              185              190
Ser Gly Ser Leu Gly Ser Val Ile Tyr Lys Thr Lys Asp Ala Arg
        195              200              205

Asp Tyr Leu Leu Asn Lys Asp Tyr Tyr Val Ser Tyr Lys Lys Gly Tyr
    210              215              220

Ala Thr Glu Asn Asn Gln Ser Phe Asn Thr Leu Thr Leu Ala Gly Arg
225              230              235              240

Tyr Lys Lys Phe Asp Val Leu Val Val Thr Thr Ser Arg Asn Gly His
                245              250              255

Glu Leu Glu Asn Tyr Gly Tyr Lys Asn Tyr Asn Asp Lys Ile Gln Gly
            260              265              270

Lys Arg Arg Glu Lys Ala Asp Pro Tyr Lys Ile Glu Gln Asp Ser Thr
                275              280              285

Leu Leu Lys Leu Ser Phe Asn Pro Thr Glu Asn His Arg Phe Thr Leu
    290              295              300

Ala Ala Asp Leu Tyr Glu His Arg Ser Arg Gly Gln Asp Leu Ser Tyr
305              310              315              320

Thr Leu Lys Tyr Leu Lys Thr Leu Pro Asp Leu Pro Glu Val Asp Ser
                325              330              335

Arg His Thr Asn Asp Lys Thr Lys Arg His Asn Ile Ser Phe Ser Tyr
            340              345              350

Glu Asn Phe Ser Gln Thr Pro Phe Trp Asp Thr Leu Lys Ile Thr Phe
        355              360              365

Ser Lys Gln Lys Ile Lys Thr Arg Ala Arg Thr Asp Glu Tyr Cys Asp
    370              375              380

Ala Gly Val Arg Tyr Cys Glu Gly Thr Ala Asn Pro Ala Gly Leu Lys
385              390              395              400

Leu Lys Asn Gly Glu Ile Thr Arg Arg Asp Gly Thr Pro Leu Gln Phe
                405              410              415

Lys Glu Ile Asn Asn Thr Thr Pro Asn Ser Asn Ser Asn Lys Asp
            420              425              430

Lys Thr Tyr Asp Phe Ser Lys Leu Ile Asp Thr Asn Gly Lys Glu Ile
        435              440              445

Glu Ser Gly Ile Thr Arg Ser Asn Asp Thr Phe Trp Tyr Asp Cys Ser
    450              455              460

Ile Phe Asp Cys Glu Asn Pro Gly Lys Met Lys Val Ala Glu Gly Lys
465              470              475              480

Thr Tyr Tyr Arg Tyr Asp Gly Thr Trp Lys Asn Asn Val Gln Leu Glu
                485              490              495

Lys Lys Val Leu Asn Gly Lys Glu Phe Ala Arg Ile Asn Asn Gly Thr
            500              505              510

Arg Gly Lys Thr Phe Pro Ile Leu Pro Ser Ser Leu Gly Tyr Leu Glu
        515              520              525

Arg Leu Trp Gln Glu Arg Asp Leu Asp Thr Asn Thr Gln Gln Leu Asn
    530              535              540

Leu Asp Leu Thr Lys Asp Phe Lys Thr Trp Arg Val Glu His Asn Leu
545              550              555              560

Gln Tyr Gly Ser Ser Tyr Asn Thr Thr Met Lys Arg Met Val Asn Arg
                565              570              575

Ala Gly Tyr Asp Ala Thr Asp Val Gln Trp Trp Ala Lys Arg Thr Leu
            580              585              590

Gly Thr Arg Phe Asp Phe Leu Lys Asn Glu Glu Ile Val Glu Thr Cys
        595              600              605
```

```
Ala Thr Thr Phe Gly Trp Asn Ala Phe Leu Cys Pro Arg Val Asp Pro
    610                 615                 620

Glu Phe Ser Tyr Leu Leu Pro Ile Lys Thr Lys Glu Lys Ser Val Tyr
625                 630                 635                 640

Leu Phe Asp Asn Val Val Ile Thr Asp Tyr Leu Ser Phe Asp Leu Gly
                645                 650                 655

Tyr Arg Tyr Asp Asn Ile His Tyr Gln Pro Lys Tyr Lys His Gly Val
            660                 665                 670

Thr Pro Lys Leu Pro Asp Asp Ile Val Lys Glu Leu Phe Ile Pro Leu
        675                 680                 685

Lys Ser Gly Gln Asn Asn Asp Ala Glu Val Lys Lys Asn Val Gln
690                 695                 700

Glu Asn Ile Asp Tyr Ile Ala Lys Gln Asn Lys Lys Tyr Lys Ala His
705                 710                 715                 720

Ser Tyr Ser Phe Val Ser Thr Ile Asp Pro Thr Ser Phe Leu Arg Leu
                725                 730                 735

Gln Leu Lys Tyr Ser Lys Gly Phe Arg Ala Pro Thr Ser Asp Glu Met
            740                 745                 750

Tyr Phe Thr Phe Lys His Pro Asp Phe Thr Ile Leu Pro Asn Thr His
        755                 760                 765

Leu Lys Pro Glu Ile Ala Lys Thr Lys Glu Ile Ala Phe Thr Leu His
770                 775                 780

His Asp Asp Trp Gly Phe Ile Ser Thr Ser Leu Phe Lys Thr Asn Tyr
785                 790                 795                 800

Arg Asp Phe Ile Asp Leu Val Tyr Lys Gly Glu Arg Glu Phe Glu Val
                805                 810                 815

Gly Asn Pro Asn Asn Arg Gly Lys Ile Ser Phe Asp Thr Phe Gln Asn
            820                 825                 830

Ile Asn Arg Asp Ser Ala Val Val Lys Gly Ile Glu Ile Asn Ser Lys
        835                 840                 845

Val Phe Leu Gly Lys Met Ala Lys Phe Met Asp Gly Phe Asn Leu Ser
850                 855                 860

Tyr Lys Tyr Thr Tyr Gln Lys Gly Arg Met Asp Gly Asn Ile Pro Met
865                 870                 875                 880

Asn Ala Ile Gln Pro Lys Thr Met Val Tyr Gly Leu Gly Tyr Asp His
                885                 890                 895

Pro Ser Gln Lys Phe Gly Phe Asn Phe Tyr Thr Thr His Val Ala Ser
            900                 905                 910

Lys Asn Pro Glu Asp Thr Tyr Asp Ile Tyr Ala Lys Asp Lys Asn Gln
        915                 920                 925

Thr Asn Thr Ser Ile Lys Trp Arg Ser Lys Ser Tyr Thr Ile Leu Asp
930                 935                 940

Leu Ile Gly Tyr Val Gln Pro Ile Lys Asn Leu Thr Ile Arg Ala Gly
945                 950                 955                 960

Val Tyr Asn Leu Thr Asn Arg Lys Tyr Ile Thr Trp Asp Ser Ala Arg
                965                 970                 975

Ser Ile Arg Ser Phe Gly Thr Ser Asn Val Ile Asp Gln Lys Thr Gly
            980                 985                 990

Gln Gly Ile Asn Arg Phe Tyr Ala  Pro Gly Arg Asn Tyr  Lys Met Ser
        995                 1000                1005

Val Gln  Phe Glu Phe
    1010
```

<210> SEQ ID NO 15
<211> LENGTH: 6125
<212> TYPE: DNA
<213> ORGANISM: H. influenzae
<220> FEATURE:
<221> NAME/KEY: misc_feature
<222> LOCATION: (6098)..(6098)
<223> OTHER INFORMATION: n = a, c, g, or t
<220> FEATURE:
<221> NAME/KEY: misc_feature
<222> LOCATION: (6110)..(6110)
<223> OTHER INFORMATION: n = a, c, g, or t
<220> FEATURE:
<221> NAME/KEY: misc_feature
<222> LOCATION: (6115)..(6115)
<223> OTHER INFORMATION: n = a, c, g, or t

<400> SEQUENCE: 15

```
tgcagattcc ggtatttgcc ccccaataaa ggcactgaaa ttttgatcgc cccattcact      60
aatactttta atatcgttac tcgtaagtaa aattgttgtt ccctgatttg gttcatactg     120
gaaagtaacc aaaacctgtg acggcagggg tgattccaaa ggtattgttg ggtcatccgc     180
gaatataaac gtgggcggat tagcgacagc cattgcgatc aaaccttttt gtccttcgcc     240
ttctgtcagt tcgttaggat agcttgccat aatatcacga tgatctttaa ttcctacgcg     300
atgtaacaat tcaatagcac gtctttttt ccacccaaac catttccacc atttattttt     360
aaatgtccaa ttaggaatat tttggatgag ttgtttccct attttcgac ttggatcaag      420
gcaagataag ggattttgga aaatcatgga tatttctttg ccgacaatct tacgtcgttt     480
attaggactg agttttagta attcgatatc gtgaaaacga aagcgatcgg cagtaataat     540
ccaattttct ttgattgcat tacaaatgac tttagcgatt aagctttttc ctgagcctga     600
ttcgccaact aatccactga ttccccttc gttaagggaa agattgacgc catctacaat      660
ttttatacgt ccattggagg tttgaatttc aatattgagg ttacaaatgt ctaaaagtgc     720
cataggctat tcttgatgtt gattgatggc tttagttaag ccattactga aaataatact     780
taataaaata gtaaaaataa tagcgaaacc gggtaaaagt actgtccaag gtgcaagata     840
aagtagttcc aaagagtctt ttatcattgc cccccattct ggtgtaggtc gttgtgcacc     900
aagagaaata aaacttaatg cgctaatatc aacacggct ataacaaaag catgagccac      960
ttcttgaata taaataacag taatattcgg taaaatagtg ctttttaata aggtttgatt    1020
ggaaatgcct tcaagtttta gcattacaac ataatccttt tctaattctt tttgaatagc    1080
gcgatagata gtgtgaaatg aaataaggca aaattgctaa tagcgtagca aacattgcat    1140
tccataaact tggttccatt aatggttgaa ataacaacgg caattaatag aataggtaac    1200
gataaaaaag catcaaaaat atgcccgaca aaacgagctt taatacctt cagtagtcct     1260
gcaataattc ctagtgcgcc gcctattatt gccactgaaa agacaaccag taaagcagaa    1320
cctaaggtat aacgagtacc cataattaaa cgacttaata tgtcgcgacc tatatcatca    1380
gtaccaaaga aaaagcaat ttttcctcta tctacccaag aaggaggcat taattcttgc     1440
ccaataaatt gtcgattatc agcataaggt gcaagataac tagcaaaaag tgcggtaaaa    1500
attaatgcga ttaataaata aaagctaaaa agtgcgatgg tattttgacg aaagcgtaac    1560
caaatttgaa agattgaggt gctttcgcgg aattcatcag gttctttatc ttgcatacca    1620
acctttcttt ttaaatggat cgagtataaa agtgaatatt ttagtgaatg tatcaatcaa    1680
aataatacat acaccaataa caattacacc tgcggcaatg ctgttgtaat cttgttcatt    1740
tacggcatta attaaccaac gaccaatgcc aggccaacct aaagccgttt ctaccaacat    1800
```

-continued

```
acattgcgtt aatactaatg tgaatacacg tggtacttgt ggaacaagca ggggaaaagt      1860
attacggaat acatattgat ggagaatttt ccattttgac caaccccgtg ttgtcgctac      1920
tttagaaaaa ttttgattca aaatatattc tgctcgttga tgaataatac ggataatttc      1980
cattgttggc aaaatacaca ataccaatgt tggtaaggct aaatgttgca atatgttttg      2040
tacgattttt gtacgataag gtacttccat aaaccacata tcaataacag gaaatcccgt      2100
aatgggttta atttcgtaaa gcaaattata ttgtccaata gcggcaattt cccaatgtga      2160
gagcgcggca acatacagta aaatgggggc taaccaaaat attggaatag atagccctac      2220
ataagatagg atttgtaaac tttttgcaaa aacttgttca gaattgaccg cacttataat      2280
gccaagtggc aaaccaaaaa taatgccaa aaacaatgta atgaaacaaa gttccaatgt      2340
gggaggaaga accgtaagaa taaggttcat taatgatttt ccaccgttat aggtaatgcc      2400
aaaatcacct tgtaacaagg tgcctaaata atggaaatag ccgatataaa tgttttgtgt      2460
aacaagattc gcattaagag gatcgcgcaa taaaataaca aagcctaata gcgataatac      2520
gagtaataat aatgccaccc acagaatatg gcgaagaacc gaccagaaca ttagtgtttc      2580
tcctgaataa aataaaggt ggaaaaatct aagctaccaa aaggcgtcat ttttactcct      2640
ttcacacgac tatttgcgac taaaattcgt tttacattgg caataggaat aatgggtaat      2700
tcacgtagaa cgagttcttg ggcttcatta taggcttttg cgcgtgaact taaatgtgag      2760
gtggtaatgg cacgatccat aaaattgatca aattcttcat tacaccaatt agataaatta      2820
gtgagttcat tttttgttcc acagcttaaa attggacgca taaaaccatc aggatcaaga      2880
ttaccagcta accaaccaga tagaatcaaa tcataatttt ccgattgatt gcgtaattgt      2940
gcagttaaaa atggacgagt tacggcacgc acttttaactt tcacacccgc ttgagctaaa      3000
tcccatttga tcatttcagc catttttaaaa ggtgctggat tatagacttg ttcttcatta      3060
attacccata aatttaacaa aaggttttta tctgctaatt tatttttggc gattttggga      3120
tggtaatcaa actcaaattc tggcgtattg acagttgaag cccaagacac ttcaggaata      3180
atgttattag caacagttgc tgtgttatgg taaatgctat gaatgattcg agctcggttt      3240
aaactttgtg aaatagcagc acggatttcg tgatctcgca ttaatggctt atcaaaatta      3300
aacgctaaat aggctaaatt cataccatca gtagattgca tataataatg tttgtcatca      3360
ttttttaata agccaatttg gcttacttca ggataagagg cgatttgaca ttcattattg      3420
aaaaatttga ctaaacgtcc gctgcgatca gtagaaagat ccacaataat atgttctatc      3480
ttggcttctt ttttccaata gttttcgtta cgcactaagc gaacatattg gttatataca      3540
taatctttta cttgataagg ccctgtgcct actgggtggg tatctaattg agcaaggttg      3600
tcatctgcgc ttaattgata ggcatattct tgtgaaaaaa taatggcata ctggctggca      3660
agatgcgaca aaatggagga atctggtgca aataattcaa ttttttacttg ataaggcgaa      3720
agtgcggtca cagatttgat tttttcgtta agtttaatgc tatcaaaata aggaaaacgc      3780
acttttcttg cttgttcgtg aaacactcta tattgtggat tactataggt aacattcgcc      3840
tctgctaagg ttggtaaata agtattatgc cctaatacac gattaatcga aaatactacg      3900
tcttcagcgt taaatacacg tgttggggta accaagggg tttggtgaaa ttttacgccg      3960
tgacgtaaat ttaataaaat ttcttttacca tcagctgaaa tggaataaga ttgtgccagc      4020
attggtgtta atgttgcact gtgatttttt atatcaaata atttgttata aatttgttcc      4080
gtgaccacat tcatactggt tcctgcatct gctgtttgcg gattaaatga aaaacctgaa      4140
```

```
gcgtgggtgc aataagttaa gccattttca gttaaaaatg ttggaacact tggcgcagcc    4200
tgtaattcta cactttggct tatacagagc agaaaagata aaaatctcag atttagacgt    4260
aacataacaa atgcattgtg ataaattatg tgtcaaattg taaggcatat tagtaaaaat    4320
ggctaggata ttgaatgttt aatcgggttc aaaaggaaat caatcaaatt attaatcgtg    4380
gttttgatcg cactttgcgt ttagcggtaa cagggttaag tcggagtgga aaaacggcgt    4440
ttattacaag tttaatcaat caacttctct ccattaatca acattcatca cagaatttgc    4500
ccttgtttga agcagcgaga aatggtgcga tcttggcagt caaacgagta tcccaacaag    4560
atctcagcgt gccacgtttt gattatgaaa gtaatttaaa tgatttgtca caaaatccgc    4620
ctcaatggat tcaatctact cgtggcgtga gtgaaacgcg tttagccatt cgttttcaac    4680
gccaatctgg cttgctacgc catttgaaag aacgaggcac gctttatcta gatattttg    4740 attatccagg ggaatggctg atcgatttgc cgttattaaa tctagatttt caacaatggt    4800
cacaagagca aattaaggta acaacaggca ttcgtgaaga attggcggag aattggctcg    4860
ctatgttgca ggatttggat ttaagtgcgg tcgcaaatga agatgtttta gccaagatag    4920
cgaaaagtta tacggattat ttacatcaat gcaaagtgca aggcatgcaa tttattcagc    4980
ctgggcgatt tgtattgccg agtgatttag agggcacgcc cgcattacaa tttttcccat    5040
taattcatct ttcagaagaa cagtggcgaa ccttgaaaaa aacagcaaaa tcaaatagct    5100
attttgctgt gctgacaaaa cgttatgatt attatcgcaa taaaattgtg aaaggttttt    5160
acgaaaatta tttttctacc tttgatcgtc aagttatttt ggcggattgt ttaacgcctt    5220
taaatcacag tcagcaagcc ttttttagata tgcaaatggg cttaaatcag ttatttaata    5280
atttccatta tggcagcaga aattttcttc atcgtttgtt ttctccgcga attgatcgat    5340
taatgtttgt tgcgacaaag gcggatcata ttactcgtga tcaaattcct aatttagtaa    5400
gtttaatgcg ccaaattgtg caagagggtg gtcgccatgt ggaatttgaa ggaatcgata    5460
cggaatatac cgccattgcg gctgttcgta ccacaaagca agtgattgtg aatcagcaag    5520
gaaaagaaat taaagcaatt caaggggttc gttctattga taaacagctg attacacttt    5580
atccgggaac ggtgccgagc aaattaccaa gagcagaatt ttggcaaaaa caaccgcact    5640
ttgattttga tagttttgaa cctcagcctt tagaacaagg ggagagcatt cctcatttga    5700
gaatggatgc ggttttacaa ttttttattaa gtgatcgatt tgaataaaaa gtgcggaaaa    5760
ttttccgcac ttttttcatc tttctagcct gtattgcgca tcccagccgc gatacctgtg    5820
atggtaatca tcaatgcttg ttccacatcg ggattgactt gctctggatt ttcacggaaa    5880
cggtgaagca attccacttg cagtagattg agtggatccg tgtagatatt acgtaatgca    5940
attgaatctg caatccaagg taaatcagac atcaattcac tttggtgaga aagtgaaagc    6000
acagtttgaa tatcatcttc aagttgctta cgtaaatttt cacctaaata ccaaagctct    6060
ttttcactaa tcgttgatca tattgtggga aagggtnac cgaggcccgn aattncggat    6120
accat                                                               6125
```

<210> SEQ ID NO 16  
<211> LENGTH: 3520  
<212> TYPE: DNA  
<213> ORGANISM: H. influenzae  
<220> FEATURE:  
<221> NAME/KEY: misc_feature  
<222> LOCATION: (2522)..(2522)  
<223> OTHER INFORMATION: n = a, c, g, or t  
<220> FEATURE:  
<221> NAME/KEY: misc_feature
<222> LOCATION: (2598)..(2598)
<223> OTHER INFORMATION: n = a, c, g, or t

<400> SEQUENCE: 16

| | | |
|---|---|---:|
| ctttattaag ccaaaaggta aaaaatgaaa attgcattag gcattgagta taacgggcaa | | 60 |
| aattattatg gttggcagag acaagaaaaa gtccgtagtg tacaagaaga attagaaaag | | 120 |
| gcactttctc acattgcaaa tgaaaaaatt gagatatttt gtgcaggcag aacggattct | | 180 |
| ggcgtaagtg gaacgggtca ggttgttcat tttgaaacca atgcggttcg tccagagaag | | 240 |
| gcttgggctt ttggtacgaa tgctcattta cctgatgaca ttgcggtggc ttgggcaaaa | | 300 |
| caagtcgatg atgaatttca cgccagattt tccgcaacag cacgccgtta ccgctatatt | | 360 |
| ctttattgta ataaattacg ctctgcgatt ttagcgggag gaataaccca ttgccattta | | 420 |
| gatttagatg cggaaaaaat gcatcaggca gggcaatgtt tacttggcga acaggatttt | | 480 |
| tcctctttcc gtgcggcaca atgtcagtct catacgcctt ggcgtaatgt gcatcatttg | | 540 |
| aatgtgtctc gtatcggaaa atatattatt gttgatattc aggcgaacgc ttttgtgcat | | 600 |
| catatggtgc gcaatattgt gggaagtttg attgaggtcg gtgctggaaa tcagccgatt | | 660 |
| gaatggatgc aatggctact tgagcagaaa atcgtcagc ttgctgcacc aacagcaaaa | | 720 |
| ccagatggat tgtatttggt tgatgtgatt tatccacaaa agtttgatat tcctaaacgc | | 780 |
| ccgattggtc ctttatttt agaggatggt ttattaaatc gtactttgaa gtaaagcgta | | 840 |
| atttcatgtt ttaaataacc atatctgaaa atattcttca taaaaaaga ccgcacttta | | 900 |
| aaagtgcggt caatcttaag tgagttttat attaattttg atattccata attcactaaa | | 960 |
| aatccaccaa ccattagcca taaataaatt agtgttccta aaacaagtgg ttttaatcct | | 1020 |
| gcctttttga ttgcgcttgc ttgtgtcgtt aagccaaggg cagccatcgc tgaaattaat | | 1080 |
| aagaaagaat cgatttcaac taataatttc acgagttctt ttggtaataa atcaaaagaa | | 1140 |
| ttaaaaatcg caacgccaat aaaaagtaca gcaaaccaag gaattgtaat tttgtgtgat | | 1200 |
| gtattttctg atactccatt actacgtgtt aataaccaag aaagcattaa taaaaatggt | | 1260 |
| gcgagcatca tcactcggat cattttggaa atgacgcga tattcgccac gataggatca | | 1320 |
| atattttccc caatcgcata cacttgagcc acttcgtgta cactagaacc aacataaata | | 1380 |
| ccgaattgat gggcgttaat taaatcttgt gaccacgtgt agaacaaggg gtaagtaaaa | | 1440 |
| atagcaagcg tcccgaaaat gaccactacg gcaatcgcta ctgaaacttt atgagattct | | 1500 |
| gctttggtaa caggctctgc cgccataacc gctgccgcac cacaaatact acatccagcc | | 1560 |
| ccagtgagat aaaccaattg tttatccatt tttagataac gaatgccaa aagtgcggta | | 1620 |
| agaaaaaagg ttgaaattag cataatcgca tcagtgacaa cagcatttaa gccaacatcg | | 1680 |
| gcaatatcgc caaagtaag gcgaaaacca tacagcacaa tgccagtgcg aagaagcgtg | | 1740 |
| cctttcgcaa ataacacgcc tttttccact tgtgttgaaa attgcggata atggtattg | | 1800 |
| ccgattgcca ttcccagcaa gatggcaata attagagcac tgatatgata atgatgggaa | | 1860 |
| aaatcagtgt ttcctaaata gtgagcaagt atagcgataa tcgcaataaa tataagtccg | | 1920 |
| aaataaaagg gacgagtgtt catttttcct ttccttagtg agtgttttg tcttttaccc | | 1980 |
| aagcggtttc atctaaaatt ttgccaaaat agctttcgac taagcgacga gtaacatcag | | 2040 |
| tttgtggatc agtaaaaaga ttttgagggc tgccatattc aatcattttt ccgtcatcca | | 2100 |
| ttacgataat cgtatctgca atatgtttaa ttacaccgag atcctgtccc acataaatat | | 2160 |
| aagatatacc taaacgttgt tgtaaatcaa gggttaaatt aagcaattga atacgtacag | | 2220 |

```
aagcatctaa attgccaatt gcatcatcta ttataataat ttctggtgct aaaattaatg    2280
cgcgtgctag ggcaacccgc tgcttttggc tgatagagag atgcttaata ttgagatttg    2340
tgtaatcagg ataaagtcca acaagagaga gggtctcaaa gattttttca ttacgttgtg    2400
tttctgtcca atctgtcgct aggcttaatg gttcgtctaa tatttgtcca atatttaaac    2460
gtggattaaa tgcagagttg gcatcttgga aaaccatacg aatatgttta gctctagatt    2520
gngcatcctg atattgtaat tctcgatcat taaataaaat tcgacccaga gttggcggaa    2580
taatgcccgc tatcattntc actagaggtg atttaccaga gccattattg ccaatgattg    2640
caagtgtttg tttactgttc aagggtaaaa ctcactttat ccactgcatt gaattgattt    2700
cgaccaaata aactggcgtg acctttaaaa gttttagtta atcttccac ttgtaataag    2760 ggcattattc atttcctttg caattaagta taaaggggt ggcggttgtt ttttctttga    2820
aatttttttc tcggagatta ataggataat gacaagaaaa ttcgtgttgt tttattttca    2880
atcgtcttgg ttttttccata cattttttt gcgcaaaagg gcatcttgga ccaagactat    2940
ctgccttcgg tatttgctct ataacattcc ctgtaccttc ctccgttccc tttttatctt    3000
aaatttcata tctttttttc ttttctattt ctcttttttt ttatttttt acagcgttcc    3060 ctcttgattc accgccccctt atccttccag catgcccggc ttgtattttc atttgcccct    3120
tatcccggtc ttttctgcct gttttttcct tctgttttt cttcccctc ttttctcccc    3180 tctctccggc ctcctcgttc ttttcgcttt tttcccttgc ccatctttt tttcttatct    3240 ttccacatcc ctttgtatat tgttatcttc tctctattct ttccccgtt attctcccgt    3300 tttctttcct cccctccctc cctttcttat tgtttttttt cttttttgtc attttctttt    3360
atttctctct tttcactccg ttatcttttt attttttata tttctcttt ttttttttga    3420 tttcttcttc ttttttgtgt ctattcttat ttttctttt attctttctt ctatccttgg    3480
agtgtttctt attgttacat ttttgtttc ttcctctttt                          3520
```

<210> SEQ ID NO 17
<211> LENGTH: 5562
<212> TYPE: DNA
<213> ORGANISM: H. influenzae

<400> SEQUENCE: 17

```
ccccgctgca gtttgttggc gtaactctgc ttccggcgtt tttgttcctt acgatttga     60 accgaatttt cattatcgcc cactttttcc gaaactttat tttcagatgt gctattttgt    120
tcattcagcc attttgata gtcttctaaa tcgcctttaa attcttccac ttttttatcg    180
tgaactaaat aaaattcttc cacggtattg cgtaataaat gacgatcgtg cgacaccacc    240
accaaagaac cttcgtaatc taccaatgct tccgttaatg cttgacgcat atccaaatcc    300
aaatggttag tcggttcatc aagtagtaat aaattcgggc gttgccaaac aatcaaagcc    360
aacaccaaac gagcttttc tcctccagaa aaagatttca ctgcttgatt tactttatcg    420
ccgtgaaacg caaaactgcc taaataatct cgaacttgtt gctccgtttg ttctggtgcg    480 agttttgca tgccacag agcagattcg tctgcgcgta agtatctaa ttgatgctga    540 gcaaaatagc caagctgcac gccttttgcc aactgcactg tgcctgaaag tgcggtcagt    600
tctcccgcta aagtttaat caaggttgat tttcctgcac catttttccc gagtaaacca    660
atgcgcgaac ctggcactaa attcagttta attttactta aaatttctac cgcactttct    720
ccgctgccat aacctgcact tgcctgttca atcatcacta agggattcgg caaggattgc    780
ggtggacgaa atttaaaagt aaaaggatta tccacataag ctggtgcaat cagctccatt    840
```

```
ctttctagtg ctttcatacg gctttgtgcc tgtttggctt tagtggcttt ggctttaaag      900
cgatcaatat attttttgtaa atgggaaatc ttttgttgtt gctgacgata catcgctgtt      960
tgttgtgcca atttagtggc tcgttgcact tcaaaggaag aataatcgcc cgtgtattcg     1020
ttgagcttct gattttcgat atggaggatt tttgtcacaa tcggatcgag aaaatcacga     1080
tcgtgagaaa ttaataccaa ggtgccttga tattgtacta gccaacgctc taaccaaata     1140
accgcatcca aatccaaatg gttggttggc tcatccagta ataataaatc tgatggacaa     1200
agcagagctt gtgccaaatt caaacggatc cgccaaccgc ccgaaaaggc tttcactggc     1260
tgggttgttt cttcttgact aaatcctaaa ccattcaata acgaagcggc acgagattga     1320
attgtccacg catccaaggt ttctaattgc ccgtgaatac gtgcaatggc gttaccgtca     1380
ttgcattcat ttgcttgttc aagctcttgt tgcaaacggc aatattcacg atccccttga     1440
attacataat caattgcaga aatatccaat gcaggcgttt cttgattcac ccaagatacc     1500
cgccaatttg ctggataatt tacctcgccg ccctctggcg ttaattcttt ttttaataag     1560
gcaaaaagcg aagattttcc acaaccattt tcccccacca agccgacttt ttgcttagga     1620
ttaatggtag cagaagcatt tcgagaagc tccgtttgcc ctcgttttaa ggacagatta     1680
ctaaatacaa tcattttttct acaataggtc ttaatttgag gctatttttgc aatattttt     1740
cttttctcgg aacagtctat tccgatttta tcgattttct agtcaaaaaa gccaggtata     1800
ataaggtgca ataaaaacta tttattgaga aaacttaatg aaaatataac aagtcaatat     1860
gaaaataatg ggtatatctt aggcatttt taccctttaga ggcacaatcg acagggtttt     1920
ccctaaagga gcgagcaatt ttaacaacgt ttcaagttga ggattcgttt gtccttttc     1980
aatgcgtgca atcataggtt gcttcacacc gcttaaggtt tcaagttgtt tttgggaaat     2040
cccaagttgc tggcgagaag taatcaattc tttaattaag gctacacgta aattactttc     2100
gcggatttct tcttcattga aaatttgctg ttcaaactca ttccaatttg aacctaatgg     2160
gctgattta ttcattttttc aatctctctt ttaattcact taagcgttgt tgggttgttt     2220
ggattacata atctcgaatt ttattcagtt taattcgact atctttgctt tcattttgag     2280
ccagcgatag cagatattct ttcactggct caatgtcatt ttggtctctg taaaagagaa     2340
tctcgtacat aatttatcct atttacttat ttatttcaat aactaataag ttattgatt     2400
ttgatgtgta agcataaata gaaactaaaa atttggcgag atagtcattt caatcttttcg     2460
atcgagatcg caaaaatagc aaaaagaggt tgattttcaa ggagattttg cacaaatgcc     2520
gatgtttgaa cattagcttt gaaagagaga gtaaaggta gatcctttct taagaaaaag     2580
tgcggtaaaa atttaccgca cttttgattt tagacaggtt taaaactcaa attgaactga     2640
catcttataa tttctacctg gtgcgtagaa gcggttaatg ccttgacctg tcttttgatc     2700
tataacatta cttgtaccaa atgaacgaat tgaacgcgca gaatcccaag tgatgtattt     2760
acggtttgta agattatata cgccggctct tatggttaaa ttttttaattg gttgcacata     2820
tccaattaaa tctagaatag tataagattt actgcgccat tttatgctag tgttggtttg     2880
gttttttatct ttcgcataaa tatcataagt atcttctgga tttttacttg ctacgtgggt     2940
agtgtagaaa ttaaatccaa attttttggct tgggtggtca tagcctaagc catacaccat     3000
cgttttaggc tgaattgcat tcataggaat attgccatcc attcttcctt tttgataggt     3060
atatttatag cttaggttaa atccatccat aaatttgcc attttaccaa ggaatacttt     3120
tgaattaatt tctattcctt ttactaccgc actatctcta ttaatatttt gataaagaga     3180
```

```
aaatggtaat gtgctacctc cgctaactaa tttaaaatct ttttctcctt taaatattag    3240
gtcgataaag ttttatagt tggttttaaa tagacttgtg gagataaaac cccaatcatc    3300
attatgtaat gtaaaagcaa tttcttttgt ttttgctatc tctggtttta gattagtatt    3360
tggcaaaata gtgaaatcag ggtgtttaaa ggtgaaatac atttcatctg aagttggtgc    3420
tctaaaacct tttgaatatt ttagttgtaa acgaagaaaa ctcgttggat caatcgttga    3480
aacaaaactg taagaatgtg ctttatattt tttgttttgt ttagcgatat agtcaatatt    3540
ttgttgtacg tttttcttaa cttcaggatc atcattatta tttttaccac ttggtaatgg    3600
aataaacaat cctttcacaa tatcatcagg taatttcggt gtaacgccgt gtttatattt    3660
tggttgataa tggatattgt cataacgata acccaaatca aaagataaat aatcagttat    3720
aacaacatta tcaaagagat agactgattt ttcttttgtt ttaatgggta ataagaatga    3780
aaatttagga tcaactcgag ggcaaaggtt agctttccac cccccataag cggttttaca    3840
agtgtgaggt ttatcataca acaaactgta accaagtgta ggctctgccc accattgcac    3900
atcagaagca tcattaccag cacgattaac cattcgcttc atcgttgtat tatatgagct    3960
accatattgt agattatgtt caacacgcca agttttgaag tctttggtta aatctaaatt    4020
taattgttgg gtgttggtgt ctaaatctcg ctcttgccag aggcgttcta ataacctgg    4080 agatgaggga agaatagagt atgttttatt attcgcatcc tttactctag cgaaattttt    4140
gtcatttaat tcttttattt caagttcaaa gtctttttc cacgttccag tagtgccata    4200
gccataaaga tgttcagttt caaaaaattt tcatttttg gttttatctt tacaatcaaa    4260
atattgaaac aatcatacca agttccagag gatctccttt aggcctagtt taacctctat    4320
tactcgatca tcagtatcaa taaatttatc gaagtcctag atgctggtat caatatttta    4380 acttttttt caaatgaagt tctgaacatc tccgcggggt tatttcccat ctgttatttt    4440
tagtcccgca ggatttgcag ttccctcaca atatcttaca cctgcatcac aatagtcatc    4500
tgtacgtgcg cgagttttaa tacgttgatc tgaataagtg atttttaatg tatcccaaaa    4560
tggcgtttga gagaaatttt catagctaaa ggaaatatta cgtctctttg ttttatcatt    4620
ggtgtgtcta gaatcaacct cgagtaaatt aggatctgtt ttttgatatt ttagtgtata    4680
ggataaatct tgcccacgag aacgatgttc atataaatct gctgcaaggg taaaacgatg    4740
attttctgta gggttaaaag ataatttaa taatgtacta tcttgttcaa ttttgtatgg    4800
gtctgctttt tctcttttt taccttgagt aaggctattt gcattttgt aatcatagtt    4860 ttcaagttcg tgtccatttc tgcttgttgt aaccactaag gcatcaaact ttttataacg    4920
tcctgcaaga gtaagggtat tgaatgattg attatttct gtagcgtatc ccttttgta    4980 gcttacatag taatccttgt taaggagata atctctcgca tcttttgttt tataaattac    5040
agatccacct aaggaaccac taccactttt gattgaattt gcccctttg taatatttac    5100 ttctttaaa gtttcaattt ctgcaccatt acgcgtatta ttgaagttac ataaccctc    5160 aaaaagctct ttaaagcctt gagaagatag ggtttcagct tgacgtaatc catcaatatt    5220
aatcgctaca cggttttcat ctacaccacg aatggcaaaa ccgctttgcc caaaacgccc    5280
agcttcaaca acagtaacgc ccgtctcgta tttaacgatg cctttaatat tggtttgttt    5340
gttccttttc catcgtttta acctcgtttt accgttcttt tatattctcc gtcggctctt    5400
ttctattctc gtcttcttgc cgcaccgcta cgtcgatttc ctcttatctt tctataattc    5460
ttatttctct tgtctttct tgtctctcat ctatactact tctcatactc ttttttgcttt    5520 cttcacctcc tcttttccacc ctttgcctta aagcacccctt ta                    5562
```

```
<210> SEQ ID NO 18
<211> LENGTH: 3318
<212> TYPE: DNA
<213> ORGANISM: H. influenzae
<220> FEATURE:
<221> NAME/KEY: misc_feature
<222> LOCATION: (3281)..(3281)
<223> OTHER INFORMATION: n = a, c, g, or t
<220> FEATURE:
<221> NAME/KEY: misc_feature
<222> LOCATION: (3291)..(3291)
<223> OTHER INFORMATION: n = a, c, g, or t

<400> SEQUENCE: 18
gagaccccgg gctaagcccc caaaatatca cgattgtttg ttggtgggct aaagcccact      60
ctacaactac taatcaacaa tcaacggctc gcattatagg aaacaagcag gtttaaatac     120
agaaaataat aagaatagtt tttatttctt gattttatc aaaaatcaat ctttattgtt     180
gtgagaaaat gcttcctcgt ataatatatt tgagaattat tattattttt ttataggatt    240
aaatatgacc aattttagat taaacgtgct tgcctattcc gttatgcttg ggctaacggc     300
aagtgttgct tatgcagagc caaccaacca accaaccaac caaccaacca accaaccaac     360
caaccaacca accaaccaac caaccaaaat agtaatgctt ctgaacaact agaacaaata     420
aatgtatctg gctctaccga aaatactgat acgaaaactc cgccaaaaat tgccgaaact     480
gtaaaaacgg ctaaaacgct agaaagagaa caagcaaaca acattaaaga catcgttaaa     540
tacgagactg gcgttactgt tgttgaagct gggcgttttg gtcaaagcgg ttttgcgatt     600
agagggtag atgaaaatcg tgttgcaatt acggttgatg cgttgctca agcagaacat      660
tatcttccca aggttttaaa gacctgtttg aaggatatgg taattttaat aacacgcgta     720
atggaattga aattgaaact ttatctgatg ccaaaattac caaggtgca gattctctca     780
tgtctggtag tggtgcattg ggtggctccg tcatctataa aactaaagat gcaagagatc     840
ttctgcttaa caaaaactac gcgtttaaat ataaaactgg ttttaccagc gagaatgatg    900
aaagattaaa ttctattact tttgcaggaa agcaagtat attcgatgta cttgctgtcg     960
gcacttggcg taatggtcat gaaatcaaaa attatgatta caaatctgca gacgacattc    1020
taggaaaact cagagaaaag accgatcctt ataataaaaa agaccgcagt cttttattga    1080
aaattggtac aaatcttggt gaaaataatc gcattgccgt agcctatgat agaagacggg    1140
ttgaaaataa aggtctagac aaatcttact cattacatgg atgcacgaaa tatgtttgtg    1200
atgataatga aatagatact cgccatactc atgatgaaag cattagaacc agtaaatcta    1260
tagcatttga aaatacaaat ataaacccac tttgggatac cctaaaactc tcttatacag    1320
atcaaagtat tactcaacga gcaagaagtg acgaacattg tgatggtgaa cggtgtcctg    1380
gggtacaaaa ccccatagga ctacattata caacgataa taaacttgtt gataaaaata    1440
ataatcctgt aacctataaa ttagaaaatc gttctgtaac atactattct tacattgatg    1500
aatctatctt taatcgatac agtaacttta agaagaagt tcctgtagaa ctcgctaagg    1560
aatggaaact taagaatat ggtggaaaat attatattga ctcgcctcgc tgctttaaaa    1620
atcacggtga tgctaatcac gagggatgt gtagactaag atctgatgta aaagaggaaa    1680
aggaaacatt agtagctaat aacatcactt atgatttaaa aaaggagtat tttattaact    1740
caaggctcac gaatagtgat aatttattat cttgtgatgg aattaactgt gataaaggta    1800
caattcaagg tttcgaagct gatggaacgc ctaaggattt accaataaaa ataatcccaa    1860
```

```
aagaaggtaa aaaatttgca cttattgaaa aaatttcaga tcaaaatggc tacaatattg   1920
gcccagagaa agcatctcgt tttctagtac ctaattcacc tggttataat agaaacattt   1980
ggaaaaaacg tgaccttgat actcgtactc aacaaattaa tttggattta acaaaacatt   2040
ttgaactagg aaaagccaa catgattat cttatggttt agtttggagt aaaacaacaa    2100
aatcaatgat aaataaagaa gggttaaaag ttaatagtgg aaaatggtgg attgattatc   2160
caaaagactg tgaatctagt acatcagatt tatgtacaaa aaatagtaca gcatcatttc   2220
ttattcctgt agaaacaaaa gatggttctc tctattttaa agatgaattt agagtaaatg   2280
atcgtcttgg cttagatatc ggttatcgat atgacaaagt caaatacaaa accaattatc   2340
aaccgggtat aacgccaaaa atccctgatg atatgttagt taatttattt ataaaagaac   2400
cttttgtaaa aaacacacgg agtctaaacc ctaatgatcc aaatgaaatt aatcgacgaa   2460
aaaatgcaga agctaatatt aattatattt ctcaacccaa aaaatttaat gcgagttctt   2520
atgctttaag cacaaaattc gatccattgg attggttaca agttcaagca aaatatagca   2580
aaggtttcag agcaccaaca gctgatgaat tatacttcac attcaagcac ccagaattta   2640
ctgttcttcc aggctctaaa ttaaaacctg aaattgcaaa aactaaggaa ttatcattaa   2700
ctttacatga tgatgaaatc ggttttatt ctggtggata tttcatcaca aattataata    2760 atttattga ttttagttat ctaggaacaa atcatttgg ttctcaagca actaagcatg      2820
aattatatca atctgttaat ttagataatg ctaaagtgac aggatttgaa ttgaaaacca   2880
aatttacatt aggaaaatgg atatcatggt tgaagaatgt tgattttggt taccaattaa   2940
ctaaacaaaa aggtaaagca agcgataacc gcccacttaa tgctattcag ccaatgacac   3000
aagtgatgag tttagcctat acgcatcctg ataatctgtt tggggcaaat ttatatctta   3060
ctcatgtttc ccaaaaagaa gcgagtgaca catataacat ttattcaaaa gatgctacag   3120
caggagataa agaatatgtt caaaataaac atattaaatg gcgtagtaaa gcttacacag   3180
tgacagattt tactttcttc gtgaaaccta tgaagaattt aactttacga gcgggtgttt   3240
acaatttatt tgacaaaaaa tatagacttg ggatgggat nctatagagt ncgacctggc    3300
aggcatgcat agtctggc                                                 3318
```

<210> SEQ ID NO 19
<211> LENGTH: 3494
<212> TYPE: DNA
<213> ORGANISM: H. influenzae

<400> SEQUENCE: 19

```
ggcattcttg ctgcctgcag ttcactctat gagaccccct tcttatggtg gtcaataatg    60
tcagtaatat aagccattaa aagtaagctc ttcaaaacaa tttgtaagag atttaactga   120
tttagctaaa cgctcccca atgtgttaat tggctcaaaa tacattactg caatatactg   180
tttattaaat cgtttacctt tacccgaaaa ctaccaagat cacgcattag taggagagtg   240
gaaaggttat cgagattgcc atattcaagg caatttggta ctgatttacc aatacgttat   300
acacgatgaa tttgatgaat tgaaattttc tcgtttaaat acacactcac aaaccgcttt   360
aaaatagaag taatcttaaa taataatccg cacgtaaaat gtgcggatta ttttacata    420 ggattaaaat tcaaactgaa cagacattct gtaatttctg ccaggtgcat aaaagcggtt   480
taagccttca ccagtttctg ttttttactcg gttaattgtg ccaagatgtc gaacagagcg   540
agcagagtcc caagtgagat attttttgtt ggttaaatta tatacaccag cggtaaatgt   600
aagattttta attggtttcc aataggcaat cgtatcgatc actgtatagc gattattacg   660
```

-continued

```
ccataatccg cgagaatctt ttacatcttt gccgtttgct tttgtagcag gtatatctgt      720
tgcattgtca gtatattgct tttctttttct ggcgaccata cttgtccatt gagaattaaa     780
gctatctttt gctttttttg ctgcaacatt agtgatatac atatccacgc cccatttttg      840
gcttggtgca tcatagccaa tattgtatac cgatgtggtt ggttgtaagg cattcattgg      900
ttgaggttta cgagcaatgg cttcgtattc tggatgttca tctttattca attccaaaaa     960
ttctttatat tttggatgta atccattgtc tttgattctg ccttttttgat aggtaaattt     1020 atagcctaaa tggaaacctt gtagttttttc aaataaatcg cccatctcaa gacgtgaagc    1080
aatttcgata cctctgactc ttgctcgatc tcgattttgg ttttgatgga acggatattt     1140
tattgcagag ccttcttcaa taggacgttc gcccacttct actaagtcaa taaaattacg     1200
gtaatcgttt tgaaacgcat ttaacgtaat ataactactg tttttataaa aagtgaacgc     1260
gacttctttt gttttggagg tttcagcttt taaatctgtg ttaggctgaa tggaaaattg     1320
tggatgttta aatgtcatat aaatttcatc agaggttggc gcacgaaaac cattggcgta    1380
tttaagctgt acacgaagcc aatttgtggg atcaagattt aaccctaaat tgtaagaatg    1440
atgtttatag tcagttttgc gtaataacag ggcaagattg tcttcaaaat ttttttttata   1500 acacggtgtg tcgtaagtgc aatttttcata tcctggaggt attgagtatt tactaccata   1560
aacatattcc tttgagctaa atttcttaaa tagcccagta attaatccat taggaacagg    1620
aatgtttttg tcataactag gcaaatattt tacgtggtca taacgataat ttaaatctag    1680
tcctagccaa gaggtaagtt gcacattatc tccaaaatac aacacattat ttttagtggt    1740
aacagggatt aaataggtat ctttacctttt attggaattc attaagctac atctgtaagc    1800
actatgatca ggtgcaggag tatgctccac aggatatgtg ccatctacag gtttgttaca    1860
gaaaaaattg ccagcccacc attgcacatt ggcaacagtg tagtattgat gattcaccat    1920 acttttagt gttttttcat aaagtccacc atatttagt tggtgttggg tatgccatag      1980
gtgaaattct ttgtctaaat caagtttaat ttgttgggta tgggtgttta aatcacggtc    2040
attaacgaag tctgtgctgt agccatggct ttttggaaat aaaaatttag cactttcata    2100
ttgggttaat ccataattac cttctgctga ttttagtgag atttcaccat attttttgcc    2160
atttaattct ttaatggtaa tatttcggtc ttcataatta tatttgtcat tcccattttc    2220 atctttttcca acaaaaaacct gaaattttt attacaattt aattttcac aattaattaa     2280 gaccgaatca agtgagcctc cttctgtatc tacatcatta ctaacatctt cacccttttt    2340
gttttgtagt tctaagccat aattatattt tcctgtaaat tcttgattgt ctttatcttt    2400
aatcttataa attccaccctt cttctactaa atgtagccct tgtggattac gtacaccagc   2460
acaagtggat tgatgacaat actcatcaga gcgtgcttta ttggtaattt tttgtgagga    2520
ataacttagt ttaatatgat cccaaaaagg ggtttgactg aaattttcat aactaaattg    2580 aatattttt cttttagatt gatcattaat aactcgctcg ccatattttt cctcacattt     2640 agtattttg cattgattga aaatataaga caaatccata ccctttgttt ctaaagtgga    2700
atcatctaat gccacgctca agcgatggtt ttcattaggc tgaaagccca attttattaa    2760
tgtgctttgg cgggtaattt gataaggatc ggcttttttca cgggtaggac caaccgcact    2820
taaatccgcc tgtttattgg gataaatttt ataatcgtag ttttctattt cgtgcccatc    2880
acgttttgta tcaacgacta aaatatcaaa ttttttagaa cgtcctgcta atgtaagtgt    2940
cttaaggttt tgattattca ttgtttgata gccacgttta taggaaagat aataatcttt   3000
```

-continued

| | |
|---|---|
| atctatcaga taatctcgag catctttagt ttcaaatata acagagccac ccaatgcacc | 3060 |
| actaccggat tttaaggagt cagcacccttt ggtaatagtt gctgttttaa cattttcaat | 3120 |
| ttcaatgcta ttacgagtat tattaaaatt gccatagcct tcaaataatt ctttaaatcc | 3180 |
| ttgagagctt aaggtttcag cttgacgaag cccatcaacc ataatacctca cacggttttc | 3240 |
| atcaaacccct cgaacagcat aaccacttgc gcccgttcta cctgtttcaa ccaccgtaat | 3300 |
| acctgtttca tagcgaacga gatcacgaga atcagacgcc tgctgtttcg ctaattttt | 3360 |
| ggcagaaatt tgggtttcac ctacctttttt ctctttcaca ttaattgttt ctgtacttcc | 3420 |
| tgaaacatta atttgttcta gttgttcaga aacattacta ttttggttgg ttggttggtt | 3480 |
| ggttggttgg ttgg | 3494 |

<210> SEQ ID NO 20
<211> LENGTH: 5002
<212> TYPE: DNA
<213> ORGANISM: H. influenzae
<220> FEATURE:
<221> NAME/KEY: misc_feature
<222> LOCATION: (4906)..(4906)
<223> OTHER INFORMATION: n = a, c, g, or t
<220> FEATURE:
<221> NAME/KEY: misc_feature
<222> LOCATION: (4914)..(4915)
<223> OTHER INFORMATION: n = a, c, g, or t

<400> SEQUENCE: 20

| | |
|---|---|
| tataagccca accaggcgcc aacgcagtaa cagtttcctt gagagaaaac ataacaaaag | 60 |
| atggggtatt tctggaagag aaaccaatgc caccaaacca gaaatgaggg cttttaggta | 120 |
| agtaaaatag tgttaataaa tggaaataat agttgccatc taaagttttc gatttaataa | 180 |
| cgagattctc catactcaag tgcggtagaa tttgccaagt tttacttagc cagtctacgt | 240 |
| tttctaaacg aaatacccaa tttatccgca tattgcttca ttgtattcgt tccagagcta | 300 |
| ccgcctgcat accaacgctt tcttgaaaa ggaaccaacg agacttcaac taaggcagtt | 360 |
| tgataactta accccccacc tatacgcaaa gtagcctcat tgtattttt attatcccaa | 420 |
| taatatttc cattcccatt aaacatagtt ttactaaaaa aatgatctgc ccatggccat | 480 |
| tttttctac tgataaagaa taccctaccc cccttcccac tttctttttc caagcggtc | 540 |
| caactaccaa ttttttgtgcc acttttttgga gcgttattca aattatcatc atttaaaaaa | 600 |
| tttaagccta cttgccatat ccattgattc cgctgattta gtgttaaaag atactgatca | 660 |
| ataacaccta aaattttttc atcatctacc tctgtacgta attttttcaaa ttgaattttg | 720 |
| gcagattcat tttcatagtt aaaaaatagg gcttgagcta attgataacg caaaggtagt | 780 |
| aaagatgcgt ctagagcgaa taattcacga taataagcaa tagattgagt taaatcacct | 840 |
| tgttcacgcg cgtcaatagc ctttgcccaa gtgagtaaga aattatcgtg ctgaggaaat | 900 |
| tgtttatata gtggtaataa cagttgaact gcctgagtgt tattttgata taagcaaga | 960 |
| attaacccac gcaaacaag tcttggatgt tgtgctaatt ggcttttgga agagaaata | 1020 |
| atatgcctat ttggtatttc tttcttaggc atagaggaaa aagaggaggt ttttaattcc | 1080 |
| gcactttgaa tcgtatttgt cagtgtatca ttttttaggac gtgcaacttt tgcccaagct | 1140 |
| atattcgtta atgataagcc tattaatgat aagcctatta atgataagaa agaaatttgt | 1200 |
| tttacgccat ttttcatatt ttatccatat tcttaaaaaa ctctaacttg acattattac | 1260 |
| aaaaaaagaa caataatgcg aattattatc aattttgtat aagtattaat tctatgaaat | 1320 |
| ctgtacctct tatcactggt ggactttcct ttttattaag cgcttgtagc gggggaggtg | 1380 |

```
gttcttttga tgtagatgac gtctctaatc cctcctcttc taaaccacgt tatcaagacg   1440
atacttcaag ttcaagaaca aaatctaatt tggaaaagtt gtccattcct tctttaggag   1500
gagggatgaa gttagtggct cagaatctga gtggtaataa agaacctagt ttcttaaatg   1560
aaaatggcta tatatcatat ttttcctcac cttctacgat tgaagatgat gttaaaaatg   1620
ttaaaacaga aaataaaata catacaaatc caattgggct tgaacctaat agagcattac   1680
aagaccccaa tttacaaaaa tacgtttatt ctggtttgta ctatattgag aattggaaag   1740
acttttccaa attagcaaca gaaaaaaaag cctatagtgg ccattatggt tatgcgtttt   1800
attatggtaa taaaactgca acagacttgc cagtaagcgg tgtagcaacg tataaaggaa   1860
cttgggattt catcactgca actaaatatg gccaaaatta ttctttgttc agtaatgcta   1920
gaggtcaagc ttattttcga cgtagtgcta ctcgaggaga tattgattta gaaataatt    1980 caaagaatgg tgatataggc ttaataagtg aatttagtgc agattttggg actaaaaaac   2040
tgacaggaca actgtcttac accaaaagaa aaactgatat tcaacaatat gaaaaggaaa   2100
aactctatga tatagatgcc catatttata gtaatagatt caggggtaaa gttactccta   2160
cgaaatccac atcggatgaa catcccttta ccagcgaggg aacattagaa ggtggttttt   2220
atggacctaa tgctgaagaa ctaggggta aattcttagc tagggataaa cgagttttg    2280 gggtatttag tgccaaagaa acgccagaaa cagaaaagga aaattatcc aaagaaacct    2340 taattgatgg caagctaatt actttctcta ctaaaacagc cgatgcaaca accagtacaa   2400
cagccagtac aacagccgat gtaaaaaccg atgaaaaaaa ctttacgaca aaagatatat   2460
caagttttgg tgaagctgat taccttttaa ttgataatta ccctgttcct cttttccctg   2520
aaggggatac tgatgacttc gtaacgagta acatcacga tattggaaat aaaacctata    2580
aagtagaagc atgttgcaag aatctaagct atgtaaaatt tggtatgtat tatgaggata   2640
aagagaagaa aaacacaaat caaacaggac aataccacca ttttttgtta ggtctccgta   2700
ctcccagttc tcaaattcct gtaacgggaa acgtgaaata tctcggtagt tggtttggtt   2760
atattggtga tgcaagaca tcttactcca ctacaggaaa taaacaacaa gataaaaatg    2820
ctcccgccga gtttgatgtc aattttgaca ataaaacatt aacaggcaaa ttaaaacgag   2880
ccgactcaca aaataccgtg tttaacattg aggcaacctt taaaaatggt agtaatgcct   2940
tcgaaggtaa agcaaccgca aatgtagtga ttgatcccaa aaatacacaa gccacatcta   3000
aagtcaattt cacgacaaca gtaaacgggg cattttatgg tccgcacgct acagaattag   3060
gcggttattt cacctataac ggaaacaatc ctacagctac aaattctgaa agttcctcaa   3120
ccgtaccttc accacccaat tcaccaaatg caagagctgc agttgtcttt ggagctaaaa   3180
gacaagtaga aaaaccaac aagtagaaac aaccaacaag tagaaaaaaa caaataatgg    3240
aatactaaaa atgactaaaa aaccctattt tcgcctaagt attatttctt gtcttttaat   3300
ttcatgctat gtaaaagcag aaactcaaag tataaaagat acaaagaag ctatatcatc    3360 tgaagtggac actcaaagta cagaagattc agaattagaa actatctcag tcactgcaga   3420
aaaagtaaga gatcgtaaag ataatgaagt aactggactt ggcaaaatta tcaaaactag   3480
tgaaagtatc agccgagaac aagtattaaa tattcgtgat ctaacacgct atgatccagg   3540
gatttcagtt gtagaacaag gtcgcggtgc aagttctgga tattctattc gtggtatgga   3600
cagaaataga gttgctttat tagtagatgg ttttacctcaa acgcaatctt atgtagtgca   3660
aagcccttta gttgctcgtt caggatattc tggcactggt gcaattaatg aaattgaata   3720
```

-continued

```
tgaaaatgta aaggccgtcg aaataagcaa ggggggagt tcttctgagt atggtaatgg    3780
agcactagct ggttctgtaa catttcaaag caaatccgca gccgatatct tagaaggaga    3840
caaatcatgg ggaattcaaa ctaaaaatgc ttattcaagc aaaaataaag gctttaccca    3900
ttctttagct gtagcaggaa acaaggtgg atttgaagga cttgctattt acactcaacg    3960
aaattcaatt gaacccaag tccataaaga tgcattaaaa ggcgtgcaaa gttataatcg    4020
attaatcgcc aaagaagatg gatctaatgc atactttgtg atggaagatg agtgtccaaa    4080
ggattataac agttgtatac cttcagccaa accacctgcg aagttatcct cccaaagaga    4140
aaccgtaagc gtttcagatt atacgggggc taaccgtatc aaacctaatc caatgaaata    4200
tgaaagccag tcttggtttt taagaggagg ctatcatttt tctgaacaac attatattgg    4260
tggtattttt gaattcacac aacaaaaatt tgatatccgt gatatgacat ttcccgctta    4320
tttaagatca acagaaaaac cggatttaga aaatagttct ttttatccaa agcaagatta    4380
tggtgcatat caacgtattg aggatggccg aggcgttaaa tatgcaagtg ggctttattt    4440
cgatgaacac catagaaaac agcgtgtagg tattgaatat atttacgaaa ataagaacaa    4500
agcgggaatc attgacaaag cagtgttaag tgctaatcaa caaaacatta tacttgacag    4560
ttatatgcaa catacacatt gcagtctta tcctaatcca agtaagaatt gccgcccaac    4620
acttgataaa ccttattcat actatcattc tgatagaaat gttataaag aaaaacataa    4680 tatgttgcaa ttgaatttag agaaaaaat tcaacaaaat tggcttactc atcaaattgt    4740
cttcaatctt tgggttttga tgactttact tcagcgcttc agcataaaga ttatttacct    4800
cgacggtgtt accgctacgg caaagagtat ttcagagaaa cctggtgaaa caccaagaag    4860
aaatggtttc aaattacaac cttacttata cccaaaacca aatgcnatct ttgnnaggac    4920
gagatcattg taattatcaa ggtagctcct ctattatagt gactgtaaag gggcggtaat    4980
ttaagggaaa aattattatt ca    5002
```

```
<210> SEQ ID NO 21
<211> LENGTH: 6
<212> TYPE: PRT
<213> ORGANISM: H. influenzae

<400> SEQUENCE: 21

Phe Tyr Ala Pro Gly Arg
1               5

<210> SEQ ID NO 22
<211> LENGTH: 5
<212> TYPE: PRT
<213> ORGANISM: H. influenzae

<400> SEQUENCE: 22

Leu Trp Gln Glu Arg
1               5

<210> SEQ ID NO 23
<211> LENGTH: 9
<212> TYPE: PRT
<213> ORGANISM: H. influenzae

<400> SEQUENCE: 23

Phe Gly Gln Ser Gly Phe Ala Ile Arg
1               5

<210> SEQ ID NO 24
```

```
<211> LENGTH: 9
<212> TYPE: PRT
<213> ORGANISM: H. influenzae

<400> SEQUENCE: 24

Ala Gly Val Tyr Asn Leu Thr Asn Arg
1               5

<210> SEQ ID NO 25
<211> LENGTH: 8
<212> TYPE: PRT
<213> ORGANISM: H. influenzae

<400> SEQUENCE: 25

Tyr Ile Thr Trp Asp Ser Ala Arg
1               5

<210> SEQ ID NO 26
<211> LENGTH: 9
<212> TYPE: PRT
<213> ORGANISM: H. influenzae

<400> SEQUENCE: 26

Lys Tyr Ile Thr Trp Asp Ser Ala Arg
1               5

<210> SEQ ID NO 27
<211> LENGTH: 10
<212> TYPE: PRT
<213> ORGANISM: H. influenzae

<400> SEQUENCE: 27

Glu Phe Ala Arg Ile Asn Asn Gly Thr Arg
1               5                   10

<210> SEQ ID NO 28
<211> LENGTH: 9
<212> TYPE: PRT
<213> ORGANISM: H. influenzae

<400> SEQUENCE: 28

Tyr Asp Asn Ile His Tyr Gln Pro Lys
1               5

<210> SEQ ID NO 29
<211> LENGTH: 10
<212> TYPE: PRT
<213> ORGANISM: H. influenzae

<400> SEQUENCE: 29

Leu Ser Phe Asn Pro Thr Glu Asn His Arg
1               5                   10

<210> SEQ ID NO 30
<211> LENGTH: 11
<212> TYPE: PRT
<213> ORGANISM: H. influenzae

<400> SEQUENCE: 30

Ser Arg Gly Gln Asp Leu Ser Tyr Thr Leu Lys
1               5                   10

<210> SEQ ID NO 31
<211> LENGTH: 12
<212> TYPE: PRT
```

<213> ORGANISM: H. influenzae

<400> SEQUENCE: 31

Tyr Glu Thr Gly Val Thr Val Val Glu Ala Gly Arg
1               5                   10

<210> SEQ ID NO 32
<211> LENGTH: 11
<212> TYPE: PRT
<213> ORGANISM: H. influenzae

<400> SEQUENCE: 32

Asn Pro Glu Asp Thr Tyr Asp Ile Tyr Ala Lys
1               5                   10

<210> SEQ ID NO 33
<211> LENGTH: 11
<212> TYPE: PRT
<213> ORGANISM: H. influenzae

<400> SEQUENCE: 33

Phe Thr Leu Ala Ala Asp Leu Tyr Glu His Arg
1               5                   10

<210> SEQ ID NO 34
<211> LENGTH: 13
<212> TYPE: PRT
<213> ORGANISM: H. influenzae

<400> SEQUENCE: 34

Glu Leu Phe Glu Gly Tyr Gly Asn Phe Asn Asn Thr Arg
1               5                   10

<210> SEQ ID NO 35
<211> LENGTH: 14
<212> TYPE: PRT
<213> ORGANISM: H. influenzae

<400> SEQUENCE: 35

Thr Met Val Tyr Gly Leu Gly Tyr Asp His Pro Ser Gln Lys
1               5                   10

<210> SEQ ID NO 36
<211> LENGTH: 16
<212> TYPE: PRT
<213> ORGANISM: H. influenzae

<400> SEQUENCE: 36

Val Glu His Asn Leu Gln Tyr Gly Ser Ser Tyr Asn Thr Thr Met Lys
1               5                   10                  15

<210> SEQ ID NO 37
<211> LENGTH: 17
<212> TYPE: PRT
<213> ORGANISM: H. influenzae

<400> SEQUENCE: 37

Gly Tyr Ala Thr Glu Asn Asn Gln Ser Phe Asn Thr Leu Thr Ala Gly
1               5                   10                  15

Arg

<210> SEQ ID NO 38
<211> LENGTH: 19
<212> TYPE: PRT

<213> ORGANISM: H. influenzae

<400> SEQUENCE: 38

Lys Gly Tyr Ala Thr Glu Asn Asn Gln Ser Phe Asn Thr Leu Thr Leu
1               5                   10                  15

Ala Gly Arg

<210> SEQ ID NO 39
<211> LENGTH: 901
<212> TYPE: DNA
<213> ORGANISM: H. influenzae
<220> FEATURE:
<221> NAME/KEY: misc_feature
<222> LOCATION: (1)..(2)
<223> OTHER INFORMATION: n = a, c, g, or t
<220> FEATURE:
<221> NAME/KEY: misc_feature
<222> LOCATION: (10)..(10)
<223> OTHER INFORMATION: n = a, c, g, or t
<220> FEATURE:
<221> NAME/KEY: misc_feature
<222> LOCATION: (28)..(28)
<223> OTHER INFORMATION: n = a, c, g, or t

<400> SEQUENCE: 39
nntttcatgn cactatccca ctatgtgncc tgcagaacaa tcttatagga cccctttcata     60 gtttttatgg gaattaaaat gaccgatttt agattaaaca acatccta ttccgttatg      120 cttgggctaa cggcaggtgt tgcttatgca gctcaaccaa ccaaccaacc aaccaaccaa    180
ccaaccaacc aaccaaccaa ccaaaatggt aatgtttctg aacaactaga gcaaattaat    240
gtatctggtt ctaccgaaga tagtgataca aaaacaccac caaaaattgc tgaaacggta    300
aaaacggcca aaacgccccc cccagaacaa gcaaacaata ttaaagacat cgccaaatac    360
catacgggtg ttattgtccc tgaagctggg cttttttcgtc caaccgctcc cccattcgtg    420
ttgtccataa caccccccca tttattacta ccgcccgctt acgttcacat ctttcctttt    480
cttcgccgcg ctttcatcat ttttctccgg catttttaca taagtagtcc cttcccgctt    540
ccctcctctc ctcttcctcc ttattttttat tatgatgttt ataagaatct cctctcttac    600
ctattccagc ctcgttgttc tactcgcctt ctgctaaccc tttctcccctt ttccatcctc    660 tctaccccgc cccccctttc tcttttttttt ccccctttct ttttttcccccc cacccctcac    720 ttttcccccgc tttatttttt acacaccccc cgacacaaca ttcatctccc tttgtatccg    780
ctcatctttc ccccccccc ccaccatcc tccgcactct atctttccat tctataccccc    840 cccttcccctt ttcccccccc cccccctttc cgactgcaat ttttttttctt ctcccccctcc    900 g                                                                   901

<210> SEQ ID NO 40
<211> LENGTH: 2979
<212> TYPE: DNA
<213> ORGANISM: H. influenzae

<400> SEQUENCE: 40
atgggaatta aaatgaccga ttttagatta acaaacatc cctattccgt tatgcttggg     60
ctaacggcag gtgttgctta tgcagctcaa ccaaccaacc aaccaaccaa ccaaccaacc    120
aaccaaccaa ccaaccaaaa tggtaatgtt tctgaacaac tagagcaaat taatgtatct    180
ggttctaccg aaaatagtga tacaaaaaca ccaccaaaaa ttgctgaaac ggtaaaaacg    240
gctaaaacgc tggaaagaga acaagcaaac aatattaaag acatcgttaa atacgagacg    300

```
ggcgttactg ttgttgaagc tgggcgtttt gggcaaagcg gttttgccat tcgtggtgta    360
gatgaaaacc gtgtagcgat taatattgat ggattacgtc aagctgaaac cctatcttct    420
caaggcttta aagagctttt tgagggttat ggtaacttca ataatacgcg taatggtgca    480
gaaattgaaa ctttaaaaga agtaaatatt acaaaagggg caaattcaat caaaagtggt    540
agtggttcct taggtggatc tgtaatttat aaaacaaaag atgcgagaga ttatctcctt    600
aacaaggatt actatgtaag ctacaaaaag ggatacgcta cagaaaataa tcaatcattc    660 aatacccta ctcttgcagg acgttataaa agtttgatg ccttagtggt tacaacaagc     720
agaaatggac acgaacttga aaactatgat tacaaaaatg caaatagcct tactcaaggt    780
aaaaaaagag aaaagcaga cccatacaaa attgaacaag atagtacatt attaaaatta    840
tcttttaacc ctacagaaaa tcatcgtttt acccttgcag cagatttata tgaacatcgt    900
tctcgtgggc aagatttatc ctatacacta aaatatcaaa aaacagatcc taatttactc    960
gaggttgatt ctagacacac caatgataaa acaaagagac gtaatatttc ctttagctat   1020
gaaaatttct ctcaaacgcc attttgggat acattaaaaa tcacttattc agatcaacgt   1080
attaaaactc gcgcacgtac agatgactat tgtgatgcag gtgtaagata ttgtgaggga   1140
actgcaaatc ctgcgggact aaaattaaca gatgggaaaa taacacgtcg agatggttca   1200
gaacttcaat ttgaaaaaaa agataaaaat attgataaca acatctatga cttcgataaa   1260
tttattgata ctgatgatcg agtaatagaa ggtaaactag gcctaaggag atcctctgga   1320
acttggtatg attgttcaat atttgattgt aaagataaaa caaaaatgaa aatttttgaa   1380
actgaacatc cttatggcta tggcactact ggaacgtgga aaaaagactt tgaacttgaa   1440 ataaaaaat taaatgacaa aaatttcgct agagtaaagg atgcgaataa taaaacatac   1500
tctattcttc cctcatctcc aggttattta gaacgcctct ggcaagagcg agatttagac   1560
accaacaccc aacaattaaa tttagattta accaaagact tcaaaacttg gcgtgttgaa   1620
cataatctac aatatggtag ctcatataat acaacgatga agcgaatggt taatcgtgct   1680
ggtaatgatg cttctgatgt gcaatggtgg gcagagccta cacttggtta cagtttgttg   1740
tatgataaac ctcacacttg taaaaccgct tatgggggt ggaaagctaa cctttgccct    1800
cgagttgatc ctaaattttc attcttatta cccattaaaa caaaagaaaa atcagtctat   1860
ctctttgata atgttgttat aactgattat ttatcttttg atttgggtta tcgttatgac   1920
aatatccatt atcaaccaaa atataaacac ggcgttacac cgaaattacc tgatgatatt   1980
gtgaaaggat tgtttattcc attaccaagt ggtaaaaata taatgatga tcctgaagtt   2040 aagaaaaacg tacaacaaaa tattgactat atcgctaaac aaaacaaaaa atataaagca   2100
cattcttaca gttttgtttc aacgattgat ccaacgagtt ttcttcgttt acaactaaaa   2160
tattcaaaag gttttagagc accaacttca gatgaaatgt atttcacctt taaacaccct   2220
gatttcacta ttttgccaaa tactaatcta aaaccagaga tagcaaaaac aaaagaaatt   2280
gcttttacat tacataatga tgattggggt tttatctcca caagtctatt taaaaccaac   2340
tataaaaact ttatcgacct aatatttaaa ggagaaaaag attttaaatt agttagcgga   2400
ggtagcacat taccattttc tctttatcaa aatattaata gagatagtgc ggtagtaaaa   2460
ggaatagaaa ttaattcaaa agtattcctt ggtaaaatgg caaatttat ggatggattt    2520 aacctaagct ataaatatac ctatcaaaaa ggaagaatgg atggcaatat tcctatgaat   2580
gcaattcagc ctaaaacgat ggtgtatggc ttaggctatg accacccaag ccaaaaattt   2640
ggatttaatt tctacactac ccacgtagca agtaaaaatc cagaagatac ttatgatatt   2700
```

-continued

```
tatgcgaaag ataaaaacca aaccaacact agcataaaat ggcgcagtaa atcttatact    2760
attctagatt taattggata tgtgcaacca attaaaaatt taaccataag agccggcgta    2820
tataatctta caaaccgtaa atacatcact tgggattctg cgcgttcaat tcgttcattt    2880
ggtacaagta atgttataga tcaaaagaca ggtcaaggca ttaaccgctt ctacgcacca    2940
ggtagaaatt ataagatgtc agttcaattt gagttttaa                          2979
```

<210> SEQ ID NO 41
<211> LENGTH: 992
<212> TYPE: PRT
<213> ORGANISM: H. influenzae

<400> SEQUENCE: 41

```
Met Gly Ile Lys Met Thr Asp Phe Arg Leu Asn Lys His Pro Tyr Ser
1               5                   10                  15

Val Met Leu Gly Leu Thr Ala Gly Val Ala Tyr Ala Ala Gln Pro Thr
            20                  25                  30

Asn Gln Pro Thr Asn Gln Pro Thr Asn Gln Pro Thr Asn Gln Asn Gly
        35                  40                  45

Asn Val Ser Glu Gln Leu Glu Gln Ile Asn Val Ser Gly Ser Thr Glu
    50                  55                  60

Asn Ser Asp Thr Lys Thr Pro Pro Lys Ile Ala Glu Thr Val Lys Thr
65                  70                  75                  80

Ala Lys Thr Leu Glu Arg Glu Gln Ala Asn Asn Ile Lys Asp Ile Val
                85                  90                  95

Lys Tyr Glu Thr Gly Val Thr Val Val Glu Ala Gly Arg Phe Gly Gln
            100                 105                 110

Ser Gly Phe Ala Ile Arg Gly Val Asp Glu Asn Arg Val Ala Ile Asn
        115                 120                 125

Ile Asp Gly Leu Arg Gln Ala Glu Thr Leu Ser Ser Gln Gly Phe Lys
    130                 135                 140

Glu Leu Phe Glu Gly Tyr Gly Asn Phe Asn Asn Thr Arg Asn Gly Ala
145                 150                 155                 160

Glu Ile Glu Thr Leu Lys Glu Val Asn Ile Thr Lys Gly Ala Asn Ser
                165                 170                 175

Ile Lys Ser Gly Ser Gly Ser Leu Gly Gly Ser Val Ile Tyr Lys Thr
            180                 185                 190

Lys Asp Ala Arg Asp Tyr Leu Leu Asn Lys Asp Tyr Tyr Val Ser Tyr
        195                 200                 205

Lys Lys Gly Tyr Ala Thr Glu Asn Asn Gln Ser Phe Asn Thr Leu Thr
    210                 215                 220

Leu Ala Gly Arg Tyr Lys Lys Phe Asp Ala Leu Val Val Thr Thr Ser
225                 230                 235                 240

Arg Asn Gly His Glu Leu Glu Asn Tyr Asp Tyr Lys Asn Ala Asn Ser
                245                 250                 255

Leu Thr Gln Gly Lys Lys Arg Glu Lys Ala Asp Pro Tyr Lys Ile Glu
            260                 265                 270

Gln Asp Ser Thr Leu Leu Lys Leu Ser Phe Asn Pro Thr Glu Asn His
        275                 280                 285

Arg Phe Thr Leu Ala Ala Asp Leu Tyr Glu His Arg Ser Arg Gly Gln
    290                 295                 300

Asp Leu Ser Tyr Thr Leu Lys Tyr Gln Lys Thr Asp Pro Asn Leu Leu
305                 310                 315                 320
```

-continued

```
Glu Val Asp Ser Arg His Thr Asn Asp Lys Thr Lys Arg Arg Asn Ile
            325                 330                 335

Ser Phe Ser Tyr Glu Asn Phe Ser Gln Thr Pro Phe Trp Asp Thr Leu
            340                 345                 350

Lys Ile Thr Tyr Ser Asp Gln Arg Ile Lys Thr Arg Ala Arg Thr Asp
            355                 360                 365

Asp Tyr Cys Asp Ala Gly Val Arg Tyr Cys Glu Gly Thr Ala Asn Pro
            370                 375                 380

Ala Gly Leu Lys Leu Thr Asp Gly Lys Ile Thr Arg Arg Asp Gly Ser
385                 390                 395                 400

Glu Leu Gln Phe Glu Lys Lys Asp Lys Asn Ile Asp Asn Asn Ile Tyr
            405                 410                 415

Asp Phe Asp Lys Phe Ile Asp Thr Asp Asp Arg Val Ile Glu Gly Lys
            420                 425                 430

Leu Gly Leu Arg Arg Ser Ser Gly Thr Trp Tyr Asp Cys Ser Ile Phe
            435                 440                 445

Asp Cys Lys Asp Lys Thr Lys Met Lys Ile Phe Glu Thr Glu His Pro
            450                 455                 460

Tyr Gly Tyr Gly Thr Thr Gly Thr Trp Lys Lys Asp Phe Glu Leu Glu
465                 470                 475                 480

Ile Lys Lys Leu Asn Asp Lys Asn Phe Ala Arg Val Lys Asp Ala Asn
            485                 490                 495

Asn Lys Thr Tyr Ser Ile Leu Pro Ser Ser Pro Gly Tyr Leu Glu Arg
            500                 505                 510

Leu Trp Gln Glu Arg Asp Leu Asp Thr Asn Thr Gln Leu Asn Leu
            515                 520                 525

Asp Leu Thr Lys Asp Phe Lys Thr Trp Arg Val Glu His Asn Leu Gln
            530                 535                 540

Tyr Gly Ser Ser Tyr Asn Thr Thr Met Lys Arg Met Val Asn Arg Ala
545                 550                 555                 560

Gly Asn Asp Ala Ser Asp Val Gln Trp Trp Ala Glu Pro Thr Leu Gly
            565                 570                 575

Tyr Ser Leu Leu Tyr Asp Lys Pro His Thr Cys Lys Thr Ala Tyr Gly
            580                 585                 590

Gly Trp Lys Ala Asn Leu Cys Pro Arg Val Asp Pro Lys Phe Ser Phe
            595                 600                 605

Leu Leu Pro Ile Lys Thr Lys Glu Lys Ser Val Tyr Leu Phe Asp Asn
            610                 615                 620

Val Val Ile Thr Asp Tyr Leu Ser Phe Asp Leu Gly Tyr Arg Tyr Asp
625                 630                 635                 640

Asn Ile His Tyr Gln Pro Lys Tyr Lys His Gly Val Thr Pro Lys Leu
            645                 650                 655

Pro Asp Asp Ile Val Lys Gly Leu Phe Ile Pro Leu Pro Ser Gly Lys
            660                 665                 670

Asn Asn Asn Asp Asp Pro Glu Val Lys Lys Asn Val Gln Gln Asn Ile
            675                 680                 685

Asp Tyr Ile Ala Lys Gln Asn Lys Lys Tyr Lys Ala His Ser Tyr Ser
            690                 695                 700

Phe Val Ser Thr Ile Asp Pro Thr Ser Phe Leu Arg Leu Gln Leu Lys
705                 710                 715                 720

Tyr Ser Lys Gly Phe Arg Ala Pro Thr Ser Asp Glu Met Tyr Phe Thr
            725                 730                 735

Phe Lys His Pro Asp Phe Thr Ile Leu Pro Asn Thr Asn Leu Lys Pro
```

-continued

```
              740             745             750
Glu Ile Ala Lys Thr Lys Glu Ile Ala Phe Thr Leu His Asn Asp Asp
            755             760             765
Trp Gly Phe Ile Ser Thr Ser Leu Phe Lys Thr Asn Tyr Lys Asn Phe
            770             775             780
Ile Asp Leu Ile Phe Lys Gly Glu Lys Asp Phe Lys Leu Val Ser Gly
785             790             795             800
Gly Ser Thr Leu Pro Phe Ser Leu Tyr Gln Asn Ile Asn Arg Asp Ser
                805             810             815
Ala Val Val Lys Gly Ile Glu Ile Asn Ser Lys Val Phe Leu Gly Lys
            820             825             830
Met Ala Lys Phe Met Asp Gly Phe Asn Leu Ser Tyr Lys Tyr Thr Tyr
            835             840             845
Gln Lys Gly Arg Met Asp Gly Asn Ile Pro Met Asn Ala Ile Gln Pro
            850             855             860
Lys Thr Met Val Tyr Gly Leu Gly Tyr Asp His Pro Ser Gln Lys Phe
865             870             875             880
Gly Phe Asn Phe Tyr Thr Thr His Val Ala Ser Lys Asn Pro Glu Asp
                885             890             895
Thr Tyr Asp Ile Tyr Ala Lys Asp Lys Asn Gln Thr Asn Thr Ser Ile
                900             905             910
Lys Trp Arg Ser Lys Ser Tyr Thr Ile Leu Asp Leu Ile Gly Tyr Val
            915             920             925
Gln Pro Ile Lys Asn Leu Thr Ile Arg Ala Gly Val Tyr Asn Leu Thr
            930             935             940
Asn Arg Lys Tyr Ile Thr Trp Asp Ser Ala Arg Ser Ile Arg Ser Phe
945             950             955             960
Gly Thr Ser Asn Val Ile Asp Gln Lys Thr Gly Gln Gly Ile Asn Arg
                965             970             975
Phe Tyr Ala Pro Gly Arg Asn Tyr Lys Met Ser Val Gln Phe Glu Phe
                980             985             990
```

NONTYPEABLE HAEMOPHILUS INFLUENZAE VIRULENCE FACTORS

RELATED APPLICATIONS

The present application claims priority benefit from U.S. Provisional Application 60/458,234 filed Mar. 27, 2003 which is incorporated herein by reference in its entirety.

Scientific work relating to the invention was supported by Grant No. DC03915 from the United States National Institute of Health. The United States government may have certain rights in the invention.

FIELD OF INVENTION

The invention relates to a mutation within the sap operon of an avirulent clone of a nontypeable strain of Haemophilus influenzae (NTHi). The invention relates to methods of modulating NTHi virulence and NTHi sensitivity to antimicrobial agents. The invention also relates to a novel 110 kDa NTHi outer membrane protein and the polynucleotide that encodes this outer membrane protein. Methods of screening for NTHi infection, and treating and preventing NTHi related disorders are also contemplated.

BACKGROUND

Otitis media (OM) is a highly prevalent pediatric disease worldwide and is the primary cause for emergency room visits by children (Infante-Rivand and Fernandez, *Epidemiol. Rev.*, 15: 444-465,1993). Recent statistics indicate that 24.5 million physician office visits were made for OM in 1990, representing a greater than 200% increase over those reported in the 1980's. While rarely associated with mortality any longer, the morbidity associated with OM is significant. Hearing loss is a common problem associated with this disease, often times affecting a child's behavior, education and development of language skills (Baldwin, *Am. J. Otol.*, 14: 601-604, 1993; Hunter et al., *Ann. Otol. Rhinol. Laryngol. Suppl.*, 163: 59-61, 1994; Teele et al., *J. Infect. Dis.*, 162:685-694, 1990). The socioeconomic impact of OM is also great, with direct and indirect costs of diagnosing and managing OM exceeding $5 billion annually in the U.S. alone (Kaplan et al., *Pediatr. Infect. Dis. J*, 16: S9-11, 1997).

Whereas antibiotic therapy is common and the surgical placement of tympanostomy tubes has been successful in terms of draining effusions, clearing infection and relieving pain associated with the accumulation of fluids in the middle ear, the emergence of multiple antibiotic-resistant bacteria and the invasive nature associated with tube placement, has illuminated the need for more effective and accepted approaches to the management and preferably, the prevention of OM. Surgical management of chronic OM involves the insertion of tympanostomy tubes through the tympanic membrane while a child is under general anesthesia. While this procedure is commonplace (prevalence rates are ~13%; Bright et al., *Am. J. Public Health*, 83(7): 1026-8, 1993) and is highly effective in terms of relieving painful symptoms by draining the middle ear of accumulated fluids, it too has met with criticism due to the invasive nature of the procedure and its incumbent risks (Berman et al., *Pediatrics*, 93(3): 353-63, 1994; Bright et al., supra.; Cimons, *ASM News*, 60: 527-528; Paap, *Ann. Pharmacother.*, 30(11): 1291-7, 1996).

Progress in vaccine development is most advanced for *Streptococcus pneumoniae*, the primary causative agent of acute OM (AOM), as evidenced by the recent approval and release of a seven-valent capsular-conjugate vaccine, PRE-VNAR® (Eskola and Kilpi, *Pediatr. Infect. Dis. J.* 16: S72-78, 2000). While PREVNAR® has been highly efficacious for invasive pneumococcal disease, coverage for OM has been disappointing (6-8%) with reports of an increased number of OM cases due to serotypes not included in the vaccine (Black et al., *Pediatr. Infect. Dis J.*, 19: 187-195; Eskola et al., *Pediatr. Infect. Dis J.*, 19: S72-78, 2000; Eskola et al., *N. Engl. J. Med.* 344: 403-409, 2001; Snow et al., *Otol. Neurotol.*, 23: 1-2, 2002). Less progress has been made for nontypeable *Haemophilus influenzae* (NTHi), the gram-negative pathogen that predominates in chronic OM with effusion (Klein, *Pediatr. Infect. Dis J.*, 16: S5-8, 1997; Spinola et al., *J. Infect. Dis.*, 54: 100-109, 1986). Hampering development of effective vaccines against NTHi, has been the incomplete understanding of the pathogenesis of NTHi-induced middle ear disease. Contributing to this delay was a lack of understanding of the dynamic interplay between microbe-expressed virulence factors and the host's immune response as the disease progresses from one of host immunogenic tolerance of a benign nasopharyngeal commensal, to that of an active defensive reaction to an opportunistic invader of the normally sterile middle ear space.

There has been a poor understanding of how NTHi causes OM in children. The identification of putative virulence factors necessary for induction of OM will contribute significantly to the understanding of the host-pathogen interaction and ultimately, the identification of potential vaccine candidates and targets of chemotherapy. There is a tremendous need to develop more effective and accepted approaches to the management and preferably, the prevention of otitis media. Vaccine development is a very promising and cost effective method to accomplish this goal (Giebank, *Pediair. Infect. Dis J.*, 13(11): 1064-8, 1994: Karma et al., *Int. J. Pedritr. Otorhinolaryngol.*, 32(Suppl.): S127-34, 1995).

SUMMARY OF INVENTION

Signature-tagged mutagenesis screening of avirulent NTHi clones using a transbullar chinchilla model of OM identified a mutant that was unable to survive in the environment of the middle ear during OM. This mutant of interest harbored an interruption in the sapF gene within the sap operon. The mutant is denoted herein as sapF::mTn5. This mutant was 3-fold more sensitive to the action of the antimicrobial peptide protamine and displayed a concurrent loss of an approximately 110 kDa outer membrane protein (OMP).

The sap operon is known to be involved in conferring resistance to the action of antimicrobial peptides. The sap operon was first identified and characterized in *S. typhimurium* where it functions in resistance to the cationic peptide protamine. (Parra-Lopez et al., *EMBO J.* 12: 4053-62, 1993). A search of the available complete and incomplete bacterial genome sequences in NCBI databases revealed sap operons in the genomes of *H. influenzae, Pasteurella multocida, Yersinia pestis, S. typhimurium, S. enterica, E. coli, E. chrysanthemi*, and *V. cholerae*. All of these organisms had the conserved gene order of sapABCDF in the operon. The structure of the gene cluster suggests that all sap genes were co-transcribed as a single polycistronic mRNA. An interesting finding is the presence of sapZ, which encodes a hypothetical transmembrane protein and is unique in *H. influenzae* due to its placement within the sap operon. In other organisms with a comparable sap system, sapZ is not co-transcribed with sapA-F. The sapABCDF gene products are components of an ABC transporter system involved in peptide uptake (Parra-Lopez et al., supra.). The SapA protein is a periplasmic dipeptide binding protein. SapB and SapC are transmembrane proteins embedded in the inner membrane. SapD and SapF are two ATP hydrolyzing proteins localized in cytoplasm presumably associated with SapB and SapC. The sapZ gene product is an as-yet uncharacterized hypothetical protein that is predicted to be a transmembrane protein with gene homologs in sap operon-containing bacteria, *P. multocida, S. typhimurium, S. enterica*, and *E. coli* 0157:H7, and in *Neisseria meningitidis* and *Pseudomonas aeriginosa*, which do not contain a sap operon. In bacteria containing the described sap system, however, sapZ is not located near the sap operon in the bacterial genome.

The present invention provides the sequences of the 6 NTHi sap genes (sapA, sapB, sapC, sapD, sapF and sapZ) set out as SEQ ID NOS: 1-6 respectively. The polypeptide gene products encoded by the 6 NTHi sap genes (SapA, SapB, SapC, SapD, SapF, and SapZ) are set out as SEQ ID NOS: 7-12 respectively. The polynucleotide sequence of the complete NTHi sap operon is set out as SEQ ID NO: 13.

In vitro phenotypic assays described herein revealed that the sapF mutant was more sensitive to the antimicrobial peptide protamine than the parent strain, in addition to its absence of a 110 kDa OMP. This was the first observation about the NTHi sap gene playing an essential role in survival in the microenvironment of the chinchilla middle ear and in resistance to an antimicrobial peptide. The invention contemplates identifying the relevant host antimicrobial peptides that may be responsible in part for the rapid clearance of the sapF mutant, and determining the identity of the absent OMP, and also the functional linkage between this protein and the SapF protein.

A non-polar in-frame mutation of the NTHi sap operon, denoted herein as sapA::kan, was more sensitive to chinchilla antimicrobial peptide beta-defensin-1 than the parent strain in vitro. This mutation also attenuated bacterial survival in vivo in the chinchilla middle ear. These studies further demonstrate that the NTHi sap operon is critical to survival in vivo.

The present invention also provides for the polynucleotide sequences that encodes a portion of the polypeptide sequence of the novel NTHi 110 kDa OMP protein that is set out as SEQ ID NOS: 21-38. Additional sequence analysis identified the full length sequence of the NTHi 110 kDa OMP set out as SEQ ID NO: 41 that is encoded by the nucleic acid set out in SEQ ID NO: 40.

The present invention also provides for antibodies specific for the NTHi SapA, SapB, SapC, SapD, SapF and SapZ proteins and the NTHi 110 kDa OMP protein of the invention. Methods of detecting NTHi bacteria in a human or in sample, such as serum, sputum, ear fluid, blood, urine, lymphatic fluid and cerebrospinal fluid are contemplated. These methods include detecting a NTHi sap polynucleotides or the NTHi 110 kDa OMP polynucleotide with specific polynucleotide probes or detecting an NTHi Sap protein or the NTHi 110 kDa OMP protein with specific antibodies. The invention also contemplates diagnostic kits which utilize these methods of detecting NTHi bacteria.

According to the present invention, the presence of the functional NTHi Sap proteins and/or the NTHi 110 kDa OMP protein is associated with survivability of the NTHi bacterium within the middle ear. The sapA gene has been shown to be upregulated during OM infection of the middle ear in the chinchilla. Expression of SapZ protein as part of the sap operon is unique to NTHi and therefore is contemplated to be a target for therapies to infections caused by NTHI. Therefore, the NTHi SapA, SapB, SapC, SapD, SapF, SapZ and 110 kDa OMP protein are contemplated as vaccine candidates and/or targets of chemotherapy. The present invention also contemplates methods of eliciting an immune response to one or more of the NTHi SapA, SapB, SapC, SapD, SapF, SapZ and 110 kDa OMP protein of the invention by administering one or more of those proteins or peptides thereof. In one aspect, these methods involve administering one or more of the NTHi SapA, SapB, SapC, SapD, SapF, SapZ and 110 kDa OMP protein or a peptide thereof as a vaccine for treatment and/or prevention of diseases caused by NTHi infection, such as OM.

As a method of treating or preventing NTHi infection, the present invention contemplates administering a molecule that inhibits expression or the activity of one or more of the NTHi SapA, SapB, SapC, SapD, SapF, SapZ and/or 110 kDa OMP proteins. In particular, the invention contemplates methods of treating or preventing NTHi infection comprising modulating expression of one or more of the NTHi SapA, SapB, SapC, SapD, SapF, SapZ and/or 110 kDa OMP protein by administering an antisense oligonucleotide that specifically binds to prevent expression of the appropriate NTHi genes. The invention also contemplates methods of treating or preventing NTHi infection comprising administering antibodies or small molecules that modulate the activity of one or more of the NTHi SapA, SapB, SapC, SapD, SapF, SapZ and 110 kDa OMP protein.

The invention also provides for methods of modulating the virulence of the NTHi bacterium or increasing NTHi sensitivity to antimicrobial agents. These methods include mutating the NTHi genes within the sap operon. The sap operon is known to be associated with resistance to antimicrobial agents, and a disruption or mutation within this operon is contemplated to decrease virulence. These method include utilizing methods of intercalating or disrupting the DNA within the sap operon.

Polynucleotides and Polypeptides of the Invention

The present invention provides polynucleotide sequences of the NTHi sap operon genes (sapA, sapB, sapC, sapD, sapF and sapZ) set out as SEQ ID NOS: 1-6, respectively. The present invention also provides for the polypeptides encoded by the sap operon polynucleotides of the present invention. In addition, the invention provides for the polynucleotide sequence encoding the NTHi 110 kDa OMP set out in SEQ ID NO: 40. The invention provides for polynucleotides that hybridize under stringent conditions to (a) the complement of the nucleotide sequence of SEQ ID NOS: 1-6, (b) the complement of the nucleotide sequence encoding the SEQ ID NO: 40, (c) a polynucleotide which is an allelic variant of any polynucleotides recited above; (d) a polynucleotide which encodes a species homolog of any of the proteins recited above; or (e) a polynucleotide that encodes a polypeptide comprising a specific domain or truncation of the NTHi polypeptides of the present invention.

The NTHi polynucleotides of the invention also include nucleotide sequences that are substantially equivalent to the polynucleotides recited above. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to one of the NTHi sap operon polynucleotides or the polynucleotide encoding the NTHi 110 kDa OMP recited above.

Included within the scope of the nucleic acids of the invention are nucleic acid fragments that hybridize under stringent conditions to one of the NTHi sap operon polynucleotides of SEQ ID NOS: 1-6 or polynucleotides encoding the NTHi 110 kDa OMP (SEQ ID NO: 40), or complements thereof, which fragment is greater than about 5 nucleotides, preferably 7 nucleotides, more preferably greater than 9 nucleotides and most preferably greater than 17 nucleotides in length. Fragments of, e.g., 15, 17, or 20 nucleotides or more that are selective for (i.e., specifically hybridize to any one of the polynucleotides of the invention) are contemplated. Probes capable of specifically hybridizing to a polynucleotide can differentiate NTHi polynucleotides of the invention from other polynucleotides in the same family of genes or can differentiate NTHi genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, $2^{nd}$ Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

The sequences falling within the scope of the present invention are not limited to these specific sequences, but also include allelic and species variations thereof. Allelic and species variations can be routinely determined by comparing the sequence provided in SEQ ID NOS: 1-6, the nucleic acid sequence encoding the NTHi 110 kDa OMP polypeptide (SEQ ID NO: 40), a representative fragment thereof, or a nucleotide sequence at least 90% identical, preferably 95% identical, to SEQ ID NOS: 1-6 or SEQ ID NO: 40, with a sequence from another isolate of the same species. Preferred computer program methods to determine identity and similarity between two sequences include, but are not limited to, the GCG program package, including GAP (Devereux et al., *Nucl. Acid. Res.*, 12: 387, 1984; Genetics Computer Group, University of Wisconsin, Madison, Wis.), BLASTP, BLASTN, and FASTA (Altschul et al., *J. Mol. Biol.*, 215: 403-410, 1990). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well-known Smith Waterman algorithm may also be used to determine identity.

Furthermore, to accommodate codon variability, the invention includes nucleic acid molecules coding for the same amino acid sequences as do the specific open reading frames (ORF) disclosed herein. In other words, in the coding region of an ORF, substitution of one codon for another codon that encodes the same amino acid is expressly contemplated. The present invention further provides isolated NTHi polypeptides encoded by the NTHi nucleic acid fragments of the present invention or by degenerate variants of the nucleic acid fragments of the present invention. The term "degenerate variant" refers to nucleotide fragments that differ from a nucleic acid fragment of the present invention (e.g., an ORF) by nucleotide sequence but, due to the degeneracy of the genetic code, encode an identical NTHi polypeptide sequence. Preferred nucleic acid fragments of the present invention are the ORFs that encode proteins.

The isolated polypeptides of the invention include, but are not limited to, a polypeptide comprising: the amino acids encoded by the nucleotide sequences SEQ ID NOS: 7-12, the nucleotide sequence encoding NTHi 110 kDa OMP (SEQ ID NO: 41), or the corresponding full length or mature protein. Polypeptides of the invention also include polypeptides preferably with biological or immunogenic activity that are encoded by: (a) a polynucleotide having the nucleotide sequences set forth in SEQ ID NOS: 1-6 or SEQ ID NO: 40 or (b) polynucleotides encoding the amino acid sequence set forth as SEQ ID NOS: 7-12 or (c) a polynucleotide having the nucleotide sequence encoding the amino acid sequences set forth as SEQ ID NO: 41, (d) polynucleotides that hybridize to the complement of the polynucleotides of either (a), (b) or (c) under stringent hybridization conditions.

The invention also provides biologically active or immunogenically active variants of the polypeptides of the present invention; and "substantial equivalents" thereof (e.g., with at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity) that retain biological and/or immunogenic activity. Polypeptides encoded by allelic variants may have a similar, increased, or decreased activity compared to one of the polypeptides encoded by the polynucleotides comprising SEQ ID NOS: 1-6 or the (NTHi 110 kDa OMP polypeptide (SEQ IS NO: 41).

The invention also provides for NTHi polypeptides with one or more conservative amino acid substitutions that do not affect the biological and/or immunogenic activity of the polypeptide. Alternatively, the NTHi polypeptides of the invention are contemplated to have conservative amino acids substitutions that may or may not alter biological activity. The term "conservative amino acid substitution" refers to a substitution of a native amino acid residue with a nonnative residue, including naturally occurring and non-naturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine General rules for amino acid substitutions are set forth in Table 1 below.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

Antisense polynucleotides complementary to the polynucleotides encoding one of the NTHi sap operon proteins and NTHi 110 kDa OMP protein are also provided.

Antisense technology may be employed to inhibit the activity of NTHi SapA, SapB, SapC, SapD, SapF, SapZ or NTHi 110 kDa OMP protein. Such inhibition may be effected by nucleic acid molecules which are complementary to and hybridize to expression control sequences (triple helix formation) or to sap operon mRNA or the 110 kDa OMP mRNA. For example, antisense DNA, RNA or RNAi molecules, which have a sequence that is complementary to at least a portion of the selected gene(s) can be introduced into the cell. Antisense probes may be designed by available techniques using the nucleotide sequence of NTHi sap operon or the gene that encodes the NTHi 110 kDa OMP protein disclosed herein. Typically, each such antisense molecule will be complementary to the start site (5' end) of each selected sap operon gene or the gene encoding the 110 kDa OMP protein. When the antisense molecule then hybridizes to the corresponding mRNA, translation of this mRNA is prevented or reduced.

Alternatively, gene therapy may be employed to create a dominant-negative inhibitor of one of the NTHi sap operon gene products or the NTHi 110 kDa OMP protein. The DNA encoding a mutant polypeptide of these polypeptides can be prepared and introduced into the cells of a patient using either viral or non-viral methods. Each such mutant is typically designed to compete with endogenous polypeptide in its biological role.

In some cases, it may be desirable to prepare nucleic acid molecules encoding variants of the sap operon gene product or the NTHi 110 kDa OMP protein. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Homologous recombination may also be used to introduce mutations in genes of interest. The basic technique was developed as a method for introducing specific mutations into specific regions of the mammalian genome (Thomas et al., Cell, 44:419-428, 1986; Thomas and Capecchi, Cell, 51:503-512, 1987; Doetschman et al., Proc. Natl. Acad. Sci., 85:8583-8587, 1988) or to correct specific mutations within defective genes (Doetschman et al., Nature, 330:576-578, 1987). Exemplary homologous recombination techniques are described in U.S. Pat. No. 5,272,071.

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a sap operon gene product of the NTHi 110 kDa OMP, e.g., flanking sequences. For example, a promoter/enhancer element, a suppresser, or an exogenous transcription modulatory element is inserted in the genome of the intended host cell in proximity and orientation sufficient to influence the transcription of DNA encoding the desired NTHi polypeptide. The control element controls a portion of the DNA present in the host cell genome. Thus, the expression of the desired NTHi polypeptide may be achieved not by transfection of DNA that encodes NTHi polypeptide itself, but rather by the use of targeting DNA (containing regions of homology with the endogenous gene of interest) coupled with DNA regulatory segments that provide the endogenous gene sequence with recognizable signals for transcription of an NTHi polypeptide.

The invention contemplates that polynucleotides of the invention may be inserted in a vector for amplification or expression. For expression, the polynucleotides are operatively linked to appropriate expression control sequence such as a promoter and polyadenylation signal sequences. Further provided are cells containing polynucleotides of the invention. Exemplary prokaryotic hosts include bacteria such as E. coli, Bacillus, Streptomyces, Pseudomonas, Salmonella and Serratia.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Antibodies and Methods for Eliciting an Immune Response

The invention provides antibodies which bind to antigenic epitopes unique to one of the NTHi SapA, SapB, SapC; SapD, SapF, SapZ and NTHi 110 kDa OMP polypeptides. Also provided are antibodies that bind to antigenic epitopes common among multiple *H. influenzae* subtypes but unique with respect to any other antigenic epitopes. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art.

In vitro complement mediated bactericidal assay systems (Musher et al., *Infect. Immun.* 39: 297-304, 1983; Anderson et al., *J. Clin. Invest.* 51: 31-38, 1972) may be used to measure the bactericidal activity of antibodies that specifically bind to NTHi SapA, SapB, SapC, SapD, SapF, SapZ and NTHi 110 kDa OMP polypeptides. Further data on the ability of NTHi 110 kDa OMP protein and peptides thereof elicit a protective antibody response may be generated by using animal models of infection such as the chinchilla model system described herein.

The present invention provides for antibodies specific for the NTHi polypeptides of the present invention and fragments thereof, which exhibit the ability to kill both *H. influenzae* bacteria and to protect humans from NTHi infection. The present invention also provides for antibodies specific for the NTHi polypeptides of the invention that reduce the virulence, inhibit adherence, inhibit cell division, and/or inhibit penetration of *H. influenzae* bacteria into the epithelium or enhance phagocytosis of the *H. influenzae* bacteria.

It is also possible to confer short-term protection to a host by passive immunotherapy by the administration of preformed antibody against an epitope or epitopes of the NTHi SapA, SapB, SapC, SapD, SapF, SapZ proteins and NTHi 110 kDa OMP protein. Thus, the contemplated vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks. Alternatively, these antibodies can be used in the production of anti-idiotypic antibody, which in turn can be used as an antigen to stimulate an immune response against one or more of the NTHi SapA, SapB, SapC, SapD, SapF, SapZ proteins and NTHi 110 kDa OMP protein.

The invention contemplates methods of eliciting an immune response to NTHi in an individual. These methods include immune responses that kill the NTHi bacteria and immune responses which block *H. influenzae* attachment to cells or *H. influenzae* proliferation. In one embodiment, the methods comprise a step of administering an immunogenic dose of a composition comprising one or more of the NTHi SapA, SapB, SapC, SapD, SapF, SapZ and NTHi 110 kDa OMP proteins or peptides thereof. In another embodiment, the methods comprise administering an immunogenic dose of a composition comprising a cell expressing one or more of the NTHi SapA, SapB, SapC, SapD, SapF, SapZ and NTHi 110 kDa OMP proteins or peptides thereof. In yet another embodiment, the methods comprise administering an immunogenic dose of a composition comprising a polynucleotide encoding one or more of the NTHi SapA, SapB, SapC, SapD, SapF, SapZ and NTHi 110 kDa OMP proteins or peptides thereof. The polynucleotide may be a naked polynucleotide not associated with any other nucleic acid or may be in a vector such as a plasmid or viral vector (e.g., adeno-associated virus vector or adenovirus vector). Administration of the compositions may be by routes standard in the art, for example, parenteral, intravenous, oral, buccal, nasal, pulmonary, rectal, or vaginal. The methods may be used in combination in a single individual. The methods may be used prior or subsequent to NTHi infection of an individual.

An "immunogenic dose" of a composition of the invention is one that generates, after administration, a detectable humoral and/or cellular immune response in comparison to the immune response detectable before administration or in comparison to a standard immune response before administration. The invention contemplates that the immune response resulting from the methods may be protective and/or therapeutic. For example, an "immunogenic dose" is a dose that is adequate to produce antibody and/or T cell immune responses to NTHi. In some embodiments the immune response protects said individual from NTHi infection, particularly NTHi infection of the middle ear, nasopharynx and/or lower airway. Also provided are methods whereby such immune response slows bacterial replication. The immune response may be induced therapeutically or prophylactically and may take the form of antibody immunity or cellular immunity such as that arising from CTL or CD4+ T cells. The NTHi protein or an antigenic peptide thereof may be fused with co-protein which may not by itself induce antibodies, but is capable of stabilizing the first protein and producing a fused protein which will have immunogenic and protective properties. Thus fused recombinant protein, may further comprise an antigenic co-protein, such as glutathione-S-transferase (GST) or beta-galactosidase, relatively large co-proteins that solubilize the protein and facilitate production and purification thereof. Moreover, the co-protein may act as an adjuvant in the sense of providing generalized stimulation of the immune system. The co-protein may be attached to either the amino or carboxy terminus of the first protein.

The invention correspondingly provides compositions suitable for eliciting an immune response to NTHi infection, wherein antibodies elicited block binding of NTHi bacterium to the host's cells, reduce the virulence, inhibit adherence, inhibit cell division, and/or inhibit penetration of *H. influenzae* bacteria into the epithelium or enhance phagocytosis of the *H. influenzae* bacteria. The compositions comprise one or more NTHi SapA, SapB, SapC, SapD, SapF, SapZ and NTHi 110 kDa OMP proteins or peptides thereof, cells expressing one or more NTHi SapA, SapB, SapC, SapD, SapF, SapZ and NTHi 110 kDa OMP proteins, or polynucleotides encoding one or more NTHi SapA, SapB, SapC, SapD, SapF, SapZ proteins and NTHi 110 kDa OMP protein. The compositions may also comprise other ingredients such as carriers and adjuvants.

The invention includes methods of blocking binding of NTHi bacteria to host cells in an individual. The methods comprise inducing and/or administering antibodies of the invention that block binding of NTHi cellular attachment, reduce the virulence, inhibit adherence, inhibit cell division, and/or inhibit penetration of *H. influenzae* bacteria into the epithelium or enhance phagocytosis of the *H. influenzae* bacteria. Alternatively, administration of one or more small molecules that block binding of NTHi cell attachment is contemplated. In vitro assays may be used to demonstrate the ability of an antibody, polypeptide or small molecule of the invention to block NTHi cell attachment.

Pharmaceutical compositions comprising antibodies of the invention, or small molecules of the invention that block NTHi cellular attachment, reduce the virulence, inhibit adherence, inhibit cell division, and/or inhibit penetration of *H. influenzae* bacteria into the epithelium or enhance phagocytosis of the *H. influenzae* bacteria are provided. The pharmaceutical compositions may consist of one of the foregoing active ingredients alone, may comprise combinations of the foregoing active ingredients or may comprise additional active ingredients used to treat bacterial infections. The pharmaceutical compositions may comprise one or more additional ingredients such as pharmaceutically effective carriers. Dosage and frequency of the administration of the pharmaceutical compositions are determined by standard techniques and depend, for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, or vaginal.

Also provided by the invention are methods for detecting NTHi infection in an individual. In one embodiment, the methods comprise detecting one or more NTHi SapA, SapB, SapC, SapD, SapF, SapZ and NTHi 110 kDa OMP proteins in a sample using primers or probes that specifically bind to the polynucleotides. Detection of the polynucleotides may be accomplished by numerous techniques routine in the art involving, for example, hybridization and PCR.

The antibodies of the present invention may also be used to provide reagents for use in diagnostic assays for the detection of one or more NTHi SapA, SapB, SapC, SapD, SapF, SapZ and NTHi 110 kDa OMP proteins or peptides thereof in various body fluids of individuals suspected of *H. influenzae* infection. In another embodiment, the NTHi SapA, SapB, SapC, SapD, SapF, SapZ or NTHi 110 kDa OMP protein or peptides thereof of the present invention may be used as antigens in immunoassays for the detection of NTHi in various patient tissues and body fluids including, but not limited to: blood, serum, ear fluid, spinal fluid, sputum, urine, lymphatic fluid and cerebrospinal fluid. The antigens of the present invention may be used in any immunoassay system known in the art including, but not limited to: radioimmunoassays, ELISA assays, sandwich assays, precipitin reactions, gel diffusion precipitin reactions, immunodiffusion assays, agglutination assays, fluorescent immunoassays, protein A immunoassays and immunoelectrophoresis assays.

Vaccines and Chemotherapeutic Targets

As noted above, an aspect of the invention relates to a method for inducing an immune response in an individual, particularly a mammal, that comprises inoculating the individual with one or more NTHi SapA, SapB, SapC, SapD, SapF, SapZ and NTHi 110 IcDa OMP proteins or an antigenic peptides thereof. The present invention also provides for vaccine formulations that comprise one or more immunogenic recombinant NTHi SapA, SapB, SapC, SapD, SapF, SapZ and NTHi 110 kDa OMP proteins or peptides thereof together with a suitable carrier. The NTHi SapA, SapB, SapC, SapD, SapF, SapZ or NTHi 110 kDa OMP protein or peptides thereof are contemplated as vaccine candidates and/or targets of chemotherapy.

Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

A. Peptide Vaccines

Peptide therapeutic agents, such as peptide vaccines, are well known in the art and are of increasing use in the pharmaceutical arts. Consistent drawbacks to the parenteral administration of such peptide compounds have been the rapidity of breakdown or denaturation. Infusion pumps, as well as wax or oil implants, have been employed for chronic administration of therapeutic agents in an effort to both prolong the presence of peptide-like therapeutic agents and preserve the integrity of such agents. Furthermore, the peptide-like agent should (with particular reference to each epitope of the peptide-like agent) ideally maintain native state configuration for an extended period of time and additionally be presented in a fashion suitable for triggering an immunogenic response in the challenged animal.

The NTHi polypeptides or peptides thereof of the invention can be prepared in a number of conventional ways. The short peptides sequences can be prepared by chemical synthesis using standard means. Particularly convenient are solid phase techniques (see, e.g., Erikson et al., *The Proteins* (1976) v. 2, Academic Press, New York, p. 255). Automated solid phase synthesizers are commerically available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide. The short NTHi peptides can also be produced by recombinant techniques. The coding sequence for peptides of this length can easily be synthesized by chemical techniques, e.g., the phosphotriester method described in Matteucci et al., *J. Am Chem Soc.*, 103: 3185 (1981).

Where some of the NTHi peptide sequences contemplated herein may be considered too small to be immunogenic, they may be linked to carrier substances in order to confer this property upon them. Any method of creating such linkages known in the art may be used. Linkages can be formed with heterobifunctional agents that generate a disulfide link at one functional group end and a peptide link at the other, such as a disulfide amide forming agent, e.g., N-succidimidyl-3-(2-pyridyldithio)proprionate (SPDP) (See, e.g., Jansen et al., *Immun. Rev.* 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl)cyclohexane-1-carboxylic acid and the like, and coupling agents which activate carboxyl groups by combining them with succinimide or 1-hydroxy-2-nitro-4-sulfonic acid, for sodium salt such as succinimmidyl 4-(N-maleimido-methyl) cyclohexane-1-carobxylate (SMCC).

B. Vaccine Compositions and Administration

A priming dose of an immunogenic composition of the invention may be followed by one or more booster exposures to the immunogen. (Kramp et al., *Infect. Immun.*, 25: 771-773, 1979; Davis et al., *Immunology Letters*, 14: 341-8 1986 1987). moreover, examples of proteins or polypeptides that could beneficially enhance the immune response if co-administered include cytokines (e.g., IL-2, IL-12, GM-CSF), cytokine-inducing molecules (e.g. Leaf) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Ideally, an immunogen will exhibit two properties; the capacity to stimulate the formation of the corresponding antibodies and the propensity to react specifically with these antibodies. Immunogens bear one or more epitopes that are the smallest part of an immunogen recognizable by the combing site of an antibody. In particular instances, immunogen, fractions of immunogens or conditions under which the immunogen is presented are inadequate to precipitate the desired immune response resulting in insufficient immunity. This is often the case with peptides or other small molecules used as immunogens. Other substances such as immunomodulators (e.g., cytokines such as the interleukins) may be combined in vaccines as well.

The vaccine art recognizes the use of certain substances called adjuvants to potentate an immune response when used in conjunction with an immunogen. Adjuvants are further used to elicit an immune response that is faster or greater than would be elicited without the use of the adjuvant. In addition, adjuvants may be used to create an immune response using less immunogen than would be needed without the inclusion of adjuvant, to increase production of certain antibody subclasses that afford immunogenic protection or to enhance components of the immune response (e.g., humoral, cellular). Known adjuvants include emulsions such as Freund's Adjuvants and other oil emulsions, *Bordetella pertussis*, MF59, purified saponin from *Quillaja saponin* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli.*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

Vaccines are typically prepared as injectables, either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Vaccines may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazanes are useful for both transdermal and transmucosal administration. Polymeric complexes comprising synthetic poly-ornithate, poly-lysine and poly-arginine or amiphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-dioleyl-dihydroxypropyl)-N,N,N,-trimethylammonium-methyl sulfate (DOTAP), dioleyloxy-propyl-trimethylammonium chloride (DOTMA), dimystyloxypropyl-3-dimethyl-hydroxyethyl ammonium (DMRIE), dimethyldioctadecyl ammonium bromide (DDAB) and 9N(N',N-dimethylaminoethane)carbamoyl) cholesterol (DC-Chol). The combination of helper lipids and liposomes will enhance up-take of the liposomes through the skin. These helper lipids include, dioeolphosphatidyletha-nolamine (DOPE), dilauroylphosphatidylethanolamine (DLPE), dimystristoylphosphatidylethanolamine (DMPE), dipalmitoyl phosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

The proteins may be formulated into the vaccine as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or three month intervals by a subsequent injection or other administration.

Upon immunization with a vaccine composition as described herein, the immune system of the host responds to the vaccine by producing large amounts of CTLs specific for the desired antigen, and the host becomes at least partially immune to later infection, or resistant to developing chronic infection. Vaccine compositions containing one or more NTHi SapA, SapB, SapC, SapD, SapF, SapZ and NTHi 110 kDa OMP proteins or peptides thereof are administered to a patient susceptible to or otherwise at risk of bacterial infection or cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 per 70-kilogram patient, more commonly from about 10 to about 500 mg per 70 kg of body weight. For therapeutic or immunization purposes, the NTHi SapA, SapB, SapC, SapD, SapF, SapZ or NTHi 110 kDa OMP protein or peptides thereof may also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a noninfected host, the recombinant vaccinia virus expresses the immunogenic peptide, and thereby elicits a host CTL response.

Humoral immune response may be measured by many well-known methods, such as Single Radial Immunodiffussion Assay (SRID), Enzyme Immunoassay (EIA) and Hemagglutination Inhibition Assay (HAT). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test sera are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

Assays for measuring T-cell response are well known in the art. For example, T-cell response can be measured using delayed-type hypersensitivity testing, flow cytometry using peptide major histocompatibility complex tetramers, lymphoproliferation assay, enzyme-linked immunosorbant assay, enzyme-linked immunospot assay, cytokine flow cytometry, direct cytotoxicity assay, measurement of cytokine mRNA by quantitative reverse transcriptase polymerase chain reaction, and limiting dilution analysis. (See Lyerly, Semin Oncol., 30(3 Suppl 8):9-16, 2003).

Nontypeable *Haemophilus Influenzae* (NTHi)

*H. influenzae* is a small, nonmotile gram negative bacterium. Unlike other *H. influenzae* strains, the nontypable *H. influenzae* (NTHi) strains lack a polysaccharide capsule and are sometimes denoted as "nonencapsulated." NTHi strains are genetically distinct from encapsulated strains and are more heterogenous than the type b *H. influenzae* isolates. NTHi presents a complex array of antigens to the human host. Possible antigens that may elicit protection include OMPs, liposaccharises, lipoproteins, adhesion proteins and noncapsular proteins.

Humans are the only host for *H. influenzae*. NTHi strains commonly reside in the middle ear, upper respiratory tract including the nasopharynx and the posterior oropharynx, the lower respiratory tract and the female genital tract. NTHi causes a broad spectrum of diseases in humans, including but not limited to, otitis media, pneumonia, sinusitis, septicemia, endocarditis, epiglottitis, septic arthritis, meningitis, postpartum and neonatal infections, postpartum and neonatal sepsis, acute and chronic salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis.

Epidemiologic studies of NTHi have indicated that the strains are heterogeneous with respect to outer membrane protein profiles (Barenkamp et al., *Infect. Immun.*, 36: 535-40, 1982), enzyme allotypes (Musser et al., *Infect. Immun.*, 52: 183-191, 1986), and other commonly used epidemiologic tools. There have been several attempts to subtype NTHi, but none of the methodologies have been totally satisfactory. The outer-membrane protein composition of NTHi consists of approximately 20 proteins. All NTHi strains contain two common OMP's with molecular weights of 30,000 and 16,600 daltons. NTHi strains may be subtyped based on two OMP's within the 32,000-42,000 dalton range. The NTHi lipopolysaccharide profile is fundamentally different than the enteric Gram-negative bacteria and separates into several distinct bands less than 20,000 daltons in size.

A prototype NTHi isolate is the low passage isolate 86-028NP which was recovered from a child with chronic otitis media. This strain has been well characterized in vitro (Bakaletz et al., *Infect. Immun.*, 53: 331-5, 1988; Holmes et al., *Microb. Pathog.*, 23: 157-66, 1997) as well as in the chinchilla OM model (described herein) (Bakaletz et al., *Vaccine*, 15: 955-61, 1997; Suzuki et al., *Infect. Immun.*, 62: 1710-8, 1994; DeMaria et al., *Infect. Immun.*, 64: 5187-92, 1996). The 86-028NP strain was used, as described herein, to identify genes that are up-regulated in expression in the chinchilla model of otitis media and genes that are necessary for NTHi survival in the chinchilla middle ear.

The NTHi strain 86-026NP was deposited with the American Type Culture Collection, 10801 University Blvd., Manassas, Va. 20110, on Oct. 16, 2001 and assigned accession no. PTA-4764.

Signature-Tag Mutagenesis Strategy

The signature tag mutagenesis strategy (STM) has been employed to identify genes that are required for bacterial survival during infection in a number of systems. In this strategy, a series of mutants are constructed by random transposon mutagenesis. Each mutant was uniquely tagged with an oligonucleotide sequence that enables tag-specific identification of genes that alter virulence properties of a microorganism when mutated. The pool of mutants is then used to infect the experimental animal ('input pool'). After an appropriate period of time has elapsed, the surviving infecting organisms are recovered ('recovery pool').

Herein, the Tn903 kanamycin resistance gene was cloned into the EcoRI site of the pUC-based mini-Tn5 construction vector EZ::TN pMOD-2 (Epicentre). Oligonucleotide tags were prepared using the strategy of Nelson et al. (*Genetics*, 157: 935-47, 2001) and cloned into the KpnI site of the modified EZ::TN pMOD-2 vector. Individual tags were characterized to confirm that they hybridized uniquely. Seventy-eight unique tags were saved. Chromosomal DNA from strain 86-028NP was mutagenized with 38 individual tag-containing mini-Tn5 elements in vitro, gaps repaired with T4 polymerase and ligase, then mutagenized DNA was transformed back into strain 86-028NP using the M-IV method. Mutants were selected for growth on kanamycin-containing media. A signature tagged library containing 2500 clones was screened for mutants defective in their ability to survive in the chinchilla middle ear. The genes disrupted by the mini-Tn5 elements in avirulent mutants were identified by sequencing DNA flanking the mini-Tn5 elements. Template was prepared using single primer PCR strategy.

This analysis identified an avirulent clone containing a mutation in sapF. The sap operon has been shown in other systems to confer resistance to cationic antimicrobial peptides (Lopez-Solanilla et al., *Plant Cell*, 10(6): 917-24, 1998; McCoy et al., *Antimicrobiol. Agent Chemother.*, 45(7): 2030-7, 2001: Parra-Lopez et al., *EMBO J.*, 12(11): 4053-62, 1993). In vitro, the *H. influenzae* sapF mutant is more sensitive to cationic peptides suggesting that resistance to cationic peptides involved in innate immunity may be an important virulence determinant for *H. influenzae* in otitis media.

DFI Strategy

A differential fluorescence induction (DFI) strategy may be used to identify NTHi genes induced during OM in a chinchilla animal model. Several methods have been developed to identify bacterial genes that contribute to the virulence of an organism during infection. Such methods include in vivo expression technology (IVET) in which bacterial promoters regulate the expression of gene(s) required for synthesis of essential nutrients required for survival in the host; DNA microarray technology to globally screen for transcriptionally active genes, and DFI which uses FACS analysis to select for transcriptionally active promoters (Chiang et al., *Annu. Rev. Microbiol.*, 53: 129-154, 1999). DFI is a high-throughput method that allows for the identification of differentially regulated genes regardless of the basal level of expression and does not exclude those that are essential for growth in vitro.

DFI has been successfully utilized in many microorganisms. For example, a GFP reporter system and flow cytometry was used to study mycobacterial gene expression upon interaction with macrophages (Dhandayuthapani et al., *Mol. Microbiol.*, 17: 901-912, 1995). A promoter trap system was used to identify genes whose transcription was increased when *Salmonellae* were subjected to environments simulating in vivo growth and when internalized by cultured macrophage-like cells (Valdivia and Falkow, *Mol. Microbiol.*, 22: 367-378, 1996; Valdivia and Falkow, *Science*, 277: 2007-2011, 1997; Valdivia and Falkow, *Curr. Opin. Microbiol.*, 1: 359-363, 1998). In addition, DFI has been used to identify promoters expressed in *S. pneumoniae* and *S. aureus* when grown under varied in vitro conditions simulating infection (Marra et al., *Infect. Immzun.*, 148: 1483-1491, 2002; Schneider et al., *Proc. Natl. Acad. Sci. U.S.A.*, 97: 1671-1676, 2000). In addition, DFI has been utilized to study gene regulation in *Bacillus cereus* in response to environmental stimuli (Dunn and Handelsman, *Gene*, 226: 297-305, 1999), in *S. pneumoniae* in response to a competence stimulatory peptide (Bartilson et al., *Mol. Microbiol.*, 39: 126-135, 2001), and upon interaction with and invasion of host cells in *Bartonella henselae* (Lee and Falkow, *Infect. Immun.*, 66: 3964-3967, 1998), *Listeria monocytogenes* (Wilson et al., *Infect. Immun.*, 69: 5016-5024, 2001), *Brucella abortus* (Eskra et al., *Infect. Immun.*, 69: 7736-7742, 2001), and *Escherichia coli* (Badger et al., *Mol. Microbiol.*, 36: 174-182, 2000).

Animal Model

The chinchilla model is a widely accepted experimental model for OM. In particular, a chinchilla model of NTHi-induced OM has been well characterized (Bakaletz et al., *J. Infect. Dis.*, 168: 865-872, 1993; Bakaletz and Holmes, *Clin. Diagn. Lab. Immunol.*,4: 223-225, 1997; Suzuki and Bakaletz, *Infect. Immun.*, 62: 1710-1718, 1994), and has been used to determine the protective efficacy of several NTHi outer membrane proteins, combinations of outer membrane proteins, chimeric synthetic peptide vaccine components, and adjuvant formulations as vaccinogens against OM (Bakaletz et al., *Vaccine*, 15: 955-961, 1997; Bakaletz et al., *Infect. Immun.*, 67: 2746-2762, 1999; Kennedy et al., *Infect. Immun.*, 68: 2756-2765, 2000).

In particular, there is a unique in vivo model wherein adenovirus predisposes chinchillas to *H. influenzae*-induced otitis media, which allowed for the establishment of relevant cell, tissue and organ culture systems for the biological assessment of NTHi (Bakaletz et al., *J. Infect. Dis.*, 168: 865-72, 1993; Suzuki et al., *Infect. Immunity* 62: 1710-8, 1994). Adenovirus infection alone has been used to assess for the transudation of induced serum antibodies into the tympanum (Bakaletz et al., *Clin. Diagnostic Lab Immunol.*, 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., *Infect Immunity*, 67(6): 2746-62, 1999; Kennedy et al., *Infect Immun.*, 68(5): 2756-65, 2000; Novotny et al., *Infect Immunity* 68(4): 2119-28, 2000; Poolman et al,; *Vaccine* 19 (Suppl. 1): S108-15, 2000).

DETAILED DESCRIPTION

The following examples illustrate the invention wherein Example 1 describes construction of a signature-tagged mutagenesis library and identification of avirulent NTHi clones, Example 2 describes the characterization of the avirulent NTHi clone A1, Example 3 describes the in vitro phenotypic characterization of the NTHi sapF::mTn5 mutant, and Example 4 describes the OMP profile of the NTHi sapF::mTn5 mutant.

EXAMPLE 1

Construction of the STM Library

An attenuated NTHi mutant was identified by signature-tagged mutagenesis (STM) using the transbullar chinchilla model of OM. The NTHi, strain 86-028NP, was mutagenized by miniTn5 transposons marked with unique signature tags to construct an STM library. A panel of signature-tagged miniTn5 transposons was constructed by cloning an EcoRI cassette containing the Tn903 kanamycin resistance gene into the EcoRI site and a signature tag sequence into the KpnI site within the transposon of the Epicentre EZ::TN pMOD<MCS> Transposon Construction Vector. To ensure that the signature tag sequences give a strong hybridization signal and do not cross hybridize to other tags, the signature tag sequences were screened by dot blot hybridization. To adapt the Epicentre miniTn5 in vitro transposition mutagenesis system to strain 86-028NP, single stranded gaps generated by the transposase in the chromosomal DNA were repaired using DNA polymerase and ligase. The transposon inserted DNA was transformed back into the parent strain using M-IV transformation method described in Herriott et al. (*J. Bacterial.* 101: 513-6, 1970).

The individual kanamycin resistant clones with unique tags were assembled into 96 well plates for animal screening. Southern blot analysis was performed to confirm random and single insertion of the transposon in the STM mutants.

A pool of 38 STM mutants containing unique signature tags were directly inoculated into the middle ear cavity of a chinchilla at a concentration of $1.0 \times 10^6$ cfu/ear. The chinchilla was monitored for OM development and formation of effusions in the middle ear over a period of 48 hours by otoscopy and tympanometry. Effusions were removed by epitympanic taps and plated on chocolate agar plates supplanted with kanamycin to recover the NTHi mutants that survived in the middle ear. Bacteria recovered after two days of inoculation were selected as the recovery pool, at which time point the proliferation of NTHi cells in the middle ear reached a peak level during the course of OM development.

Figure 1:
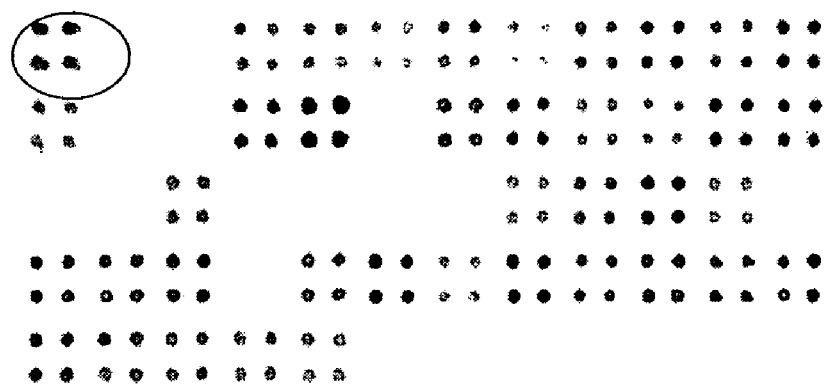
FIG. 1 depicts identification of attenuated A1 clone (circled) by comparative hybridization of signature tags present in the input pool (A) and the recovery pool (B).
Figure 1:
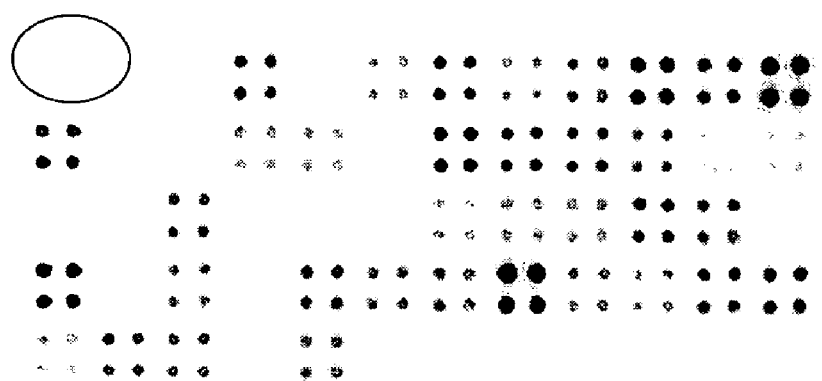

Bacterial genomic DNA isolated from the input and recovery pool was used as template for PCR amplification of signature tags. The input and recovery probes were hybridized to membranes spotted with each signature tag PCR product or oligonucleotide in quadruplicate. By comparing the input and recovery hybridization patterns as depicted in FIG. 1, attenuated mutants containing signature tags were identified within the input pool but not in the recovery pool. The mutant carrying the A1 tag (circled in FIG. 1) was cleared from the middle ear in two other independent STM animal experiments confirming that this mutant was attenuated in vivo. This mutant was subjected for further characterization as described below.

EXAMPLE 2

Characterization of the Attenuated A1 Clone

Figure 2:
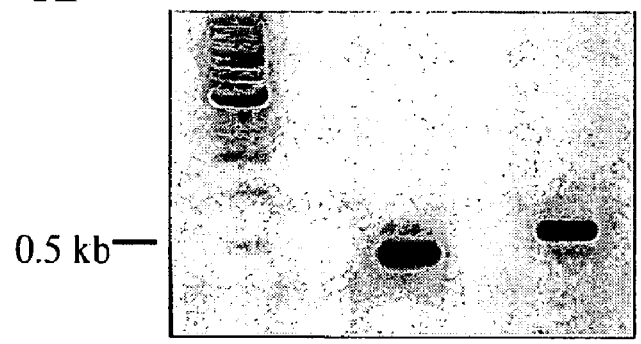
FIG. 2A and 2B depict that interruption of the sapF gene by the miniTn5 transposon had no polar effect on the downstream sapZ gene in the sapF::mTn5 mutant. RT-PCR analysis showing transcription of the sapZ gene (A). Insertion of miniTn5 in the sapF gene near the 3' end (B). Short avows are RT-PCR primers. Lines represent RT-PCR products.
Figure 2:
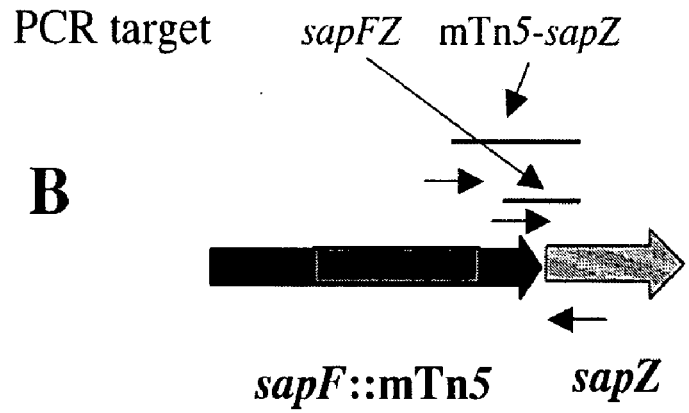

Sequence analysis was carried out on the transposon interrupted DNA locus in the attenuated strain using standard methods in the art. Southern blot analysis showed that a 6 kb EcoRV restricted genomic DNA fragment of the mutant of interest contained the transposon interrupted gene. The EcoRV restricted genomic DNA fragments were cloned into the pBluescript plasmid, and the transposon containing clone, designated pBlueA1, was isolated using marker rescue from LB agar plates supplemented with kanamycin. The 6 kb insert of the pBlueA1 plasmid was sequenced and the resulting DNA sequence data were searched against NCBI databases using the BLASTX and BLASTN algorithms. Contigs were assembled using SeqmanII software (DNASTAR Inc.). As shown in FIG. 2, sequence analysis indicated that the transposon was inserted 165 bp from the 3'-end of the sapF gene, thus this attenuated mutant was designated as "sapF::mTn5." The coding sequence of the kanamycin resistance gene is in the same orientation as the sapF gene.

A search of the *H. influenzae* Rd genome using the sapF DNA, identified the *Haemophilus* sap gene cluster containing 6 open reading frames (ORFs) in the order of sapABCDFZ, where the sapF was the fifth gene of the cluster followed by a hypothetical protein H11643 which we designated "sapZ" in this study. This study, utilized the genomic sequencing NTHi strain 86-028NP and a three-fold coverage contig assembly. Part of the sap operon was present in the contigs (Contigs 512 and 324; SEQ ID NO: 16-17). A pair of primers were designed according to the contig sequences to PCR amplify the whole sap operon from strain 86-028NP. Sequence comparison analysis showed that the sap operon of strain 86-028NP had 98% identity as that of strain Rd, and the sap genes were organized in the same way. The polynucleotide sequence of the sap operon genes (sapA, sapB, sap C, sapD, sapF, and sapZ) are set out as SEQ ID NOS: 1-6, respectively. The amino acid sequences of the sap operon gene products, SapA, SapB, SapC, SapD, SapF and SapZ, are set out as SEQ ID NOS: 7-12 respectively.

Figure 4:
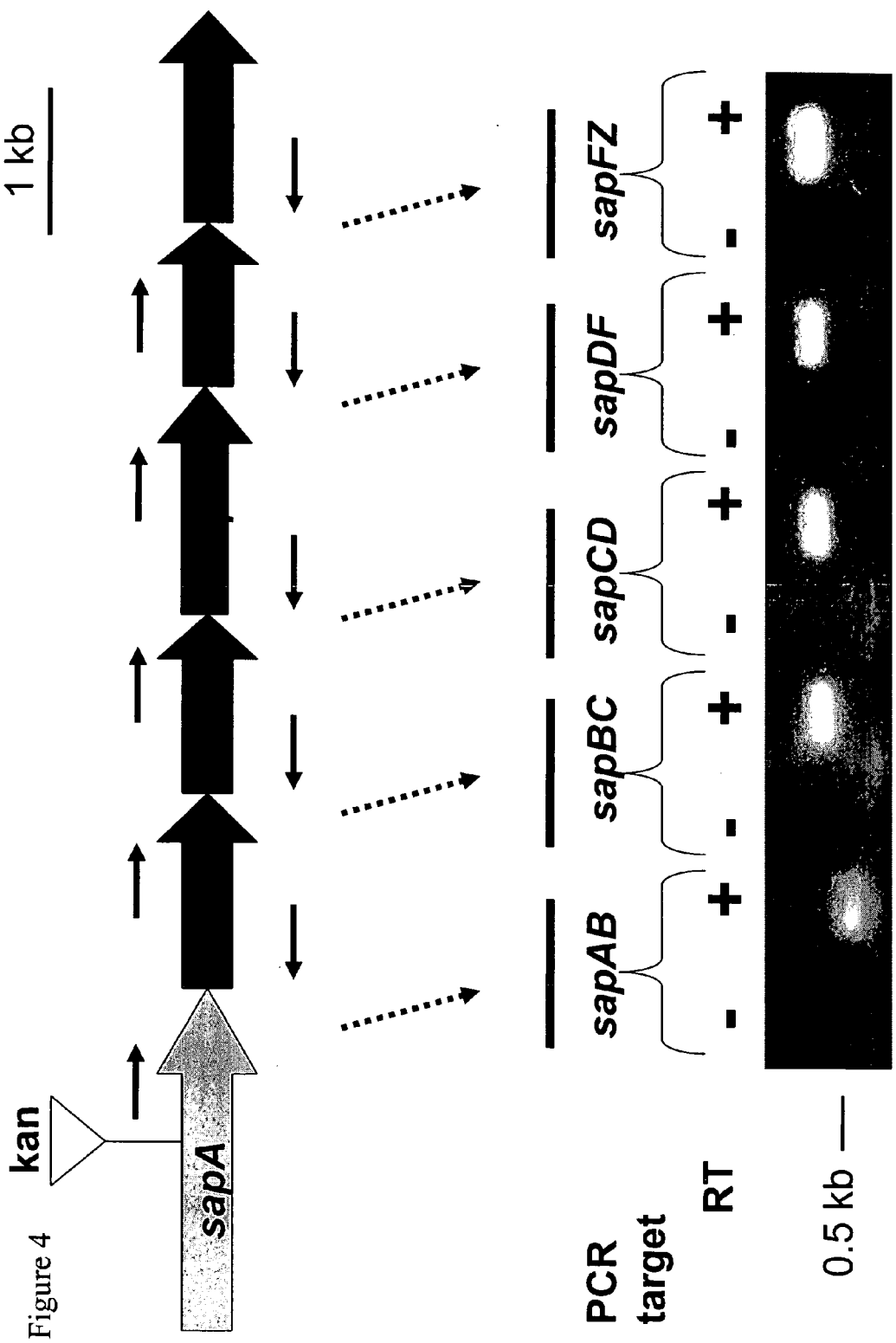
FIG. 4 depicts the gene order of the NTHi sap gene cluster. RT-PCR analysis demonstrates these genes are transcribed as an operon.

The sapF gene contains an ATP-binding domain and may share translocation ATPase activity with the sapD gene, shown to be up-regulated in response to iron and may play a role in potassium uptake via the TRK system (Harms et al., *Microbiology* 147: 2991-3003, 2001; Paustian et al. *J. Bacteriol*, 184:6714-20, 2002) The sapZ gene is unique to *Haemophilus*. SapZ is predicted to be a transmembrane protein with gene homologs in sap operon-containing bacteria, *P. multocida, S. typhimurium, S. enterica*, and *E. coli* 0157:H7, and in *Neisseria meningitidis* and *Pseudomonas aeruginosa*, which do not contain a sap operon. In bacteria containing the described sap system, however, sapZ is not located near the sap operon in the bacterial genome. The NTHi sap operon locus is organized as a single operon containing 6 genes as displayed in FIG. 4 and this gene locus was upregulated in vivo as determined by quantitative RT-PCR.

Figure 3:
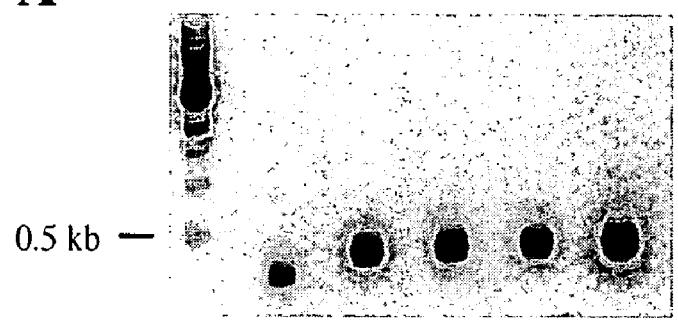
FIG. 3A and 3B depict RT-PCR analysis showing cotranscription of the sapABCDFZ genes as a single polycistronic mRNA. Transcriptional profile of the NTHi sap genes when grown in the sBHI media (A), and the computer predicted NTHi sap operon (B). Short avows are RT-PCR primers. Lines represent RT-PCR products.
Figure 3:
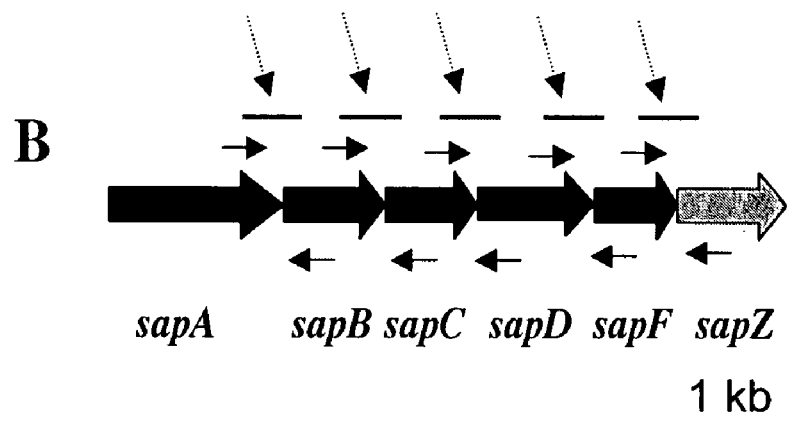

DNA sequence analysis indicated that the coding sequences of the 86-028NP 6 sap genes were located on the same DNA strand with very few non-coding bases between the ORFs (FIG. 3). When the sap gene cluster was scanned for transcriptional terminators (GCG Wisconsin package v. 10), one typical rho-independent terminator as a stem-loop structure followed by polyU sequence was found downstream of the sapZ gene. Therefore, the 6 NTHi sap genes were predicted to be organized in an operon structure and presumed to be co-transcribed as one polycistronic mRNA. The sapZ gene begins 11 nucleotides downstream of the end of the sapF gene and therefore it is highly likely that is co-transcribed with the sap gene cluster. To confirm this organization, RT-PCR was used to determine whether the region between the sap genes was transcribed. Each RT-PCR reaction utilized a primer from the 3' end of one gene and a primer from the 5' end of the following gene. If there was a PCR product, the two adjacent genes were cotranscribed. As amplicons were obtained from each junction region, all 6 sap genes were co-transcribed as one polycistronic mRNA (FIG. 3, upper panel), which was in agreement with the transcriptional property of the sap operon in *S. typhimurium* (Parra-Lopez et al, supra).

In order to determine whether insertion of the transposon prevented transcription of the downstream sapZ gene in the sapF::mTn5 mutant, a similar RT-PCR strategy using primers which annealed to the 3'-end of the sapF gene or the miniTn5 transposon and a primer which annealed to the 5'-end of the sapZ gene was employed. As depicted in FIG. 2, both primer sets gave positive results using sapF::mTn5 RNA as template demonstrating that there was detectable sapZ mRNA produced in the sapF::mTn5 mutant. The sapZ transcript in the mutant is presumably due to the absence of a transcriptional terminator downstream of the kanamycin resistance gene in the miniTn5 transposon. Thus, the attenuated phenotype of strain sapF::mTn5 was likely due to the sapF mutation but not the result of polar effect on the downstream sapZ gene.

EXAMPLE 3

In vitro Phenotypic Characterization of the sapF::mTn5 Mutant

To ensure no secondary mutation in the original sapF::mTn5 mutant contributed to the various phenotypes of this mutant, the parent strain 86-028NP was transformed with the 6 kb EcoRV fragment containing the sapF::mTn5 allele from the pBlueA1 plasmid. The wild type sapF gene was replaced in this strain by homologous recombination with the sapF::mTn5 allele. One Km resistant clone was confirmed to harbor a miniTn5 interrupted sapF gene by PCR and Southern blot analysis. This clone was further characterized together with the sapF::mTn5 strain and designated RcsapF::mTn5.

Since the sap mutants of *S. typhimurium* and *E. chrysanthemi* were reported to be hypersensitive to certain antimicrobial peptides, sensitivity to several commercial available cationic peptides against the NTHi parent and the sapF mutant strains was analyzed. Protamine displayed differential killing effect on the sapF mutants comparing to the parent strain. Broth minimal inhibitory concentration (MIC) analyses for protamine determined that the MIC of protamine for the sapF::mTn5 mutants was lower than that for the parent strain (0.2 mg/ml versus 0.4 mg/ml). Growth curve measurement under the same growth condition (aerobic growth in sBHI broth) demonstrated that the growth curves of the two mutant strains and the parent strain were identical. This analysis suggests that the two mutant strains do not possess a growth defect. Thus, the sapF gene product is not required for growth in enriched media, and the lack of growth of the sapF mutants at the lower protamine concentrations in sBHI broth was not due to a growth defect. Therefore, the sapF mutation may be responsible for the phenotype of increased sensitivity to protamine, and the in vivo attenuation property of the sapF mutant.

EXAMPLE 4

OMP Profile for the sapF::mTn5 Mutant NTHi Strain

The sapF mutant displayed a minor variation of OMP profile in comparison with the parent strain. Sarkosyl insoluble OMPs of the three strains were prepared using differential detergent extraction as described in Filip et al., (*J. Bacteriol*. 115: 717-722, 1973), and separated in a 10% SDS-PAGE. Absence of a 110 kDa OMP band was consistently observed from several OMP preparations in both mutant strains compared to the parent strain. Both the original and reconstructed mutant exhibited this minor change of the OMP profile, suggesting that the loss of the high molecular protein in the outer membrane was not due to a secondary mutation in the original sapF::mTn5 mutant.

To determine the amino acid sequence of the 110 kDa OMP protein, a tryptic digest was performed. The 110 kDa protein was digested overnight at 37° C. Subsequently the peptides (SEQ ID NOS: 22-39) were extracted, desalted (10%) using C18ziptip (Millipore), and analyzed by Matrix-assisted laser desorption ionization time-of-flight mass spectrometry (MALDI-TOF MS). The peptide information is set out below in Table 1. The MALDI monoisotopic peaks were then searched in the NCBInr database using the Profound computer program.

TABLE 1

| Peptide sequence | SEQ ID NO: | Residues | Computed mass | Meaured mass |
|---|---|---|---|---|
| FYAPGR | 22 | 998-1003 | 709.354 | 709.342 |
| LWQER | 23 | 530-534 | 730.376 | 730.372 |

TABLE 1-continued

| Peptide sequence | SEQ ID NO: | Residues | Computed mass | Meaured mass |
|---|---|---|---|---|
| FGQSGFAIR | 24 | 122-130 | 981.503 | 981.492 |
| AGVYNLTNR | 25 | 959-967 | 1006.519 | 1006.512 |
| YITWDSAR | 26 | 969-976 | 1010.482 | 1010.482 |
| KYITWDSAR | 27 | 968-976 | 1138.577 | 1138.582 |
| EFARINNGTR | 28 | 504-513 | 1176.599 | 1176.552 |
| YDNIHYQPK | 29 | 659-667 | 1176.556 | 1176.552 |
| LSFNPTENHR | 30 | 292-301 | 1213.583 | 1213.602 |
| SRGQDLSYTLK | 31 | 313-323 | 1266.656 | 1266.692 |
| YETGVTVVEAGR | 32 | 110-121 | 1279.640 | 1279.682 |
| NPEDTYDIYAK | 33 | 914-924 | 1327.593 | 1327.632 |
| FTLAADLYEHR | 34 | 302-312 | 1334.661 | 1334.722 |
| ELFEGYGNFNNTR | 35 | 157-169 | 1559.700 | 1559.802 |
| TMVYGLGYDHPSQK | 36 | 887-900 | 1594.744 | 1594.892 |
| VEHNLQYGSSYNTTMK | 37 | 556-571 | 1870.851 | 1870.972 |
| GYATENNQSFNTLTLAGR | 38 | 223-240 | 1955.933 | 1956.082 |
| KGYATENNQSFNTLTLAGR | 39 | 222-240 | 2084.028 | 2084.172 |

This analysis identified the 110 kDa OMP protein as H. influenzae hemoglobin binding protein (HGBA_HAEIN; Genebank Accession No. Q9KIV2 or closely related homologue) by the Emory Microchemical Facility. The amino acid sequence from HGBA_HAEIN (Q9KIV2) (SEQ ID NO: 15) was employed to query the 86-028NP genomic contig set using the TBLASTN algorithm. The translation of the compliment of nucleotides 2623 to 5358 of contig 516 (SEQ ID NO: 18) was a translated sequence that is closely related to amino acids 94 to 1013 of HGBA_HAEIN (SEQ ID NO: 15). Similarly, contig 411 (SEQ ID NO: 19) contains nucleic acid sequences whose translation is highly related to amino acids 59 to 148 of HGBA_HAEIN and less closely related to amino acids 147-969 of HGBA_HAEIN. Contig 2 (SEQ ID NO: 39) contains nucleic acid sequences whose translation is highly related to amino acids 1 to 122 of HGBA_HAEIN (SEQ ID NO: 15). Contigs 469 and 497 (SEQ ID NOS: 20 and 21) also contain sequences with homology to HGBA_HAEIN. The sequence similarity is summarized in Table 2 below. Additional sequence analysis identified the full length sequence of the NTHi 110 kDa OMP set out as SEQ ID NO: 41 that is encoded by the nucleic acid set out in SEQ ID NO: 40.

TABLE 2

| NTHi Contig # | Translation of Nucleotides of Contig with identity | Identity to Amino acids of SEQ ID NO: 15 | Total of number of amino acids with identity | Percent Identity |
|---|---|---|---|---|
| 516 | complement of 2623-5358 | 94-1013 | 752/928 | 81% |
| 469 | complement of 427-3462 | 59-1013 | 464/1043 | 44% |

TABLE 2-continued

| NTHi Contig # | Translation of Nucleotides of Contig with identity | Identity to Amino acids of SEQ ID NO: 15 | Total of number of amino acids with identity | Percent Identity |
|---|---|---|---|---|
| 411 | 651-3263 | 147-969 | 358/900 | 39% |
| 411 | 388-657 | 59-148 | 82/90 | 91% |
| 497 | 3377-4069 | 60-286 | 71/235 | 30% |
| 2 | 79-396 | 1-122 | 61/122 | 50% |

The sapF gene is 810 base pairs in length (SEQ ID NO: 5) and encodes a 269 amino acid protein (SEQ ID NO: 11) with a predicted mass of a 30 kDa soluble cytoplasmic protein with a an isoelectric point of 6.5. Therefore it is unlikely that the biosynthesis or secretion of this 110 kDa high molecular mass OMP is associated with the sapF gene product. Many OMPs of gram negative pathogens are important virulent factors playing roles in different pathogenesis aspects, such as host cells interaction, adhesion, iron acquisition, antigenic drift. The absence of the 110 kDa OMP may also contribute to the lost virulence of the sapF::Tn5 mutant.

EXAMPLE 5

Generation of a Non-Polar, In-Frame Mutant of NTHi Sap Operon

A set of clones with putative promoter activity in vivo were identified by differential fluorescence induction, and upregulated in vivo expression was confirmed by quantitative RT-PCR analysis as described in Mason et al. (*Infection and Immunity* 71: 3454-3462, 2003). A clone that contained sequence upstream of the sapA gene was isolated. This clone demonstrated up-regulated GFP fluorescence in vivo indicating increased transcription of the sap operon. SapA was predicted to localize to the periplasm due to its signal sequence and its sequence identity to periplasmic solute binding proteins involved in peptide transport. (Parra-Lopez et al., *EMBO J.* 12: 4053-62, 1993) It was predicted that a mutation in the sapa gene would disrupt the function of the sap operon, thereby demonstrating the involvement of SapA in survival in a chinchilla model of otitis media.

A non-polar mutation in the sapA gene was generated by insertion of a promoterless kanamycin resistance cassette as described in Menard et al. (*J. Bacterial.*, 175: 5899-906, 1993). The mutant construction was verified by Southern blot analysis and the resulting mutant is denoted herein as "sapA::kan mutant".

EXAMPLE 6

Properties of the SapA::kan Mutant

Defensins are known as important elements of innate immunity against microbial infections. In particular, beta-defensins function to protect the host against microbial infections such as Gram-negative bacteria infections. Recombinant chinchilla beta-defensin-1 (cBD-1), an antimicrobial peptide with homology to human beta-defensin-3, was used to assess the sensitivity of the sapA::kan mutant to antimicrobial protection.

Figure 5:
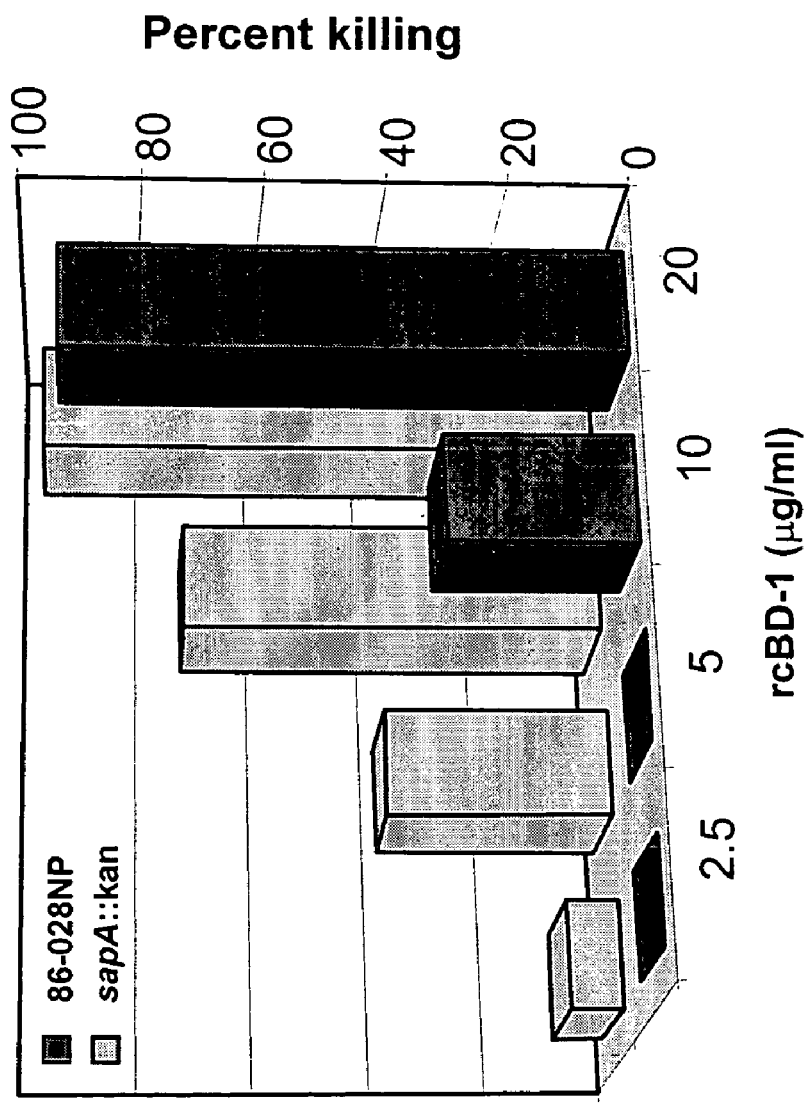
FIG. 5 depicts the sensitivity of NTHi bacterium with the sapA::kan mutation or the parental NTHi strain to killing induced by recombinant chinchilla beta-defensin-1 (cBD-1).

For microbicidal assays, NTHi strain 86-028NP or its isogenic sapA::kan mutant were cultured to mid-log phase in brain heart infusion (BHI) broth supplemented with 2 μg NAD/ml and 2 μg hemin/ml (sBHI) or on chocolate agar. Static cultures of NTHi, *S. pneumoniae* and *E. coli* were incubated in 5% $CO_2$ at 37° C. Various concentrations of recombinant cBD-1 (2.5, 5.0, 10.0 and 20 μg/ml) were incubated for 1 hour at 37° C. in 5% $CO_2$ with $1\times10^4$ microorganisms in 100 μl of 10 mM sodium phosphate buffer containing either 1% sBHI. Bacteria were serially diluted and plated onto chocolate agar and the CFU of surviving microorganisms per ml was determined following overnight incubation at 37° C. in 5% $CO_2$. Percent killing of the bacteria from a minimum of three replicate assays per strain are presented as mean percent survival (±SD) relative to concentration of (r)cBD-1 in FIG. 5. As shown in FIG. 5, the sapA::kan mutant strain had enhanced sensitivity to killing induced by recombinant chinchilla beta-defensin-1 as compared to the parental NTHi strain.

Survival of the sapA::kan mutant was also assessed in vivo. To conduct these studies, a small inoculum of either the parental NTHi strain alone, the sapA::kan mutant alone or a mixture of these two was inoculated into either the nasopharynx or the middle ears of a chinchilla (*Chinchilla lanigera*). At periodic time points following inoculation, a nasal lavage or middle ear tapping procedure is done in order to determine the number of bacteria (in colony forming units per milliliter fluid) present in each of these anatomic sites within the uppermost airway that are extremely relevant to the disease course of otitis media.

Figure 6:
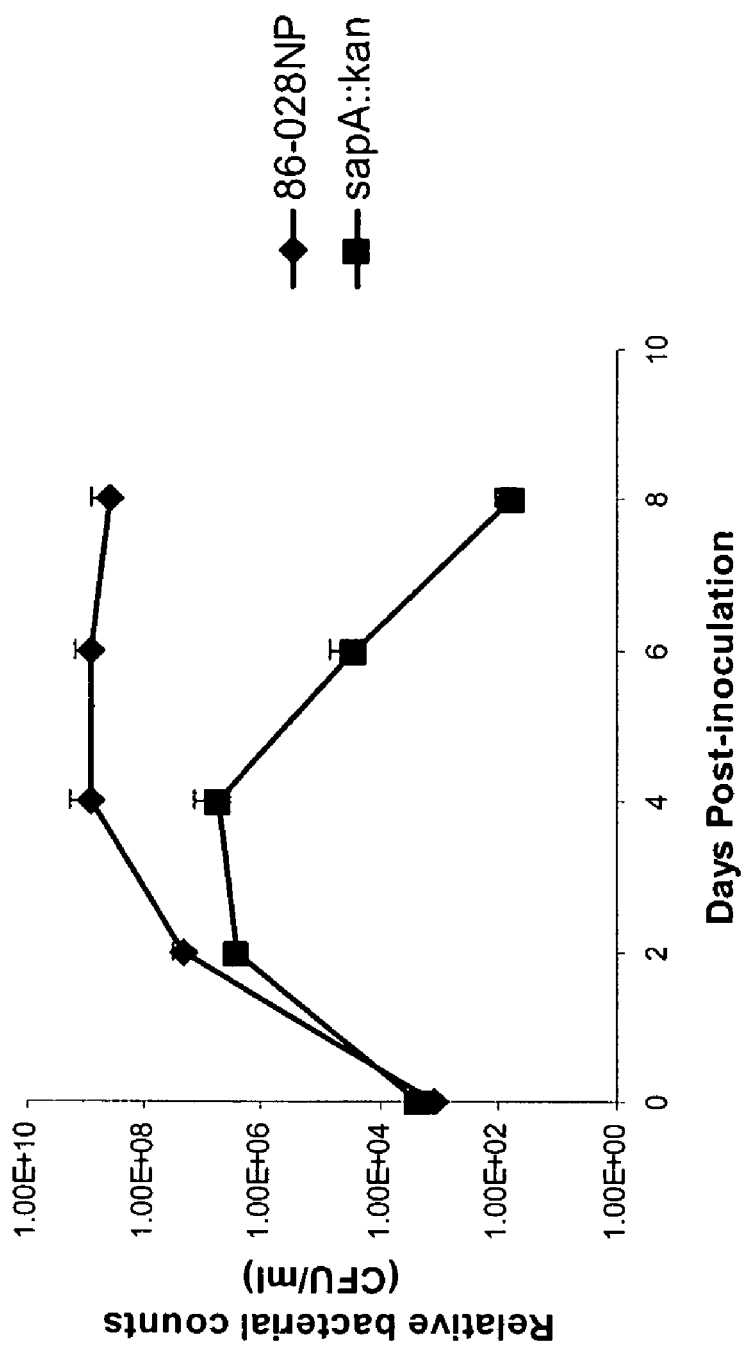
FIG. 6 depicts the relative bacterial counts in the chinchilla middle ear after inoculation of equal parts sapA::kan mutant NTHi and the parental NTHi strain. This plot depicts the inability of the sapA::kan mutant to survive in the middle ear while the parental strain maintained high bacterial counts.

In the competitive study wherein the parental NTHi strain and the sapA::kan mutant were mixed in equal parts and inoculated into chinchilla middle ears, as shown in FIG. 6, the ability of the sapA::kan mutant to survive in the middle ear was dramatically attenuated as compared to the parental strain. The parental strain behaved typically and was present at a very high bacterial load in the middle ears out to eight days after the challenge.

Figure 7:
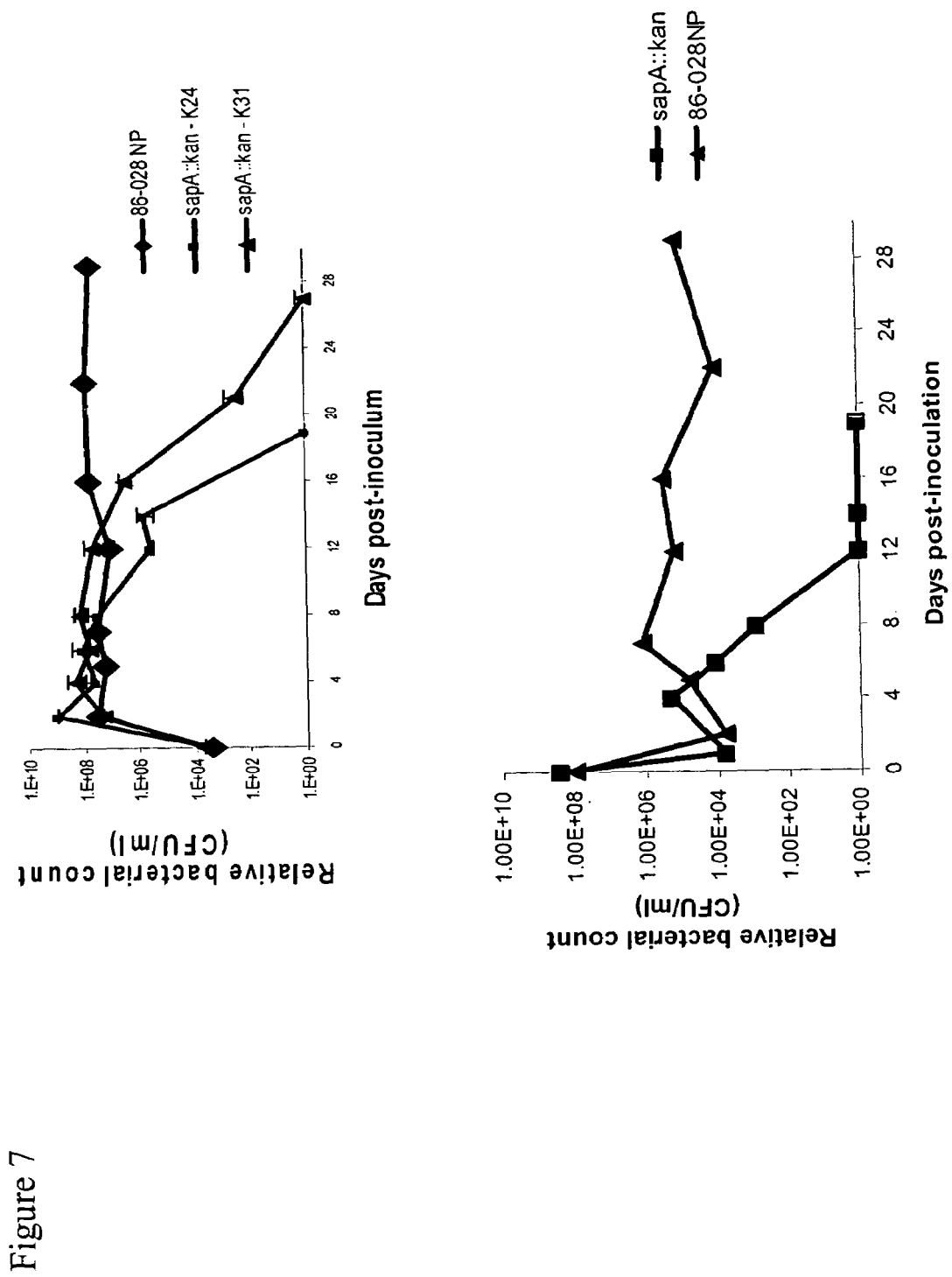
FIG. 7 depicts the ability of the sapA::kan mutant to survive when inoculated alone in the chinchilla middle ear (top panel) or in the chinchilla nasopharynx (bottom panel). These plots depict the inability of the sapA::kan mutant to survive in vivo while the parental strain maintained high bacterial counts.

In addition, the sapA::kan mutant was unable to survive when inoculated in the chinchilla middle ear alone as compared to the parental strain inoculated alone. As demonstrated in FIG. 7, in both animals challenged with the sapA::kan mutant, the bacteria were cleared from both ears of both animals by day 19 or 27 respectively. The parental isolate continued to be culturable at high numbers from the middle ear at these time points (FIG. 7; top panel). Similarly, the sapA::kan mutant was unable to survive when inoculated alone into the nasopharynx of a chinchilla (FIG. 7; bottom panel). Whereas the parental isolate maintained stable colonization of the nasopharynx, the sapA::kan mutant was cleared 12 days after challenge.

While the present invention has been described in terms of specific embodiments, it is understood that variations and modifications will occur to those skilled in the art. Accordingly, only such limitations as appear in the claims should be placed on the invention.

What is claimed is:

1. An isolated polypeptide comprising an amino acid sequence encoded by a nucleotide sequence of SEQ ID NO: 1.

2. An isolated polypeptide comprising an amino acid sequence of SEQ ID NO: 7.

3. A composition comprising a polypeptide of claim 1 or 2 and a pharmaceutically acceptable carrier.

* * * * *

UNITED STATES PATENT AND TRADEMARK OFFICE
CERTIFICATE OF CORRECTION

PATENT NO. : 7,306,805 B2  Page 1 of 1
APPLICATION NO. : 10/807746
DATED : December 11, 2007
INVENTOR(S) : Lauren O. Bakaletz et al.

It is certified that error appears in the above-identified patent and that said Letters Patent is hereby corrected as shown below:

At col. 1, line 9 replace

"Scientific work relating to the invention was supported by Grant No. DC03915 from United States National Institutes of Health. The United States government may have certain rights in the invention" with --The invention was made with government support under Grant No. RO1 DC03915 awarded by the United States National Institutes of Health. The United States government has certain rights in the invention.--

Signed and Sealed this

Eighteenth Day of May, 2010

David J. Kappos
*Director of the United States Patent and Trademark Office*